(12) United States Patent
Han et al.

(10) Patent No.: US 9,206,419 B2
(45) Date of Patent: Dec. 8, 2015

(54) TARGETING DOMAIN AND RELATED SIGNAL ACTIVATED MOLECULAR DELIVERY

(71) Applicants: CALIFORNIA INSTITUTE OF TECHNOLOGY, Pasadena, CA (US); CITY OF HOPE, Duarte, CA (US)

(72) Inventors: Si-ping Han, Yorba Linda, CA (US); William A. Goddard, III, Pasadena, CA (US); Lisa Scherer, Monrovia, CA (US); John J. Rossi, Alta Loma, CA (US)

(73) Assignees: CALIFORNIA INSTITUTE OF TECHNOLOGY, Pasadena, CA (US); CITY OF HOPE, Duarte, CA (US)

( * ) Notice: Subject to any disclaimer, the term of this patent is extended or adjusted under 35 U.S.C. 154(b) by 63 days.

(21) Appl. No.: 13/848,687

(22) Filed: Mar. 21, 2013

(65) Prior Publication Data

US 2014/0323542 A1    Oct. 30, 2014

Related U.S. Application Data

(60) Provisional application No. 61/613,617, filed on Mar. 21, 2012.

(51) Int. Cl.
*C12N 15/113*    (2010.01)
*C12N 15/11*    (2006.01)

(52) U.S. Cl.
CPC ............ *C12N 15/113* (2013.01); *C12N 15/111* (2013.01); *C12N 2310/14* (2013.01); *C12N 2310/3519* (2013.01); *C12N 2320/32* (2013.01)

(58) Field of Classification Search
CPC .............................. C12N 15/113; C12N 15/111
See application file for complete search history.

(56) References Cited

U.S. PATENT DOCUMENTS

| 8,710,199 B2 | 4/2014 | Han et al. |
| 2006/0088864 A1 | 4/2006 | Smolke et al. |
| 2009/0082217 A1 | 3/2009 | Smolke et al. |
| 2009/0234109 A1 | 9/2009 | Han et al. |

FOREIGN PATENT DOCUMENTS

| WO | 2007/107162 | 9/2007 |
| WO | 2011/163526 | 12/2011 |

OTHER PUBLICATIONS

Wu, H., et al., "Properties of cloned and expressed human RNase H1," *The Journal of Biological Chemistry*, 1999, vol. 274, pp. 28270-28278.

Zamaratski, E., et al., "A critical survey of the structure-function of the antisense oligo/RNA heteroduplex as substrate for RNase H," *Journal of Biochemical and Biophysical Methods*, 2001, vol. 48, pp. 189-208.

Cazenave, C., et al., "Characterization and subcellular localization of ribonuclease Activities From Xenopus laevia oocytes," *The Journal of Biological Chemistry*, 1994, vol. 269, pp. 25185-25192.

Nowotny, M., et al. Crystal structures of RNase H bound to an RNA/DNA hybrid: substrate specificity and metal-dependent catalysis, *Cell*, 2005, vol. 121, pp. 1005-1016.

Song, J. J. et al., "The crystal structure of the Argonaute2 PAZ domain reveals an RNA binding motif in RNAi effector complexes", *Nature Structural Biology*, vol. 10, pp. 1026-1032 (2003).

Ma, J. B. et al., "Structural basis for overhang-specific small interfering RNA recognition by the PAZ domain", *Nature*, vol. 429, pp. 318-322 (2004).

Yan, K. S. et al., "Structure and conserved RNA binding of the PAZ domain", *Nature*, vol. 426, pp. 468-265 (2003).

Lingel, A. et al., "Structure and nucleic-acid binding of the Drosophila Argonaute 2 PAZ domain", *Nature*, vol. 426, pp. 465-469 (2003).

Behlke, M. A. et al., "Chemical modification of siRNAs for in vivo use", *Oligonucleotides*, vol. 18, pp. 305-320 (2008).

Rose, S. D. et al., "Functional polarity is introduced by Dicer processing of short substrate RNAs", *Nucleic Acids Research*, vol. 33, pp. 4140-4156 (2005).

Tomari, Y., et al., "A Protein Sensor for siRNA Asymmetry", *Science*, vol. 306, pp. 1377-1380, (2004).

Susan M. Freier and Karl-Heinz Altman, "The ups and downs of nucleic acid duplex stability: structure-stability studies on chemically-modified DNA:RNA duplexes," *Nucleic Acids Research*, 1997, vol. 25, No. 22 4429-4443.

Majlessi, M. et al. "Advantages of 2'-O-methyl oligoribonucleotide probes for detecting RNA targets," *Nucleic Acids Research*, 1998, vol. 26, No. 9, pp. 2224-2229.

Kierzek, E. et al. "The influence of locked nucleic acid residues on the thermodynamic properties of 2'-O-methyl RNA/RNA heteroduplexes," *Nucleic Acids Research*, 2005, vol. 33, No. 16, pp. 5082-5093.

Yakovchuk, P. et al. "Base-stacking and base-pairing contributions into thermal stability of the DNA double helix *Nucleic Acids Research*," 2006, vol. 34, No. 2, pp. 564-574.

Han, H. et al. "Sequence-specific recognition of double helical RNA and RNA.DNA by triple helix formation," *PNAS* May 1, 1993 vol. 90, pp. 3806-3810.

Burge S, Parkinson GN, Hazel P, Todd AK, Neidle S (2006). "Quadruplex DNA: sequence, topology and structure". *NAR* 34 (19): 5402-5415. doi:10.1093/nar/gkl655.

(Continued)

*Primary Examiner* — Jon E Angell
(74) *Attorney, Agent, or Firm* — Steinfl & Bruno LLP

(57) ABSTRACT

Provided herein are signal activatable molecular constructs for enzyme-assisted delivery of molecules and related components, such as a sensor domain, compositions, methods and systems.

23 Claims, 35 Drawing Sheets

(56) References Cited

OTHER PUBLICATIONS

J.N. Zadeh, C.D. Steenberg, J.S. Bois, B.R. Wolfe, M.B. Pierce, A.R. Khan, R.M. Dirks, N.A. Pierce. "NUPACK: analysis and design of nucleic acid systems." *J Comput Chem*, 32, 170-173, 2011.

R.M. Dirks, J.S. Bois, J.M. Schaeffer, E. Winfree, and N.A. Pierce. (2007) "Thermodynamic analysis of interacting nucleic acid strands." *SIAM Rev*, 49, 65-88.

R.M. Dirks and N.A. Pierce. (2003) "A partition function algorithm for nucleic acid secondary structure including pseudoknots." *J Comput Chem*, 24, 1664-1677.

R.M. Dirks and N.A. Pierce. (2004) "An algorithm for computing nucleic acid base-pairing probabilities including pseudoknots." *J Comput Chem*, 25, 1295-1304.

J.N. Zadeh, B.R. Wolfe, N.A. Pierce. "Nucleic acid sequence design via efficient ensemble defect optimization." *J Comput Chem*, 32, 439-452, 2011.

M. Zuker. "Mfold web server for nucleic acid folding and hybridization prediction." *Nucleic Acids Res*. 31 (13), 3406-3415, 2003.

Waugh, P. Gendron, R. Altman, J. W. Brown, D. Case, D. Gautheret, S. C. Harvey, N. Leontis, J. Westbrook, E. Westhof, M. Zuker & F. Major."RNAML: A standard syntax for exchanging RNA information." *RNA* 8 (6), 707-717, 2002.

M. Zuker & A. B. Jacobson. "Using Reliability Information to Annotate RNA Secondary Structures." *RNA* 4, 669-679, 1998. [Abstract][Preprint] Note: Explains color annotation of secondary structure.

N. R. Markham & M. Zuker. "UNAFold: Software for Nucleic Acid Folding and Hybridization. In Data, Sequence Analysis, and Evolution," J. Keith, ed., *Bioinformatics*: vol. 2, Chapter 1, pp. 1-33, Humana Press Inc., 2008.

M. Zuker, D. H. Mathews & D. H. Turner. "Algorithms and Thermodynamics for RNA Secondary Structure Prediction: A Practical Guide In RNA Biochemistry and Biotechnology," pp. 1-23, J. Barciszewski and B. F. C. Clark, eds., NATO ASI Series, Kluwer Academic Publishers, Dordrecht, NL, 1999.

M. Zuker. "Prediction of RNA Secondary Structure by Energy Minimization. In Computer Analysis of Sequence Data" A. M. Griffin and H. G. Griffin eds. Methods in Molecular Biology, Humana Press Inc., 267-294, 1994.

J. A. Jaeger, D. H. Turner & M. Zuker. "Predicting Optimal and Suboptimal Secondary Structure for RNA." In Molecular Evolution: Computer Analysis of Protein and Nucleic Acid Sequences, R. F. Doolittle ed. Methods in Enzymology 183, 281-306, 1990.

M. Zuker. "On Finding All Suboptimal Foldings of an RNA Molecule." *Science* 244, 48-52, 1989.

D. H. Mathews, J. Sabina, M. Zuker & D. H. Turner. "Expanded Sequence Dependence of Thermodynamic Parameters Improves Prediction of RNA Secondary Structure," J. Mol. Biol. 288, 911-940, 1999.

E. Walter, D. H. Turner, J. Kim, M. H. Lyttle, P. Müller, D. H. Mathews & M. Zuker. "Coaxial stacking of helixes enhances binding of oligoribonucleotides and improves predictions of RNA folding." *Proc. Natl. Acad. Sci. USA* 91, 9218-9222, 1994.

Mathews, D. H. et al. "RNA Secondary Structure Prediction." *In Current Protocols in Nucleic Acid Chemistry* S. Beaucage, D. E. Bergstrom, G. D. Glick, and R. A. Jones eds., John Wiley & Sons, New York, 11. 2. 1-11. 2. 10, (2007) DOI: 10.1002/0471142700.nc1102s28.

D. H. Mathews, S. J. Schroeder, D. H. Turner & M. Zuker. "Predicting RNA Secondary Structure." In the RNA World, R. F. Gesteland, T. R. Cech and J. F. Atkins eds., 3rd edition, Cold Spring Harbor Laboratory Press, Cold Spring Harbor, New York, Chapter 22, 631-657, 2006.

D. H. Mathews & M. Zuker."Predictive Methods Using RNA Sequences." In Bioinformatics: A Practical Guide to the Analysis of Genes and Proteins, A. Baxevanis and F. Ouellette eds., 3rd edition, John Wiley & Sons, New York, Chapter 6, 143-164, 2005.

D. H. Mathews, M. D. Disney, J. L. Childs, S. J. Schroeder, M. Zuker & D. H. Turner."Incorporating chemical modification constraints into a dynamic programming algorithm for prediction of RNA secondary structure." Proc. Natl. Acad. Sci. USA 101 (19), 7287-7292, 2004.

M. Zuker & D. Sankoff."RNA Secondary Structures and their Prediction." Bull. Mathematical Biology 46, 591-621, 1984.

M. Zuker & P. Stiegler. "Optimal computer folding of large RNA sequences using thermodynamics and auxiliary information." *Nucleic Acids Res*. 9, 133-148, 1981.

J. -M. Rouillard, M. Zuker & E. Gulari. "OligoArray 2. 0: design of oligonucleotide probes for DNA microarrays using a thermodynamic approach." *Nucleic Acids Res*. 31 (12), 3057-3062, 2003.

J. -M. Rouillard, C. J. Herbert & M. Zuker. "OligoArray: Genome-scale oligonucleotide design for microarrays." *Bioinformatics* 18 (3), 486-487, 2002.

Ding, Y. et al. "RNA secondary structure prediction by centroids in a Boltzmann weighted ensemble," *RNA* 2005. 11: pp. 1157-1166.

Braasch, D.A. et al. "RNA Interference in Mammalian Cells by Chemically-Modified RNA," *Biochemistry* 2003,42, pp. 7967-7975.

Jin-Biao Ma, Keqiong Ye & Dinshaw J. Patel"Structural basis for overhang specific small interfering RNA recognition by the PAZ domain," *Nature*, 429, 318-322 (2004).

Whitehead, K.A. et al. Nature Reviews Drug Discovery 8, 129-138 (Feb. 2009) | doi:10.1038/nrd2742, "Knocking down barriers: advances in siRNA delivery".

Simeoni, F. "Insight into the mechanism of the peptide.based gene delivery system MPG: implications for delivery of siRNA into mammalian cells." *Nucleic acids research* 31.11 (2003):2717-2724.

Liu, Z., Winters, M., Holodniy, M. and Dai, H. (2007), "siRNA Delivery into Human T Cells and Primary Cells with Carbon-Nanotube Transporters." *Angewandte Chemie*, 119: 2069-2073. doi:10.1002/ange.200604295.

Chu, T.C. et al. "Aptamer mediated siRNA delivery," *Nucl. Acids Res*. 34(10): e73 doi:10.1093/nar/gkl388.

Rozema, D.B. et al. "Dynamic PolyConjugates for targeted in vivo delivery of siRNA to hepatocytes," *PNAS* 2007 104 (32) 12982-12987.

Derfus, A.M. et al. "Targeted Quantum Dot Conjugates for siRNA Delivery," *Bioconjugate Chem*., 2007, 18 (5), pp. 1391-1396, DOI: 10.1021/bc060367e.

Kumar, P. et al. "T Cell-Specific siRNA Delivery Suppresses HIV-1 Infection in Humanized Mice," *Cell*, vol. 134, Issue 4, Aug. 22, 2008, pp. 577-586.

Rinaudo, K. et al. "A universal RNAi-based logic evaluator that operates in mammalian cells," *Nature Biotechnology* 25, 795-801 (2007).

Ehsani, A. et al. "Rational Design of Micro-RNA-like Bifunctional siRNAs Targeting HIV and the HIV Coreceptor CCR5" *Molecular Therapy* (2010) 18:4, pp. 796-802. doi:10.1038/mt.2009.321.

Tiemann, K. et al."Dual-targeting siRNAs" RNA (2010), 16: pp. 1275-1284.

Judge, A.D. et al. "Design of Noninflammatory Synthetic siRNA Mediating Potent Gene Silencing in Vivo," *Molecular Therapy* (2006) 13, pp. 494-505.

Blight K.J. et al., "Secondary Structure Determination of the Conserved 98-Base Sequence at the 3' Terminus of Hepatitis C Virus Genome RNA" Journal of Virology, Oct. 1997, vol. 71, pp. 7345-7352.

Ehsani, A. et al. "Rational Design of Micro-RNA-like Bifunctional siRNAs Targeting HIV and the HIV Coreceptor CCR5," Molecular Therapy (2010) 18;3, pp. 796-802. doi;10.138/mt.2009.321.

PCT International Search Report mailed on Feb. 24, 2012 for PCT Application No. PCT/US2011/041703 filed Jun. 23, 2011 in the name of California Institute of Technology et al.

PCT Written Opinion completed on Feb. 22, 2012 for PCT Application No. PCT/US2011/041703 filed Jun. 23, 2011 in the name of California Institute of Technology et al.

Li, J. et al., "Enzymatic signal amplification of molecular beacons for sensitive DNA detection," Nucleic Acid Research 2008, 36: 1-17.

Weissleder, R., et al "In vivo imaging of tumors with proteaseactivated near-infrared fluorescent probes," Nature Biotechnology 1999, 17: 375-378.

(56) References Cited

OTHER PUBLICATIONS

PCT International Search Report mailed on Jul. 9, 2013 for PCT Application No. PCT/US2013/033380 filed Mar. 21, 2013 in the name of California Institute of Technology et al.

PCT Written Opinion mailed on Jul. 9, 2013 for PCT Application No. PCT/US2013/033380 filed Mar. 21, 2013 in the name of California Institute of Technology et al.

De Paula, D. et al. "Hydrophobization and bioconjugation for enhanced siRNA delivery and targeting." RNA, vol. 13, pp. 431-456, 2007.

Kim, J. et al. "Intracellular small interfering RNA delivery using genetically engineered double-stranded RNA binding protein domain." The Journal of Gene Medicine. vol. 11, pp. 804-812, 2009.

Wang, H.W. et al. "Structural Insights into RNA Processing by the Human RISC-Loading Complex." Nat Struct Mol Biol., vol. 16(1), pp. 1148-1153, 2009.

Mathews, D.H. et al. "Folding and Finding RNA Secondary Structure." Cold Spring Harbor Perspectives in Biology. 2010.

Restriction Requirement issued for U.S. Appl. No. 13/167,672, filed Jun. 23, 2011 filed in the name of Si-Ping Han mailed on Dec. 14, 2012.

Non-Final Office Action issued for U.S. Appl. No. 13/167,672, filed Jun. 23, 2011 filed in the name of Si-Ping Han mailed on Apr. 1, 2013.

Notice of Allowance issued for U.S. Appl. No. 13/167,672, filed Jun. 23, 2011 filed in the name of Si-Ping Han mailed on Dec. 12, 2013.

Matsukura, M. et al. "Phosphorothioate analogs of oligodeoxynucleotides: inhibitors of replication and cytopathic effects of human immunodeficiency virus." Proceedings of the National Academy of Sciences 84, 7706-7710 1987.

Collingwood, M., et al. "Chemical Modification Patterns Compatible with High Potency Dicer-Substrate Small Interfering RNAs." Oligonucleotides 18, 187-200 2008.

Lennox, K. A., et al. "Improved Performance of Anti-miRNA Oligonucleotides Using a Novel Non-Nucleotide Modifier." Mol Ther Nucleic Acids 2, e117, doi:10.1038/mtna.2013.46 2013.

Bramsen, J. B., et al. "A large-scale chemical modification screen identifies design rules to generate siRNAs with high activity, high stability and low toxicity." Nucleic Acids Research 37, 1-15, doi:10.1093/nar/gkp106 2009.

Mathy, N., et al. "5'-to-3' Exoribonuclease Activity in Bacteria: Role of RNase J1 in rRNA Maturation and 5' Stability of mRNA." Cell 129, 681-692 2007.

Yang X. et al. "Studies of the 5' Exonuclease and Endonuclease Activities of CPSF-73 in Histone Pre-mRNA Processing." Molecular and Cellular Biology 29, 31-42, doi:10.1128/mcb.00776-08 2009.

Efthymiou, T. C. et al "Evaluation of siRNAs that contain internal variable-length spacer linkages." Bioorganic & Medicinal Chemistry Letters 22, 5590-5594, doi:http://dx.doi.org/10.1016/j.bmcl.2012.07.006 2012.

Zhou, J., et al. Selection, characterization and application of new RNA HIV gp 120 aptamers for facile delivery of Dicer substrate siRNAs into HIV infected cells. Nucleic Acids Research 37, 3094-3109, doi:10.1093/nar/gkp185 2009.

Lee, H. et al. Molecular Dynamics Studies of Polyethylene Oxide and Polyethylene Glycol: Hydrodynamic Radius and Shape Anisotropy. Biophysical Journal, vol. 95, Aug. 2008, pp. 1590-1599.

Yurke, B. et al. A DNA-fuelled molecular machine made of DNA. Letters to Nature, vol. 406, Aug. 10, 2000, pp. 605-608.

IDT—Integrated DNA Technologies. OligoAnalyzer 3.1. Web. Retrieved from <http://www.idtdna.com/calc/analyzer> on Nov. 19, 2014, 2 pgs.

NUPACK—Nucleic Acid Package. Web. Retrieved from <http://www.nupack.org> on Nov. 19, 2014, 1 pg.

GeneLink. Gene Assays & SPCT. Web. Retrieved from <http://genelink.com> on Nov. 19, 2014, 1 pg.

Restriction Requirement issued for U.S. Appl. No. 14/093,387, filed Nov. 29, 2013 in the name of California Institute of Technology et al. mail date: Nov. 19, 2014.

Restriction Requirement issued for U.S. Appl. No. 11/978,219, filed Oct. 26, 2007 in the name of Si-ping Han et al. mail date: Jun. 4, 2014.

Non-Final Office Action issued for U.S. Appl. No. 11/978,219, filed Oct. 26, 2007 in the name of Si-ping Han et al. mail date: Sep. 30, 2014.

Patterning Definition. Retrieved on Dec. 5, 2014 from the internet: <https://www.google.com/search?q=patterning+definition&spell=1>, 2 pgs.

Song, J.H., et al. Crystal Overgrowth on Gold Nanorods: Tuning the Shape, Facet, Aspect Ratio, and Composition of the Nanorods. Chem. Eur. J. vol. 11, pp. 910-916. 2005.

Wang, J., et al. Silver Enhanced Colloidal Gold Electrochemical Stripping Detection of DNA Hybridization. Langmuir, vol. 17, pp. 5739-5741. 2001.

Gu, Q. et al. DNA nanowire fabrication. Nanotechnology, vol. 17, R14-R25. 2006.

Foultier, B., et al. Comparison of DNA detection methods using nanoparticles and silver enhancement. IEE Proc.-Nanobiotechnolo., vol. 152(1), pp. 3-12. 2005.

Barish, R.D. et al. An information-bearing seed for nucleating algorithmic self-assembly. PNAS, 106, pp. 1-6. 2009.

Fu, T.J., et al. DNA Double-Crossover Molecules. Biochemistry, 32, pp. 3211-3220. 1993.

Winfree, E., et al. Design and self-assembly of two-dimensional DNA crystals. Nature, vol. 394, pp. 539-544. 1998.

Zhang, Y., et al. Construction of a DNA-Truncated Octahedron. J. Am. Chem. Soc. vol. 116, pp. 1661-1669. 1994.

Chen, J., et al. Synthesis from DNA of a molecule with the connectivity of a cube. Letters to Nature, vol. 350, pp. 631-633. Apr. 1991.

Rothemund, P.W.K. Folding DNA to create nanoscale shapes and patterns. Nature, vol. 440, pp. 297-302. 2006.

Rothemund, P.W.K. et al. Algorithmic Self-Assembly of DNA Sierpinski Triangles. PLoS Biology 2(12), e424, pp. 2041-2053. 2004.

Barish, R.D., et al. Two Computational Primitives for Algorithmic Self-Assembly: Copying and Counting. Nano Letters, vol. 5(12), pp. 2586-2592. 2005.

Yan, H., et al. Directed nucleation assembly of DNA tile complexes for barcode-patterned lattices. Proc. Natl. Acad. Sci., vol. 100(14), pp. 8103-8108. 2003.

Schulman, R. et al. Programmable Control of Nucleation for Algorithmic Self-assembly. In DNA Computing 10. Springer-Verlag: Berlin, Heidelberg, pp. 319-328. 2005.

Winfree-E. Self-healing Tile Sets, In Nanotechnology: Science and Computation, pp. 55-78. 2006.

Undecagold. Nanoprobes. Revised 1.1. 2 pgs. Mar. 2000.

Goldenhance. Nanoprobes. Revised 1.5. 3 pgs. Oct. 2013.

Non-Final Office Action issued for U.S. Appl. No. 14/093,387, filed Nov. 29, 2013 in the name of Si-ping Han et al. mailed on Feb. 26, 2015.

Exiqon. LNA™ Oligo Tools and Design Guidelines. Web. Retreived from <https://www.exiqon.com/oligo-tools> on Mar. 16, 2015.

"Worm-like Chain," Wikipedia: The Free Encyclopedia. Wikimedia Foundation, Inc. Web. Retrieved from <http://en.wikipedia.org/wiki/Worm-like_chain> on Mar. 26, 2015.

"Int Cy5™,"IDT—Integrated DNA Technologies. Web. Retrieved from <http://www.idtdna.com/site/Catalog/Modifications/Product/1476> on Mar. 26, 2015.

"The mfold Web Server." The RNA Institute College of Arts and Sciences. Web. Retrieved from <http://mfold.ma.albany.edu/?q=mfold> Mar. 26, 2015.

"Sfold." Software for Statistical Folding of Nucleic Acids and Studies of Regulatory RNAs. Web. Retrieved from <http://sfold.wadsworth.org/cgi-bin/index.pl> on Mar. 26, 2015.

Diao, J.J. et al. "Self assembled nanoparticle wires by discontinuous vertical colloidal deposition." Applied Physics Letters, vol. 87. 103113, pp. 1-3 (2005).

"Divalent." Wikipedia: The Free Encylcopedia, Wikimedia Foundation, Inc. Web. Retrieved from <http://en.wikipedia.org/wiki/Divalent> on Mar. 16, 2015.

Northern, D.B.L. et al. "Atomic Force Microscopy of Mica Surface After Ion Replacement." Proceedings of the 49th Annual Meeting of the Electron Microscopy Society of America. San Francisco Press, Inc.: San Francisco. 1991.

(56) References Cited

OTHER PUBLICATIONS

Scheibel, T. et al. "Conducting nanowires built by controlled self-assembly of amyloid fibers and selective metal deposition," PNAS, vol. 100(8), pp. 4527-4532. 2003.
Seeman, N.C. "DNA in a material world." Nature, vol. 421, pp. 427-431. 2003.
Rothemund, P.W.K. "Folding DNA to create nanoscale shapes and patterns." Nature, vol. 440, pp. 297-302, 2006.
Castello, A. et al, "Insights into RNA Biology from an Atlas of Mammalian mRNA-Binding Proteins." Cell, vol. 149, pp. 1393-1406. 2012.
Chen, H. et al, "Ionic strength-dependent persistence lengths of single-stranded RNA and DNA." PNAS, vol. 109(3), pp. 799-804. 2012.
Delebecque, C.J. et al. "Organization of Intracellular Reactions with Rationally Designed RNA Assemblies." Science, vol. 333, pp. 470-474, 2011.
Delebecque, C.J. et al. "Supporting Online Material for Organization of Intracellular Reactions with Rationally Designed RNA Assemblies." Science, vol. 333, S1-S27. 2011.
Ding, Y. et al. "Sfold web server for statistical folding and rational design of nucleic acids." Nucleic Acids Research, vol. 32, W135-W141. 2004.
Geary, C. et al. "A single-stranded architecture for cotranscriptional folding of RNA nanostructures." Science, vol. 345, pp. 799-804. 2014.
Gohlke, C. et al. "Kinking of DNA and RNA helices by bulged nucleotides observed by fluorescence resonance energy transfer." Proc. Natl. Acad. Sci., vol. 91, pp. 11660-11664. 1994.
Hochrein, L.M. et al. "Conditional Dicer Substrate Formation via Shape and Sequence Transduction with Small Conditional RNAs, Journal of the American Cancer Society, vol. 135, pp. 17322-17330. 2013.
Kahan, M. et al. "Towards molecular computers that operate in a biological environment." Physica D, vol. 237, pp. 1165-1172. 2008.
Kertesz, M. et al. "Genome-wide Measurement of RNA Secondary Structure in Yeast." Nature. vol. 467, pp. 103-107, 2010.
Lu, J. et al. "Iron-binding activity of human iron-sulfur cluster assembly protein hIscA1." Biochem. vol. 428, pp. 125-131. 2010.
Mizukoshi, T. et al. "Structural study of DNA duplexes containing the (6-4) photoproduct by fluorescence resonance of transfer." Nucleic Acids Research, vol. 29(24), pp. 4948-4954. 2001.
Pettersen, E.F. et al. "UCSF Chimera—A Visualization System for Exploratory Research and Analysis." J. Comput. Chem, vol. 25, pp. 1605-1612. 2004.
Rapaport, D.C. "The art of molecular dynamics simulation," Cambridge University Press. 2004. 13 pgs.
Scherer, L.J. "Optimization and characterization of tRNA-shRNA expression constructs." Nucleic Acids Research, vol. 35(8), pp. 2620-2628. 2007.
Srinivas, N. et al. "On the biophysics and kinetics of toehold-mediated DNA strand displacement." Nucleic Acids Research, vol. 41(22), pp. 10641-10658. 2013.
Tan R. et al, "Structural variety of arginine-rich RNA-binding peptides." Proc. Natl. Acad. Sci. vol. 92, pp. 5282-5286. 1995.
Watts, J.M. et al, "Architecture and Secondary Structure of an Entire HIV-1 RNA Genome." Nature, vol. 460, pp. 711-716. 2009.
Zhang, D. Y. "Dynamic DNA nanotechnology using strand-displacement reactions." Nature, vol. 3, pp. 103-113. 2011.
Zhang, F. et al. "Structureal DNA Nanotechnology: State of the Art and Future Perspective." Journal of the American Chemical Society, vol. 136, pp. 11198-11211. 2014.
Dreyfuss, G. et al. "Messenger-RNA-binding proteins and the messages they carry." Nat. Rev. Mol. Cell Biol., vol. 3, pp. 195-205. 2002.
Yusupov, M. M., et al. "Crystal structure of the ribosome at 5.5 A resolution." Science, vol. 292, pp. 883-896. 2001.
Douglas, S. M., et al. "A Logic-Gated Nanorobot for Targeted Transport of Molecular Payloads." Science, vol. 335, pp. 831-834. 2012.
Green, L. S., et al. "Inhibitory DNA Ligands to Platelet-Derived Growth Factor B-Chain." *Biochemistry* vol. 35, pp. 14413-14424, (1996).
Klenberger, F., et al. "Static and Dynamical Properties of Single Poly(Ethylene Glycol) Molecules Investigated by Force Spectrocopy." Single Molecules, vol. 1, pp. 123-128. 2000.
Lilley, D. M. et al. "Fluorescence resonance energy transfer as a structural tool for nucleic acids." Current Opinion in Chemical Biology, vol. 4, pp. 507-517. 2000.
Fürtig, B., et al. "Time Resolved NMR Studies of RNA Folding." Biopolymers, vol. 85, pp. 360-383. 2007.
Varani, G., et al. NMR Investigation of RNA structure. Progress in Nuclear Magnetic Resonance Spectroscopy, vol. 29, pp. 51-127. 1996.
Russell, R. et al. "Small angle X-ray scattering reveals a compact intermediate in RNA folding." Nat Struct Mol Biol, vol. 7, pp. 367-370. 2000.
Lipfert, J. et al. "Small-Angle X-Ray Scattering from RNA, Proteins, and Protein Complexes." Annual Review of Biophysics and Biomolecular Structure. vol. 36, 307-327. 2007.
Takada, S. "Coarse-grained molecular simulations of large biomolecules." Current Opinion in Structural Biology, vol. 22, pp. 130-137. 2012.
Pascal, T. A., et al. "Role of Specific Cations and Water Entropy on the Stability of Branched DNA Motif Structures." The Journal of Physical Chemistry B, vol. 116, pp. 12159-12167. 2012.
Sim, A. Y. L., et al. "Modeling nucleic acids." Current Opinion in Structural Biology, vol. 22, pp. 273-278. 2012.
Dragan, A. I. Use of Fluorescence Resonance Energy Transfer (FRET) in Studying Protein-Induced DNA Bending. Methods in Enzymology. vol. 450 (Eds Brand Ludwig & L. Johnson Michael), Chapter 9, pp. 185-199. Academic Press. 2008.
Bassi, G.S. et al. "Ion-Induced folding of the hammerhead ribozyme: a fluorescence resonance energy transfer study." The EMBO Journal, vol. 16, pp. 7481-7489. 1997.
Houseley, J., et al. RNA-quality control by the exosome. Nat Rev Mol Cell Biol, vol. 7, pp. 529-539 2006.
Tinland, B. et al. "Persistence Length of Single-Stranded DNA." Macromolecules, vol. 30, pp. 5763-5765. 1997.
Restriction Requirement issued for U.S. Appl. No. 11/978,219, filed Oct. 26, 2007, filed in the name of Si-Ping Han et al. Mailed on Jun. 4, 2014.
Non-Final Office Action issued for U.S. Appl. No. 11/978,219, filed Oct. 26, 2007 filed in the name of Si-Ping Han et al. Mailed on Sep. 30, 2014.
Notice of Allowance issued for U.S. Appl. No. 14/093,387, filed Nov. 29, 2013 in the name of Si-ping Han et al. Mailed on Jun. 5, 2015.
Notice of Allowability issued for U.S. Appl. No. 14/093,387, filed Nov. 29, 2013 in the name of Si-ping Han et al. Mailed on Jul. 2, 2015.
Final Office Action issued for U.S. Appl. No. 11/978,219, filed Oct. 26, 2007 filed in the name of Si-Ping Han et al. Mailed on Jun. 1, 2015.
Ford, W.E. et al. "Platinated DNA as Precursors to Templated Chains of Metal Nanoparticles." Advanced Materials. vol. 13 (23), pp. 1793-1797. 2001.
Gu, Q. et al. "Cobalt metallization of DNA: toward magnetic nanowires." Nanotechnology, vol. 16, pp. 1358-1363. 2005.
Cai, H. et al. "Electrochemical detection of DNA hybridization based on silver-enhanced gold nanoparticle label." Analytica Chimica Acta, Vo. 469, pp. 165-172. 2002.

Medusa G2 A3 B7

A: INACTIVE

B: ACTIVE

○ RNA
● 2'-O-methyl RNA
★ Inverted dT (exonuclease blocker)
* Phosphorothioate backbone
⌇ C₃ linker
⌇ 3xEG linker
⌇ 6xEG linker

TARGETING DOMAIN AND RELATED SIGNAL ACTIVATED MOLECULAR DELIVERY

CROSS REFERENCE TO RELATED APPLICATIONS

This application is related to U.S. Provisional Application entitled "Pseudoknot construct for signal activated RNA interference" Ser. No. 61/613,617, filed on Mar. 21, 2012, the disclosure of which is incorporated herein by reference in its entirety. The present application might also be related to U.S. application entitled "Signal Activated Molecular Delivery" Ser. No. 13/167,672 filed on Jun. 23, 2011, and to International Application "Signal Activated Molecular Delivery" Serial No. PCT/US11/41703 filed on Jun. 23, 2011, the disclosure of each of which is also incorporated by reference in its entirety.

FIELD

The present disclosure relates to a targeting domain and related signal activated molecular delivery and in particular to signal activatable constructs, and related components, compositions, methods and systems.

BACKGROUND

Molecular delivery has been a challenge in the field of biological molecule analysis, in particular when aimed at obtaining controlled delivery of analytes of interest to specific environments. Whether for medical applications or for fundamental biology studies, several methods are commonly used for the delivery of various classes of biomaterials and biomolecules.

Controlled delivery of targets to specific environments, e.g. specific cell types and/or tissues of individuals in vitro and/or in vivo is currently still challenging, especially when directed at providing controlled release of the target in a controllable conformation, typically associated to a biological activity.

SUMMARY

Provided herein, are a targeting domain and related signal activatable constructs for enzyme-assisted molecular delivery, and related components, compositions, methods and systems. In particular, in several embodiments, signal activatable constructs herein described comprise a targeting domain and activatable molecular complexes and activated complexes suitable for controlled release of a targeting domain, which can comprise molecules of various chemical natures.

According to a first aspect, a targeting domain is described. The targeting domain comprises a targeting domain duplex RNA having a length of about 19 to about 30 bp and comprising a guide strand complementary bound to a passenger strand nicked in two passenger strand segments having from about to 2 bp to about 17 bp length and allowing the targeting domain duplex RNA to adopt a folded conformation and an unfolded conformation. In the folded conformation opposite ends of the targeting domain duplex RNA are in a configuration minimizing processing of the guide strand by dicer and/or an argonaute enzyme. In the unfolded conformation, the opposite ends of the targeting domain duplex RNA are in a configuration allowing processing of the guide strand by dicer and/or an argonaute enzyme.

According to a second aspect, a locking sensor is described for enzyme-assisted molecular delivery of a targeting domain herein described, and related compositions, methods and systems. The locking sensor comprises a locking sensor RNA duplex having a toehold segment a displacement segment, and an activation segment. The locking sensor RNA duplex comprises a first strand presented on displacement segment and a second strand presented on the activation segment and is configured to attach opposite ends of the targeting domain in a folded conformation, through covalent linkage of the first strand with a first end of the opposite ends of the targeting domain and through covalent linkage of the second strand with a second end of the opposite ends of the targeting domain. In the locking sensor herein described, the displacement segment complementarily binds the activation segment and the toehold segment is presented for binding to a signal molecule. In the locking sensor herein described, the targeting domain and the locking sensor are further configured to allow release of the targeting domain from the folded conformation upon binding of the signal molecule to the toehold segment and consequent displacement of the displacement segment from the activation segment.

The composition comprises one or more locking sensors together with a suitable vehicle. The method comprises: contacting the locking sensor herein described with a targeting domain herein described, the contacting performed for a time and under condition to allow covalent attachment of the targeting domain to the first strand and the second strand of the locking sensor in a molecular complex comprising the targeting domain in a folded conformation. The system comprises: a locking sensor and a targeting domain herein described for simultaneous combined or sequential use in the method to provide a molecular complex is described for enzyme-assisted molecular delivery herein described.

According to a third aspect a molecular complex is described for enzyme-assisted molecular delivery, and related compositions methods and systems. The molecular complex comprises a targeting domain herein described and a locking sensor comprising a locking sensor RNA duplex having a toehold segment, a displacement segment and an activation segment. In the molecular complex, opposite ends of the targeting domain covalently bind to the locking sensor through covalent linkage of a first end of the opposite ends of the targeting domain with a first strand of presented on the displacement segment and through covalent linkage of a second end of the opposite ends of the targeting domain with a second strand presented on the activation segment. In the molecular complex, the displacement segment is complementarily bound to the activation segment and the toehold segment is presented for binding to a signal molecule. In the molecular complex, the targeting domain and the locking sensor are configured to allow release of the targeting domain from the folded conformation upon binding of the signal molecule to the toehold segment and consequent displacement of the displacement segment from the activation segment. The composition comprises one or more molecular complexes herein described together with a suitable vehicle. The method comprises: contacting the molecular complex with a signal molecule able to bind to the toehold for a time and under condition to allow release of the targeting domain from the folded conformation to the unfolded conformation. The system comprises: at least two of a molecular complex, and a signal molecule able to bind to the toehold segment of the molecular complex, for simultaneous combined or sequential use to control release of the targeting domain from the folded conformation according to the methods herein described.

According to a fourth aspect, an activatable molecular complex is described and related, activated complexes, compositions methods and systems. The activatable molecular complex comprises: a targeting domain herein described and a locking sensor comprising a toehold segment a displacement segment and an activation segment having at least an RNA portion. In the molecular complex, the targeting domain covalently binds the locking sensor through covalent linkage of a first of opposite ends of the targeting domain with a first strand of presented on the displacement segment and through covalent linkage of a second end of the opposite ends of the targeting domain with a second strand presented on the activation segment. The activatable molecular complex is configured to exhibit a first conformation and a second, activated conformation wherein, in the first conformation the displacement segment complementarily binds the RNA portion of the activation segment to form a locking sensor RNA duplex, and the toehold segment is presented for binding to a signal molecule; and the targeting domain is in a folded conformation. In the second activated conformation, the toehold segment and the displacement segment of the locking sensor either complementary bind a third polynucleotide or are absent, the activation segment of the locking sensor is either presented in a single stranded configuration cleavable by ribonuclease enzymes, or folded to provide an RNAase H binding site presented for binding, or is absent, and the targeting domain is released from the folded conformation.

The composition comprises one or more activatable complexes and a suitable vehicle. The method comprises contacting an activatable molecular complex in a first conformation, with a signal molecule able to bind to the toehold segment of the activatable molecular complex for a time and under condition to allow switching of the molecular complex from the first conformation to the second active conformation. The system comprises at least two of one or more activatable molecular complexes herein described, and a signal molecule capable to bind the toehold segment of the molecular complexes for simultaneous combined or sequential use to control release of the targeting domain from the folded conformation in the molecular complex.

According to fifth aspect, an activated molecular complex is described and related compositions methods and systems. The activated molecular complex comprises a targeting domain herein described and a locking sensor, comprising an activation segment, a displacement segment complementary to the activation segment; and, a toehold segment capable to bind to a signal molecule. In the activated molecular complex the targeting domain is bound in the unfolded conformation to the displacement segment and the activation segment through covalent attachment of one of the opposite ends of the targeting domain to a first strand presented in the displacement segment and a second strand presented on the activation segment, In the activated molecular complex, the displacement segment and the toehold segment either complementary bind a third polynucleotide or are absent, and the targeting domain is in a conformation configured to allow processing by dicer and/or an argonaute enzyme following cleavage of the activation segment from the targeting domain by a suitable ribonuclease.

The related composition comprises one or more activated molecular complexes and a suitable vehicle. The related method to provide the activated molecular complex comprises contacting the activatable molecular complex herein described in the first conformation, with a signal molecule binding to the signal binding portion to allow switching of the molecular complex from the first conformation to the second activated conformation of the molecular complex. The related method for controlled release of a targeting domain from an activated complex comprises: contacting the activated molecular complex with a suitable ribonuclease and with dicer and/or an argonaute enzyme for a time and under condition to allow release of the guide strand from the activated molecular complex.

According to sixth aspect, a method for treating a disease in an individual through RNAase assisted signal activated molecular delivery in cells, is described, and related compositions and systems. The method comprises administering to the individual an effective amount of one or more of the signal activatable constructs as described in the second aspect. The related pharmaceutical composition comprises one or more signal activatable constructs herein described with a pharmaceutical acceptable vehicle.

According to a further aspect, complexes, herein described can be provided by a method comprising providing a polynucleotide guide strand, a polynucleotide A strand and a polynucleotide B strand, wherein the polynucleotide A strand comprises from the 5' end to 3' end the toehold segment, the displacement segment and a first passenger strand segment of the two passenger strand segments of the targeting domain in a 5' to 3' configuration. IN the method the polynucleotide strand B comprises from the 5' end to 3' end a second passenger strand segment of the two passenger strand segments of the targeting domain and the activation segment. The method further comprises contacting the polynucleotide guide strand, the polynucleotide A strand and the polynucleotide B strand for a time and under condition to allow annealing of the strand to form the molecular complex of claim 5.

The constructs, systems, compositions and methods herein described allow in several embodiments to performed cell type specific molecular delivery.

The constructs, systems, compositions and methods herein described also allow in several embodiments integration of signal detection, signal transduction and targeting in a single compact molecular construct with easier delivery and/or administration as well as enhanced efficiency of signal transduction with respect to some approaches of the art.

The constructs, systems, compositions and methods herein described also allow in several embodiments intracellular information processing and controlling in which the presence of one set of biomolecules (e.g. protein or nucleic acid) is coupled with inhibition or activation of another set of biomolecules in the cells.

The methods and systems herein described can be used in connection with applications wherein cell-type specific modulation of cells is desired, including but not limited to medical application, biological analysis, research and diagnostics including but not limited to clinical, therapeutic and pharmaceutical applications, such as cell type specific drug delivery, cell type specific modeling or therapy, including but not limited to gene therapy and RNAi.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and examples sections, serve to explain the principles and implementations of the disclosure.

1A), an open active conformation (FIG. 1B) and a folded inactive conformation (FIG. 1C)

Figure 2:
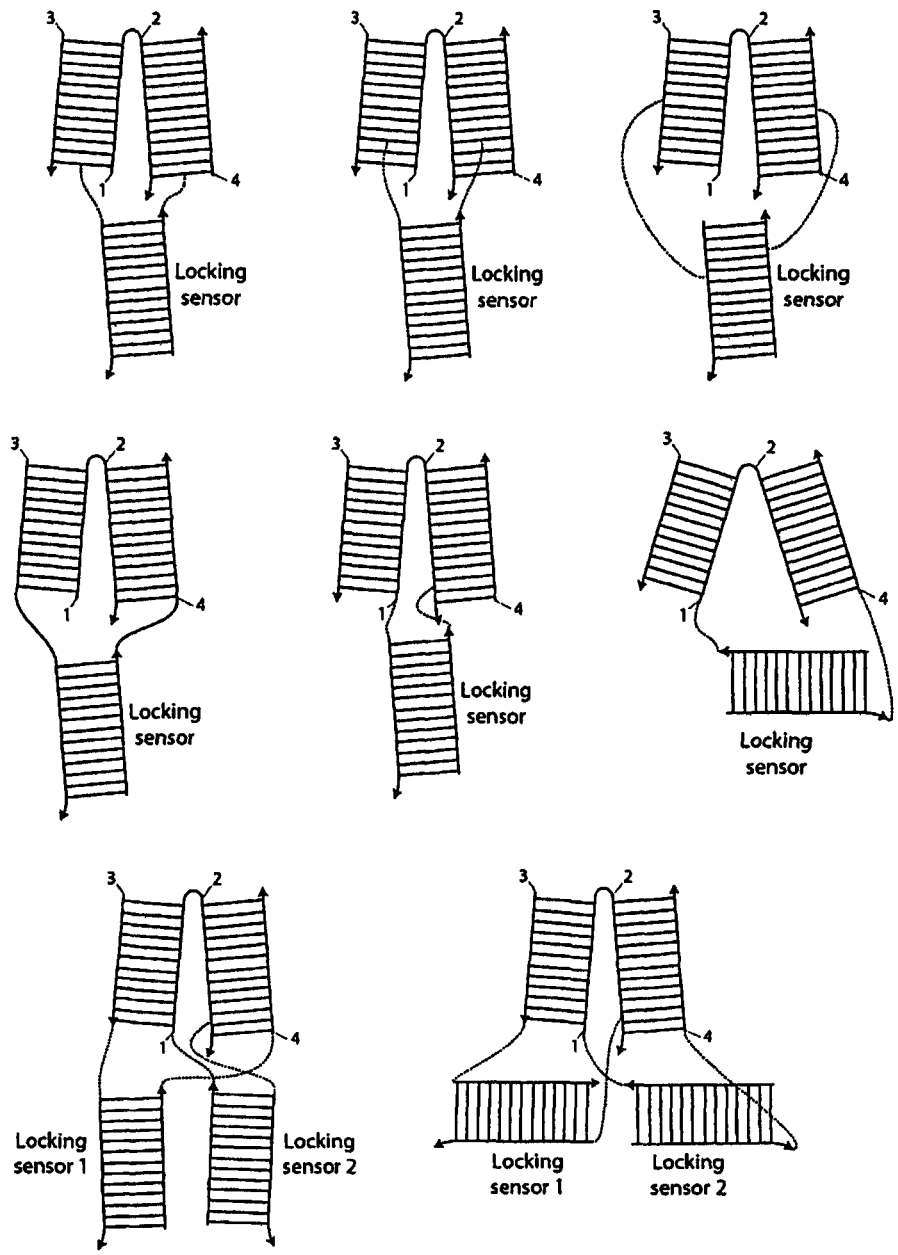

FIG. 2 shows a schematic illustration of molecular complexes herein described showing exemplary attachments of the locking sensor to the targeting domain having segments 1, 2, 3 and 4 according to embodiments herein described.

Figure 3:
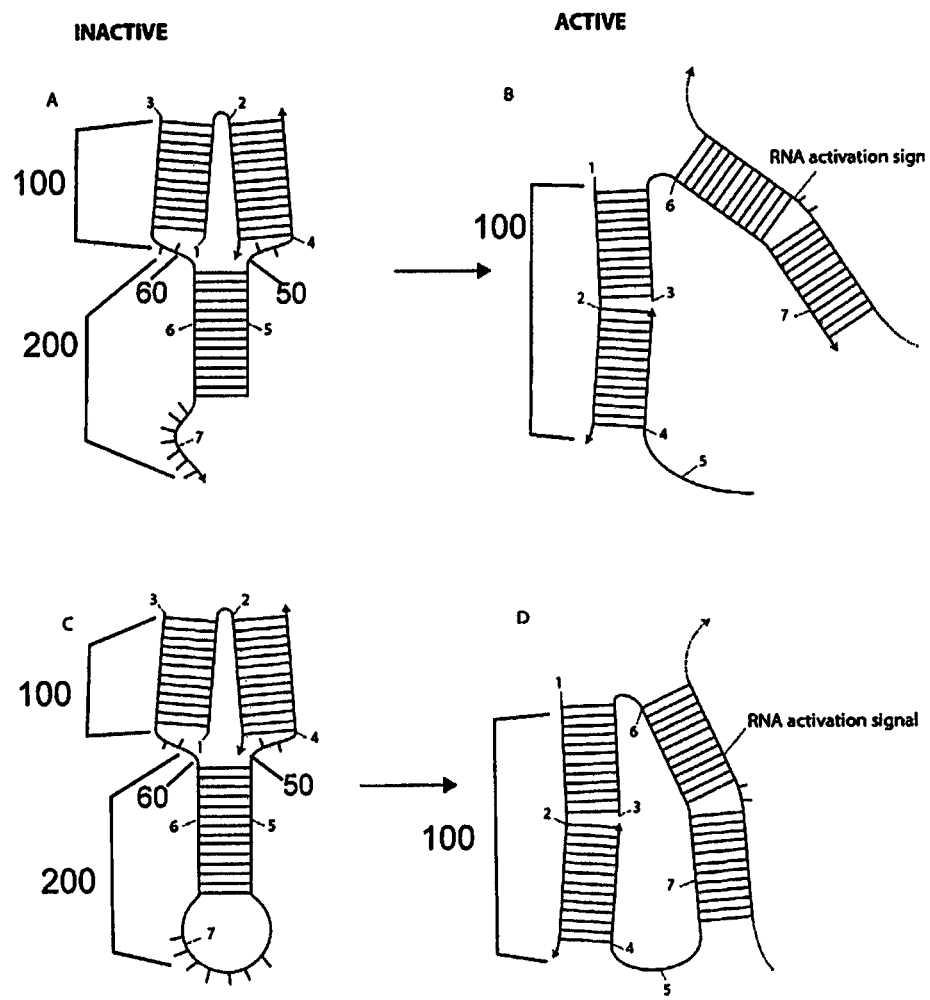

FIG. 3 shows a schematic illustration of exemplary activatable molecule complexes herein described inclusive of segments 1, 2, 3, 4, 5, 6 and 7, shown in an inactive conformation (FIG. 3A and FIG. 3C) and active conformation (FIG. 3B and FIG. 3D). In the illustration of FIG. 3, the correspondence between active and inactive form is indicated by arrows.

Figure 4:
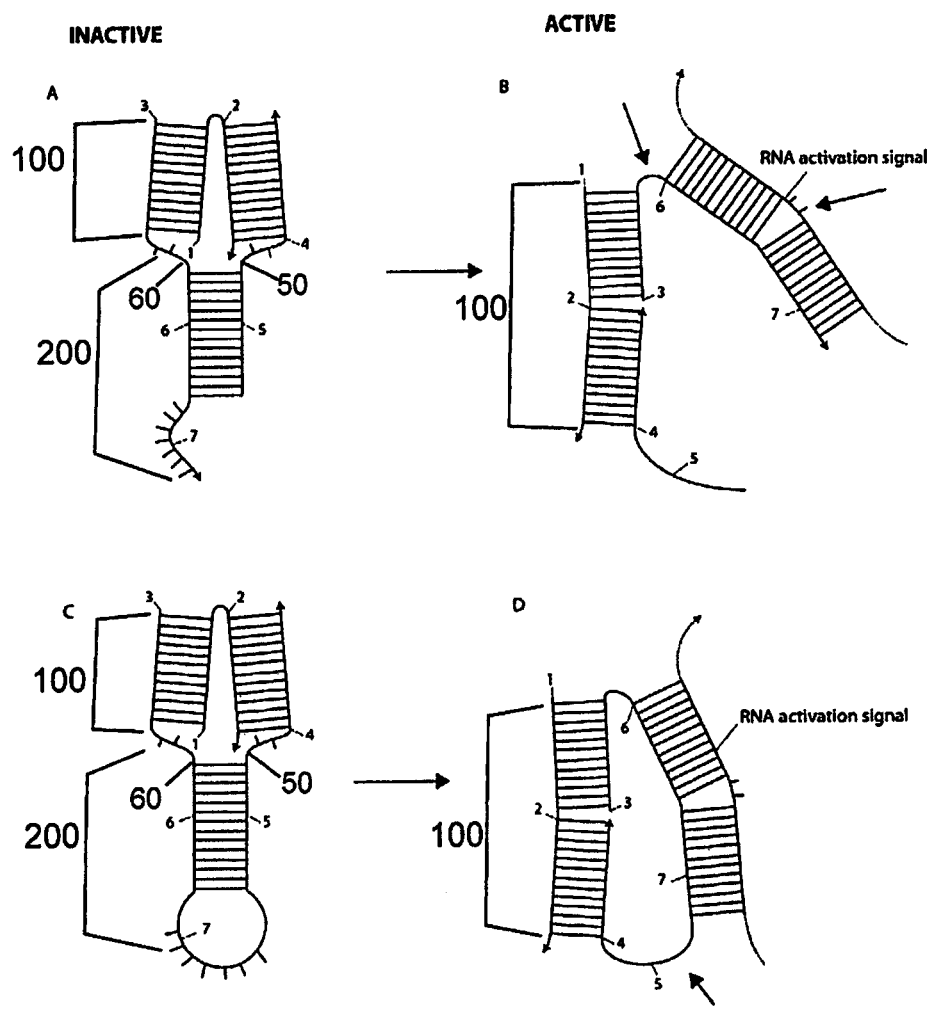

FIG. 4 illustrates the exemplary activatable molecule complexes of FIG. 3 inclusive of segments 1, 2, 3, 4, 5, 6 and 7, with arrows indicating unstructured regions minimizing activation of the PKR pathway.

Figure 5:
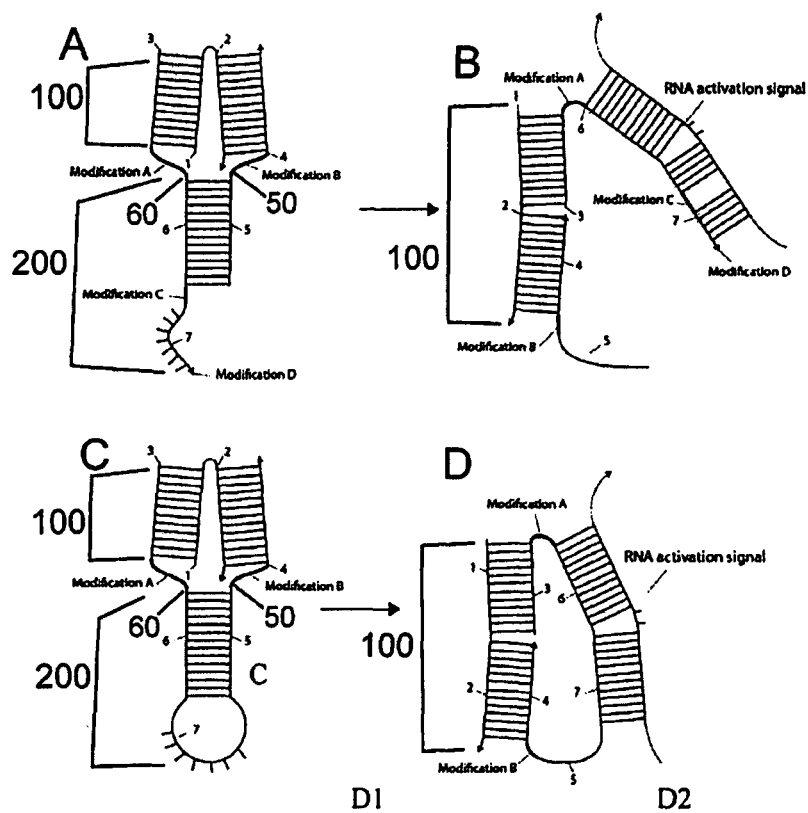

FIG. 5 shows exemplary sites of exemplary chemical modification of molecular complexes herein described inclusive of segments 1, 2, 3, 4, 5, 6, and 7 illustrated with reference to the exemplary activatable molecule complexes of FIG. 3.

Figure 6:
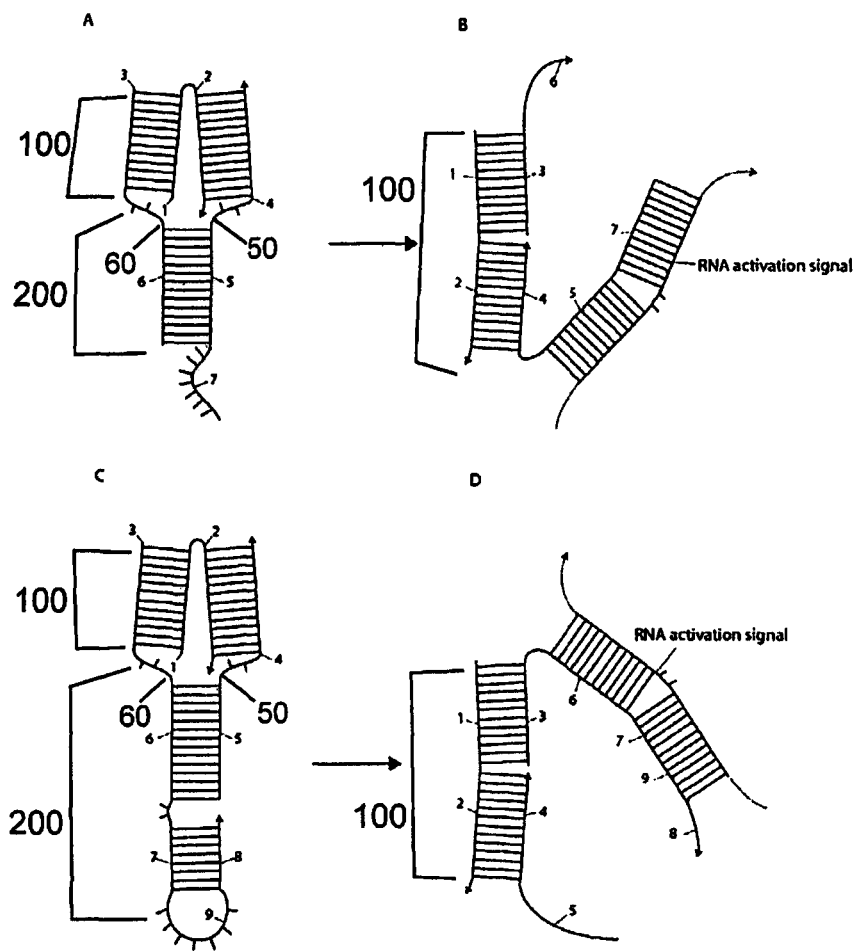

FIG. 6 shows exemplary configuration of activatable molecule complexes herein described inclusive of segments 1, 2, 3, 4, 5, 6, 7, 8 and 9, illustrated as variant geometry with respect to the activatable molecule complexes of FIG. 3.

Figure 7:
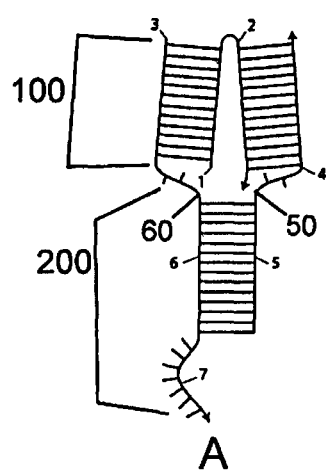
Figure 7:
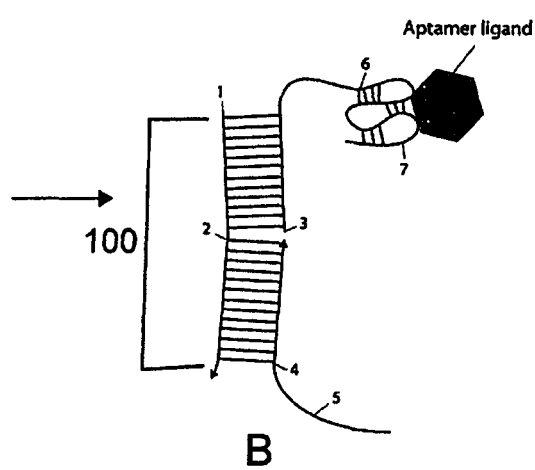
Figure 7:
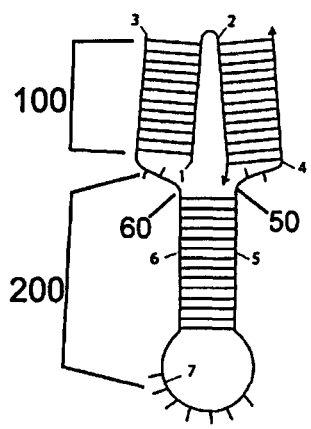
Figure 7:
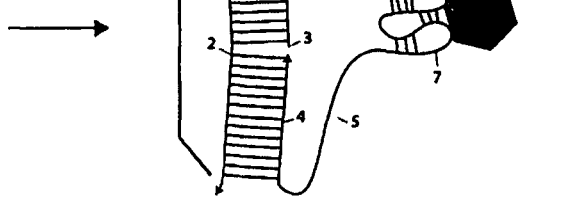

FIG. 7 shows exemplary targeting domain herein described in a folded conformation covalently linked to exemplary locking sensors herein described (FIG. 7A and FIG. 7C) and in an folded conformation following binding of an exemplary signal molecule (FIG. 7B and FIG. 7D). In the illustration of FIG. 7, segments of the constructs are indicated with the numbers 1, 2, 3, 4, 5, 6 and 7, and the correspondence between active and inactive form is indicated by arrows.

Figure 8:
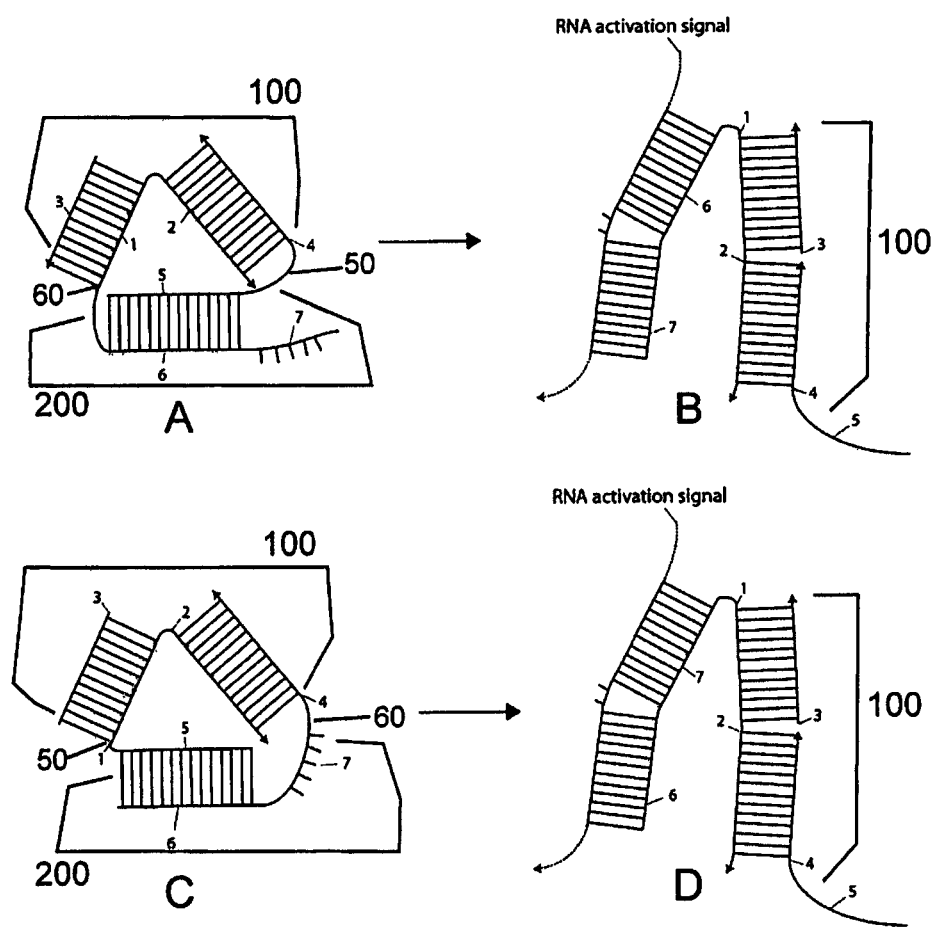

FIG. 8 shows exemplary targeting domain herein described in a folded conformation covalently linked to exemplary locking sensors herein described (FIG. 8A and FIG. 8C) and in a folded conformation following binding of an exemplary signal molecule (FIG. 8B and FIG. 8D). In the illustration of FIG. 8, segments of the constructs are indicated with the numbers 1, 2, 3, 4, 5, 6 and 7, and the correspondence between active and inactive form is indicated by arrows.

Figure 9:
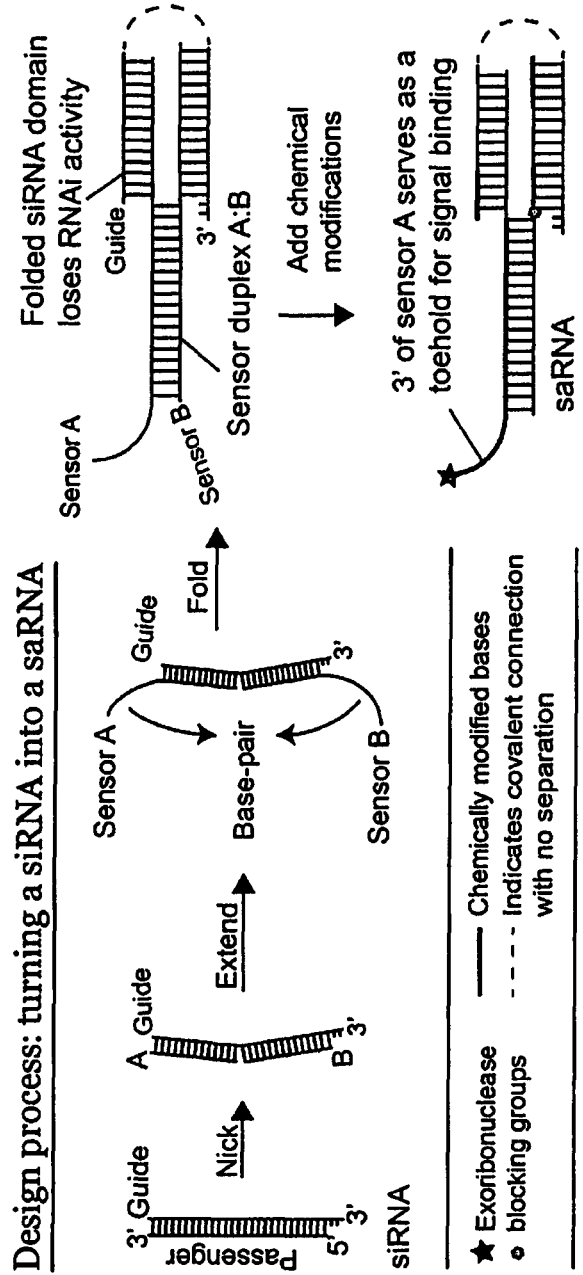

FIG. 9 shows a schematic representation of an exemplary method to provide an exemplary targeting domain in a molecular complex according to embodiments herein described.

Figure 10:
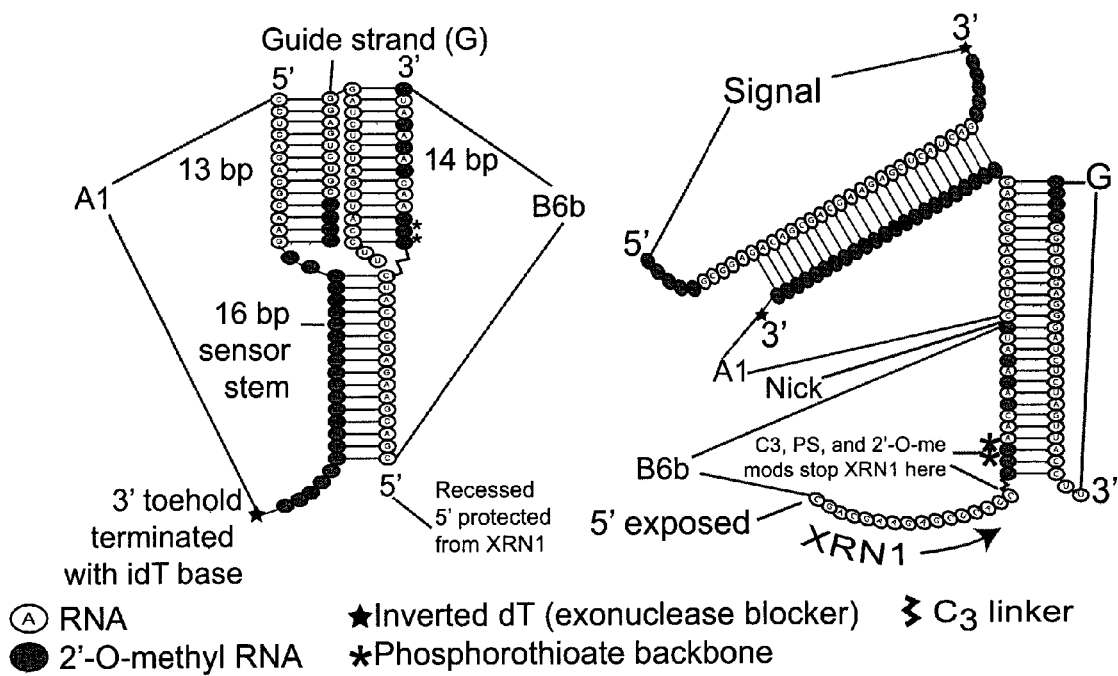

FIG. 10 shows a schematic representation of an exemplary molecular complex herein described wherein the locking sensor comprises a signal binding portion configured to release the targeting domain from the folded conformation Medusa G A1 B6b (SEQ ID NO: 1, SEQ ID NO: 5, SEQ ID NO: 8, and SEQ ID NO: 9) (FIG. 10, panel A) to an unfolded conformation (SEQ ID NO: 1, SEQ ID NO:5, SEQ NO: 8, SEQ NO: 9, and SEQ NO: 16) (FIG. 10, panel B) through displacement of the signal binding portion following binding of a polynucleotide signal, to provide a molecular presenting an activation segment and in an active conformation following processing of the activation segment by a ribonuclease enzyme. Strands A1 (SEQ ID NO: 5), G (SEQ ID NO: 1) and B6b (SEQ ID NO: 8, and SEQ ID NO: 9) of the Medusa complex G A1 B6b (SEQ ID NO: 1, SEQ ID NO: 5, SEQ ID NO: 8, and SEQ ID NO: 9) are indicated in the schematic illustration of the complex in an INACTIVE conformation (Panel A:INACTIVE) and in an ACTIVE conformation (Panel B:ACTIVE).

FIG. 11 shows a schematic representation of an exemplary method to release an exemplary targeting domain from the exemplary molecular complex of FIG. 10.

FIG. 12 shows a schematic illustration of an exemplary molecular complex, Medusa G A2B6b (SEQ ID NO: 1, SEQ ID NO: 48 (5'-C C U C A G A C G C A mA mG-3'), SEQ ID NO: 49(5'-G A U G A G C U C U U C G U C G C U G U C U C-3'), SEQ ID NO: 8, and SEQ ID 9). In particular, FIG. 12, panel A shows the inactive conformation and FIG. 12, panel B shows the active conformation (SEQ ID NO: 1, SEQ ID NO: 48, SEQ ID NO: 49, SEQ NO: 8, SEQ NO: 9, and SEQ NO: 16). Strands A2 (SEQ ID NO: 48, and SEQ ID NO: 49), G (SEQ ID NO: 1) and B6b (SEQ ID NO: 8, and SEQ ID NO: 9) of the Medusa complex GA2 B6b (SEQ ID NO: 1, SEQ ID NO: 48, SEQ ID NO: 49, SEQ ID NO: 8, and SEQ ID 9) are indicated in the schematic illustration of the complex in an INACTIVE conformation (Panel A:INACTIVE) and in an ACTIVE conformation (Panel B:ACTIVE).

FIG. 13 shows a schematic illustration of an exemplary molecular complex, Medusa GA1B6b. In particular, FIG. 13, panel A shows the inactive conformation (SEQ ID NO: 1, SEQ ID NO: 5, SEQ ID NO: 8, and SEQ ID NO:9) and FIG. 13, panel B shows the active conformation (SEQ ID NO: 1, SEQ ID NO: 5, SEQ ID NO: 8, SEQ ID NO: 9 and SEQ ID NO: 16). Strands A1 (SEQ ID NO: 5), G (SEQ ID NO: 1) and B6b (SEQ ID NO: 8, and SEQ ID NO: 9) of the Medusa complex G A1 B6b are indicated in the schematics of illustration of the complex in an INACTIVE conformation (Panel A:INACTIVE) and in an ACTIVE conformation (Panel B:ACTIVE).

FIG. 14 shows a schematic illustration of an exemplary molecular complex, Medusa G2A3B7. In particular, FIG. 14, panel A shows the inactive conformation (SEQ ID NO: 10, SEQ ID NO: 11, SEQ ID NO: 12, SEQ ID NO: 13, SEQ ID NO: 14, and SEQ ID 15) and FIG. 14, panel B shows the active conformation (SEQ ID NO: 10, SEQ ID NO: 11, SEQ ID NO: 12, SEQ ID NO: 13, SEQ ID NO: 14, SEQ ID NO: 15 and SEQ ID NO: 50 (5'-mA mA mA mA mA G C G G A G A C A G C G A C G A A G A G C U C A U C G mA mA mA mA mA T-3')) Strands A3 (SEQ ID NO: 11, SEQ ID NO: 12, and SEQ ID NO: 13), G2 (SEQ ID NO: 10) and B7 (SEQ ID NO: 14, and SEQ ID NO: 15) of the Medusa complex G2 A1 B7 are indicated in the schematic illustration of the complex in an INACTIVE conformation (Panel A:INACTIVE) and in an ACTIVE conformation (Panel B:ACTIVE).

FIG. 15 shows a schematic illustration of an exemplary molecular complex G A1 B4 (SEQ ID NO: 1, SEQ ID NO: 5, and SEQ ID NO: 7) with an activation segment for RNAase H processing. In particular, FIG. 15, panel A shows the inactive conformation (SEQ ID NO: 1, SEQ ID NO: 5, and SEQ ID NO: 7) and FIG. 15, panel B shows the active conformation (SEQ ID NO: 1, SEQ ID NO: 51 (5'-mA mA mG mG mU C C C T G A T C G A C G A A G A G C U C A U C A G G G U A A C mU A mG A mG A U mC C C U C A G A C G C A A G mC mU mG mA mU mG mA mG mC mU mC mU mU mC mG mU mC mG mC mU mG mU mU T-3') and SEQ ID NO: 16).). Strands A1 (SEQ ID NO: 5), G (SEQ ID NO: 1) and B4 (SEQ ID NO: 7,) of the Medusa complex G A1 B4 (SEQ ID NO: 1, SEQ ID NO: 5, and SEQ ID NO: 7) are indicated in the schematics of illustration of the complex in an INACTIVE conformation (Panel A:INACTIVE) and in an ACTIVE conformation (Panel B:ACTIVE).

FIG. 16 shows a schematic representation of an exemplary method to release an exemplary targeting domain from the exemplary molecular complex of FIG. 15.

FIG. 17 shows schematic illustration of exemplary molecular complexes. In particular, molecular complex GA1B1 (SEQ ID NO: 1, SEQ ID NO: 5, and SEQ ID NO: 6) is depicted in FIG. 17, panel A and complex GA1B4 (SEQ ID NO: 1, SEQ ID NO: 52 (5' mA mA mG mG mU C C C T G A

Figure 17:
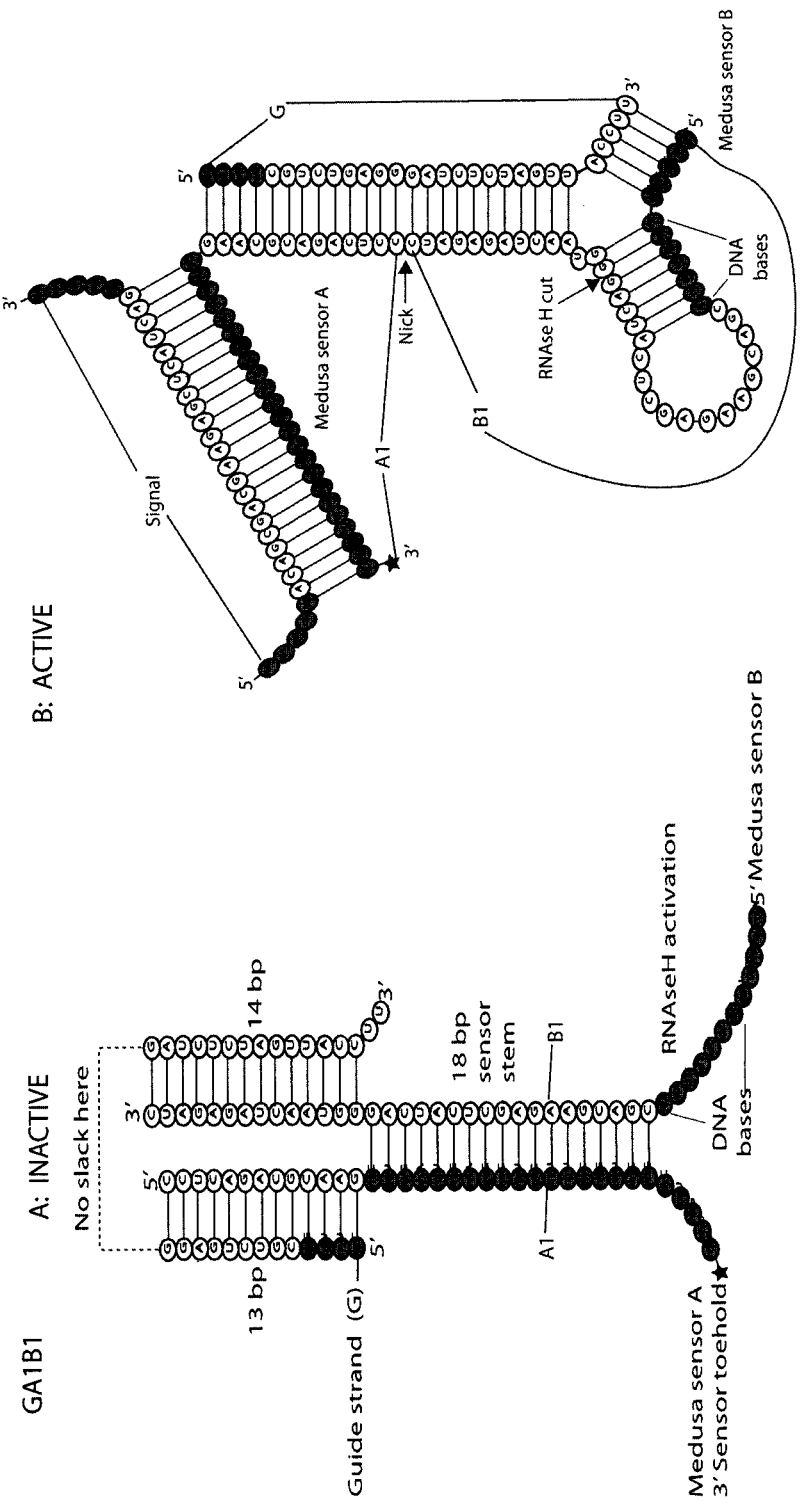

T C G A C G A A G A G C U C A U C A G G G U A A C U A G A G A U C C C U C A G A C G C A A G mC mU mG mA mU mG mA mG mC mU mG mC mU mU mC mG mU mC mG mC mU mG mU mU T-3') and SEQ ID NO: 16) is depicted FIG. 17, panel B.

Figure 18:
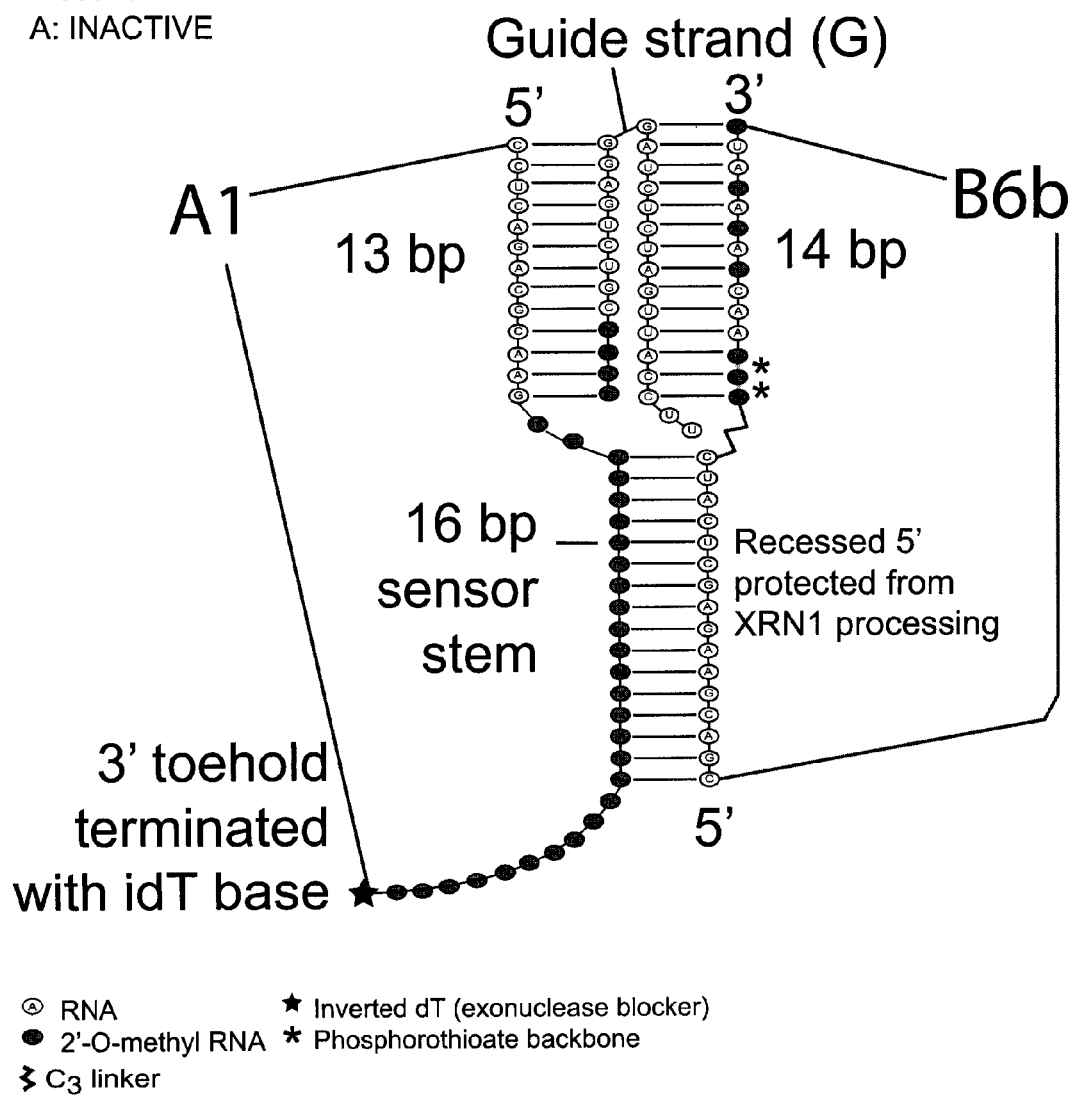

FIG. 18 shows a schematic illustration of an exemplary molecular complex complex G A1 B6b (SEQ ID NO: 1, SEQ ID NO: 5, SEQ ID NO: 8, and SEQ ID NO: 9) in an inactive conformation. Strands A1 (SEQ ID NO: 5), G (SEQ ID NO: 1) and B6b (SEQ ID NO: 8, and SEQ ID NO: 9) of the Medusa complex G A1 B6b (SEQ ID NO: 1, SEQ ID NO: 5, SEQ ID NO: 8, and SEQ ID NO: 9) are indicated in the schematics of illustration of the complex in an INACTIVE conformation (A: INACTIVE)

Figure 19:
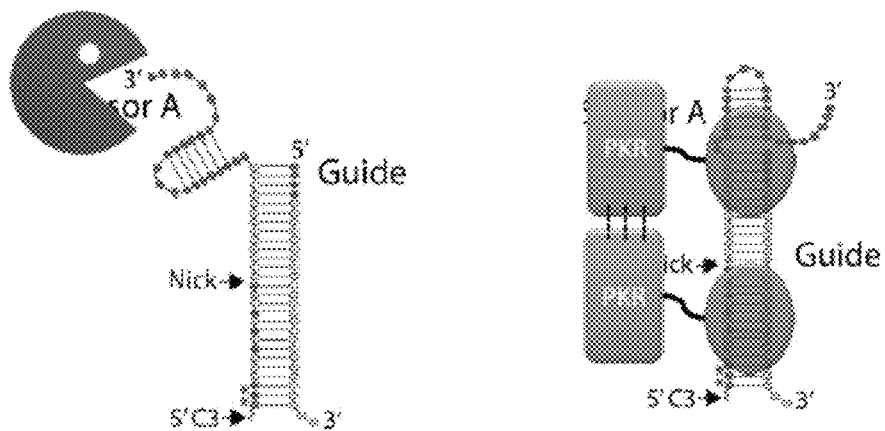

FIG. 19 shows a schematic representation of potential interactions that can lower RNAi activity. In particular, FIG. 19, panel A illustrates exosome interactions and FIG. 19, panel B illustrates PKR interactions (SEQ ID NO: 1, SEQ ID NO: 15, and SEQ ID NO:5).

Figure 20:
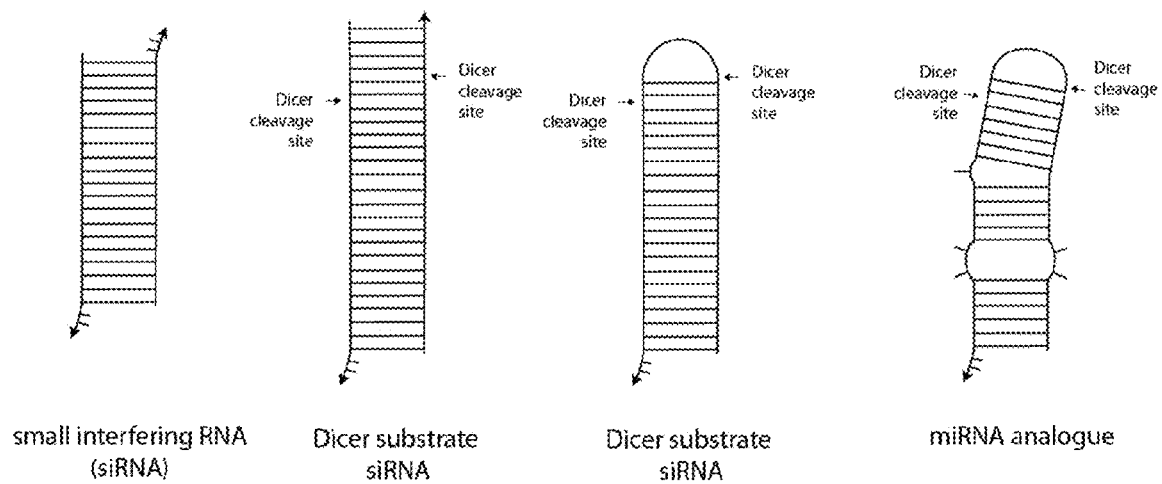

FIG. 20 shows a schematic illustration of a siRNA (FIG. 20, panel A), a Dicer substrate siRNA (FIG. 20, panel B and FIG. 20, panel C), and a miRNA analogue with Dicer cleavage sites (FIG. 20, panel C).

Figure 21:
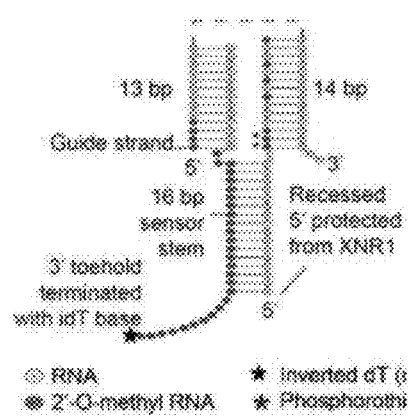
Figure 21:
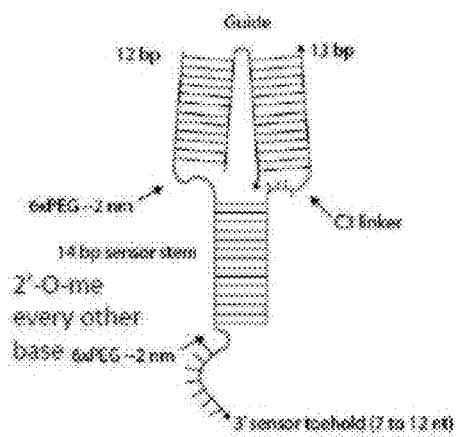

FIG. 21 shows schematic illustration of exemplary molecular complexes. In particular, molecular complex G1A1B6b (SEQ ID NO: 1, SEQ ID NO: 5, SEQ ID NO: 8, and SEQ ID NO: 9) is depicted in FIG. 21, panel A and complex G2A3B7 is depicted FIG. 21, panel B.

Figure 22:
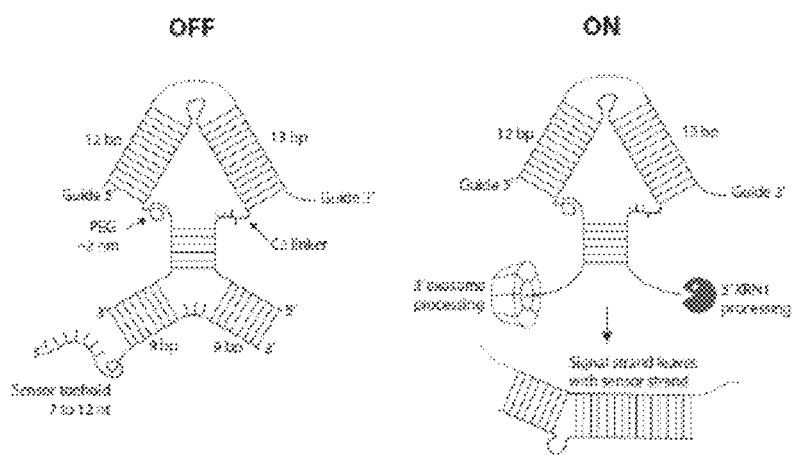
Figure 23:
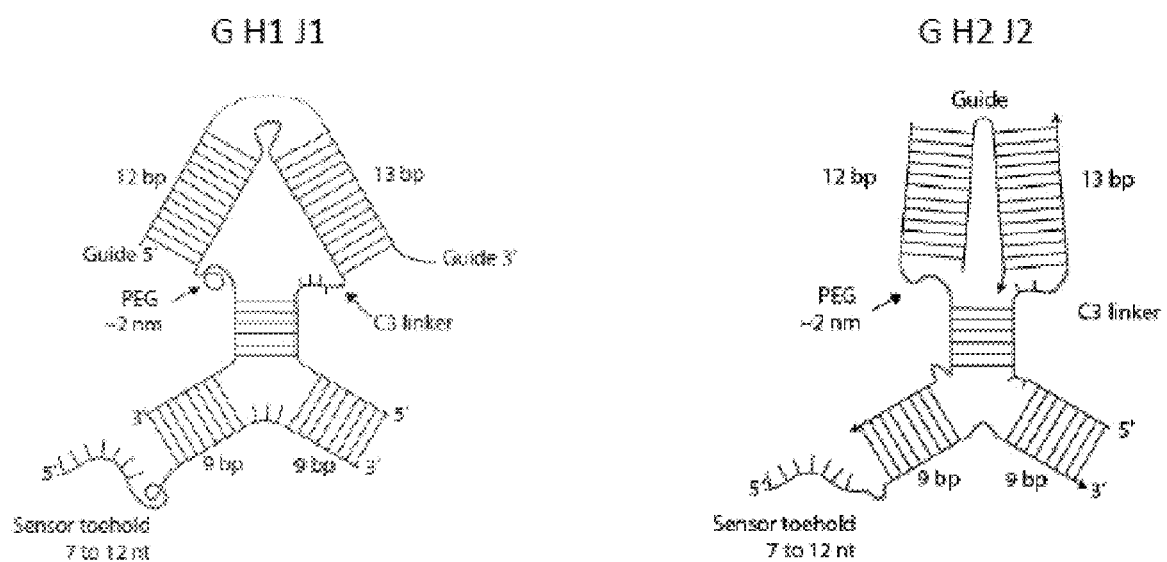

FIG. 22 shows schematic illustration of an exemplary molecular complex with a fall-away sensor. In particular, FIG. 22, panel A shows the "OFF" conformation and FIG. 22, panel B shows the "ON" conformation FIG. 23 shows schematic illustration of exemplary molecular complexes with a fall-away sensor. In particular, molecular complex GH1J1 is depicted in FIG. 23, panel A and complex GH2J2 is depicted FIG. 23, panel B.

Figure 24:
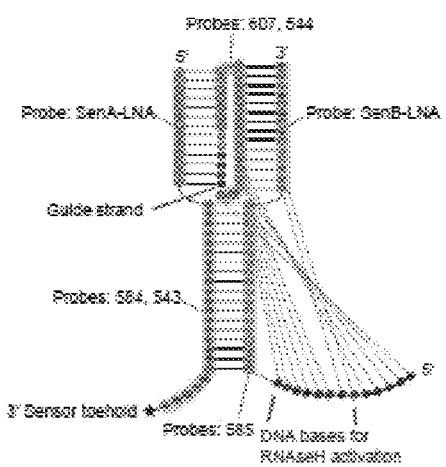
Figure 24:
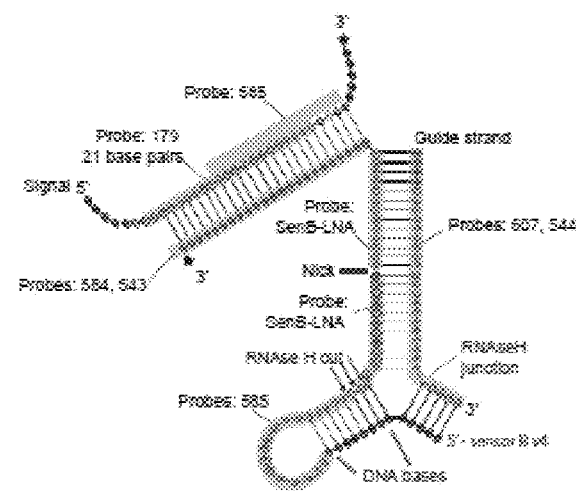

FIG. 24 shows a schematic illustration of an exemplary molecular complex, Medusa RNAseH: GA1B4(S) (SEQ ID NO: 1, SEQ ID NO: 5, and SEQ ID NO: 7). In particular, FIG. 24, panel A shows the inactive conformation (SEQ ID NO: 1, SEQ ID NO: 5, and SEQ ID NO: 7) and FIG. 24, panel B shows the active conformation (SEQ ID NO: 1, SEQ ID NO: 51 and SEQ ID NO: 16). In the schematic illustration of FIG. 24 the segments of the molecular complex corresponding to Probe: SenA-LNA, ProbeS 607, 544, Probe SenB-LNA, Probes 584, 543, Probe 585 and Probe 179, are shown where indicated in the INACTIVE (left) and/or ACTIVE (right) conformations of the complex.

Figure 25:
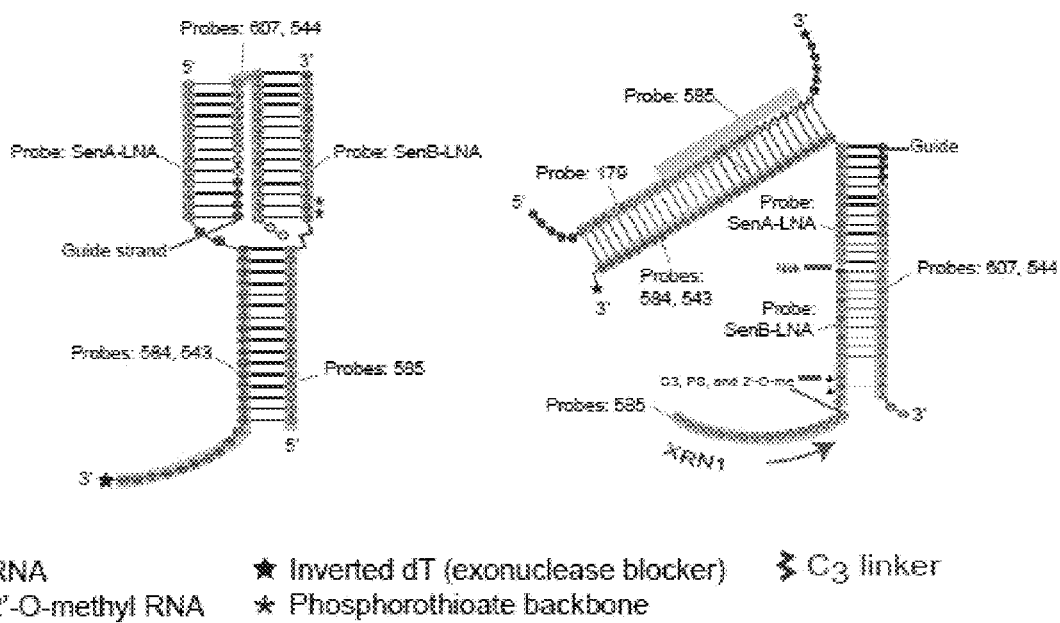

FIG. 25 shows a schematic illustration of an exemplary molecular complex, Medusa Xrna1: GA1B6b(S) (SEQ ID NO: 1, SEQ ID NO: 5, SEQ ID NO: 8, SEQ ID NO: 9 and SEQ ID NO: 16). In particular, FIG. 25, panel A shows the inactive conformation (SEQ ID NO: 1, SEQ ID NO: 5, SEQ ID NO: 8, and SEQ ID NO: 9) and FIG. 25, panel B shows the active conformation (SEQ ID NO: 1, SEQ ID NO: 5, SEQ ID NO: 8, SEQ ID NO: 9 and SEQ ID NO: 16). In the schematic illustration of FIG. 25 the segments of the molecular complex corresponding to Probe: SenA-LNA, Probes 607, 544, Probe SenB-LNA, Probes 584, 543, Probe 585 and Probe 179, are shown where indicated in the INACTIVE (left) and/or ACTIVE (right) conformations of the complex.

Figure 26:
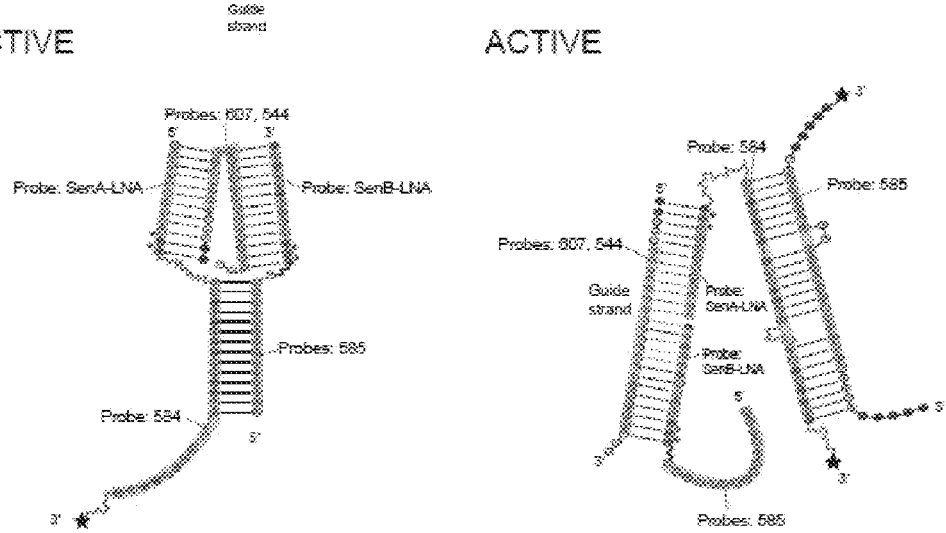

FIG. 26 shows a schematic illustration of an exemplary molecular complex, Medusa Xrna1: G2A3B7 (SEQ ID NO: 10, SEQ ID NO: 11, SEQ ID NO: 12, SEQ ID NO: 13, SEQ ID NO: 14, and SEQ ID NO: 15). In particular, FIG. 26, panel A shows the inactive conformation (SEQ ID NO: 10, SEQ ID NO: 11, SEQ ID NO: 12, SEQ ID NO: 13, SEQ ID NO: 14, and SEQ ID NO: 15) and FIG. 26, panel B shows the active conformation (SEQ ID NO: 10, SEQ ID NO: 11, SEQ ID NO: 12, SEQ ID NO: 13, SEQ ID NO: 14, and SEQ ID NO: 15 and SEQ ID NO: 50). EG indicates Ethylene Glycol. In the schematic illustration of FIG. 26 the segments of the molecular complex corresponding to Probe: SenA-LNA, Probes 607, 544, Probe SenB-LNA, Probes 584, and Probe 585, are shown where indicated in the INACTIVE (left) and ACTIVE (right) conformations of the complex.

Figure 27:
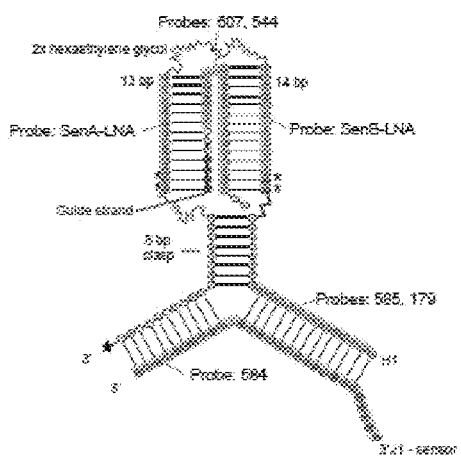
Figure 27:
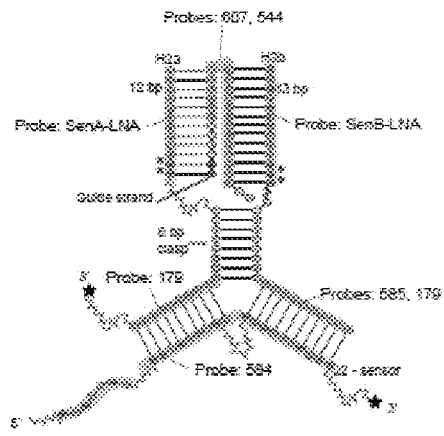

FIG. 27 shows a schematic illustration of an exemplary molecular complex with a fall-away sensor. In particular, FIG. 27, panel A shows an example (G H1 J1 (SEQ ID NO: 1, SEQ ID NO: 20, SEQ ID NO: 21, SEQ ID NO: 22, SEQ ID NO: 23, and SEQ ID NO: 53(5' mC U mG A mU G mA G mC U mC U mU C mG U mC G mC U mG mU mC mU mG mC mG mC 3') with a J1 sensor (SEQ ID NO: 53) and FIG. 27, panel B shows an example (G2 H2 J2 (SEQ ID NO: 10, H2 (H2a: SEQ ID NO: 54 (5' C C C U C A G A C G mC mG 3') SEQ ID NO: 55(5' G C A G A G C G A C G A A G A G C)) and (H2b: SEQ ID NO: 56 (5' G G A G A C A G C G C G C U C U G C A 3') SEQ ID NO: 57(5' mG mG mU A A C mU A mG A mG A mU 3')) with a J2 sensor (SEQ ID NO: 26, SEQ ID NO: 27, and SEQ ID NO: 28). EG indicates Ethylene Glycol. In the schematic illustration of FIG. 27 the segments of the molecular complex corresponding to Probe: SenA-LNA, Probes 607, 544, Probe SenB-LNA, Probes 584, 543, Probe 585 and Probe 179, are shown where indicated in the INACTIVE (left) and/or ACTIVE (right) conformations of the complex.

Figure 28:
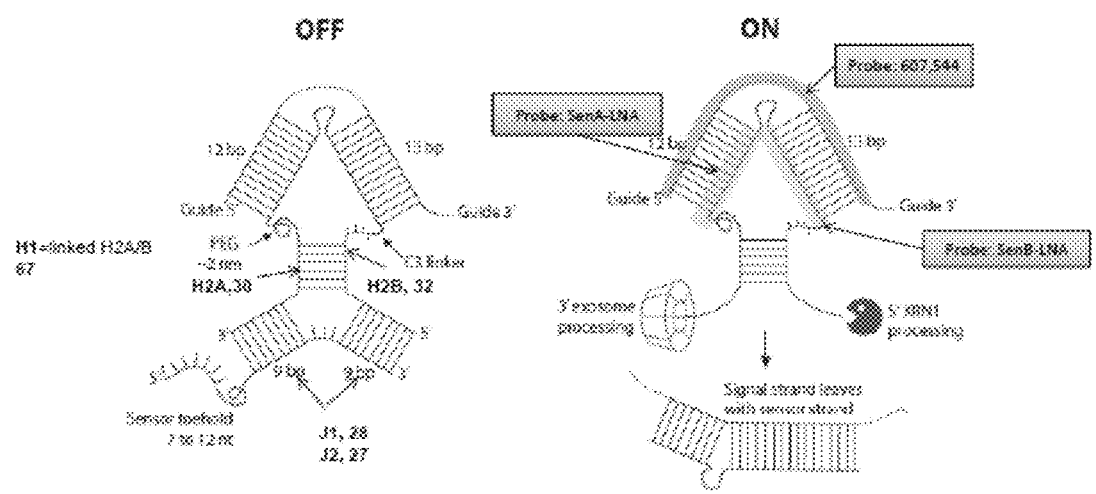

FIG. 28 shows a schematic illustration of an exemplary molecular complex with a fall-away sensor. In particular, FIG. 28, panel A shows the "OFF" conformation and FIG. 28, panel B shows the "ON" conformation.

Figure 29:
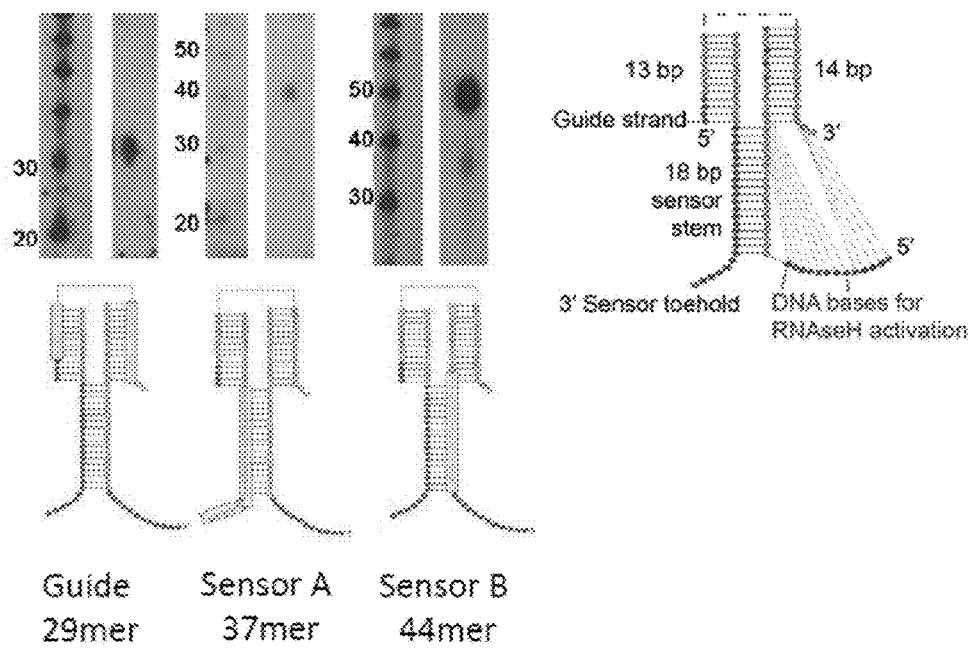

FIG. 29 shows the stability of individual segments of an exemplary complex the Guide (SEQ ID NO: 1), the Sensor A (SEQ ID NO: 5), and the Sensor B (SEQ ID NO: 6). In particular, FIG. 29, panel B shows the schematic of an exemplary complex, and FIG. 29, panel A shows visualized gels of the individual segments next to ladders (marked).

Figure 30:
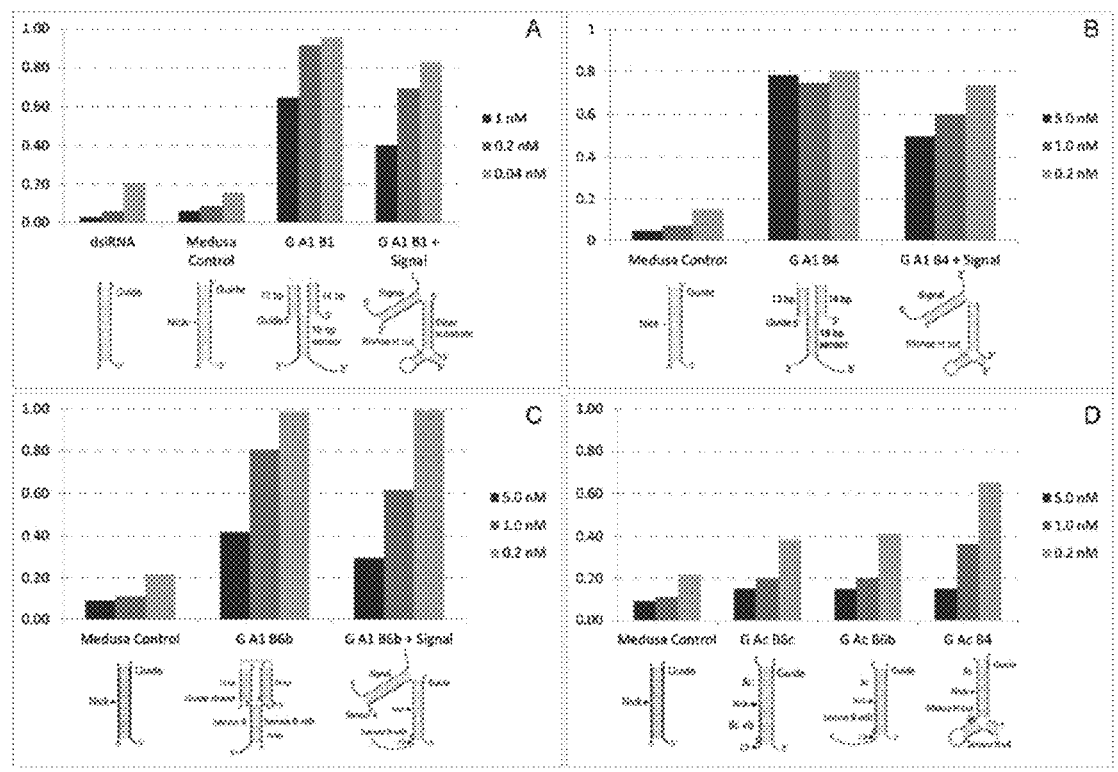

FIG. 30 shows a luciferase assay of exemplary Medusa complexes G A1 B1 (SEQ ID NO: 1, SEQ ID NO: 5, SEQ ID NO: 6), G A1 B1 plus signal (SEQ ID NO: 1, SEQ ID NO: 51 and SEQ ID NO: 16), G A1 B4 (SEQ ID NO: 1, SEQ ID NO: 5, SEQ ID NO:7), G A1 B4 plus signal (SEQ ID NO: 1, SEQ ID NO: 50 and SEQ ID NO: 16), G A1 B6b (SEQ ID NO: 1, SEQ ID NO: 5, SEQ ID NO: 8, and SEQ ID NO: 9), G A1 B6b plus signal (SEQ ID NO: 1, SEQ ID NO: 5, SEQ ID NO: 8, SEQ ID NO: 9 and SEQ ID NO: 16), G Ac B6c (SEQ ID NO: 1, SEQ ID NO: 2, and SEQ ID NO: 18), G Ac B6b (SEQ ID NO: 1, SEQ ID NO: 2, SEQ ID NO: 8 and SEQ ID NO: 9), and G Ac B4 (SEQ ID NO: 1, SEQ ID NO: 57) with controls where the y-axis represents relative luciferase units and x-axis represents the exemplary complexes used in the assay. Panels A, B, C, and D represent different luciferase assays.

Figure 31:
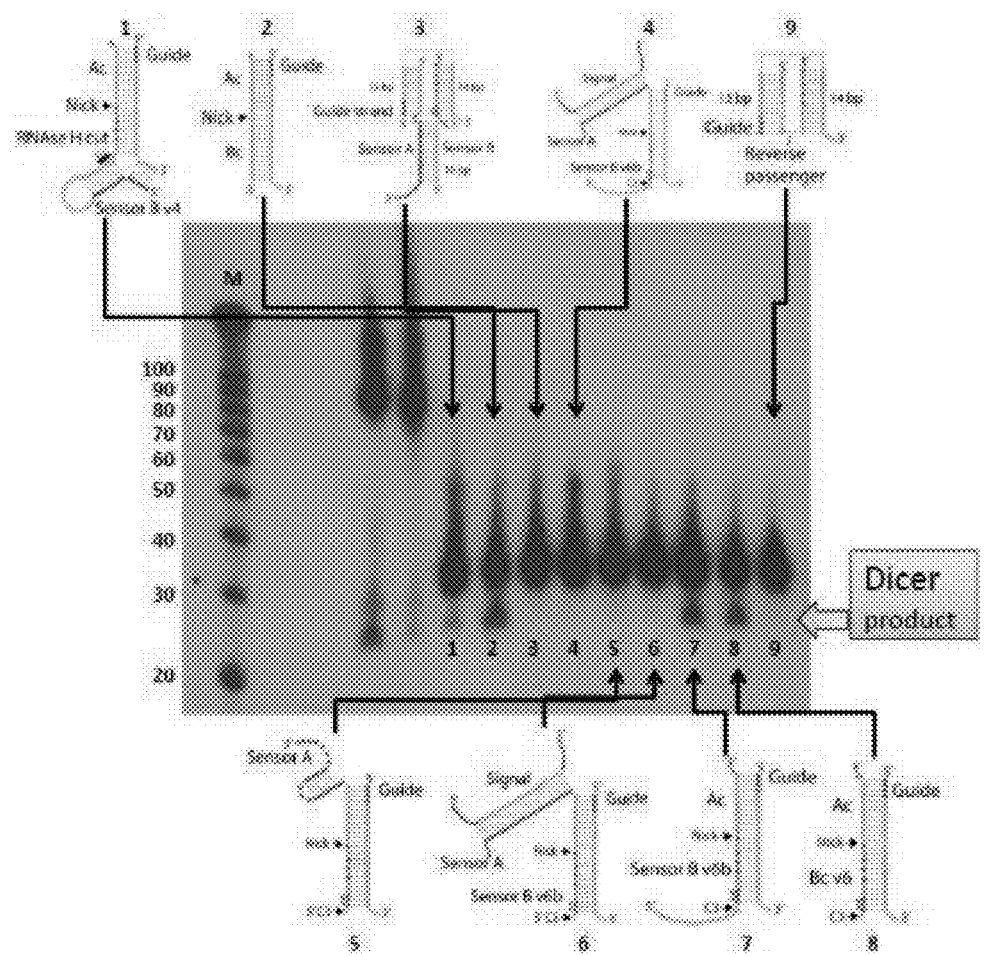
Figure 32:
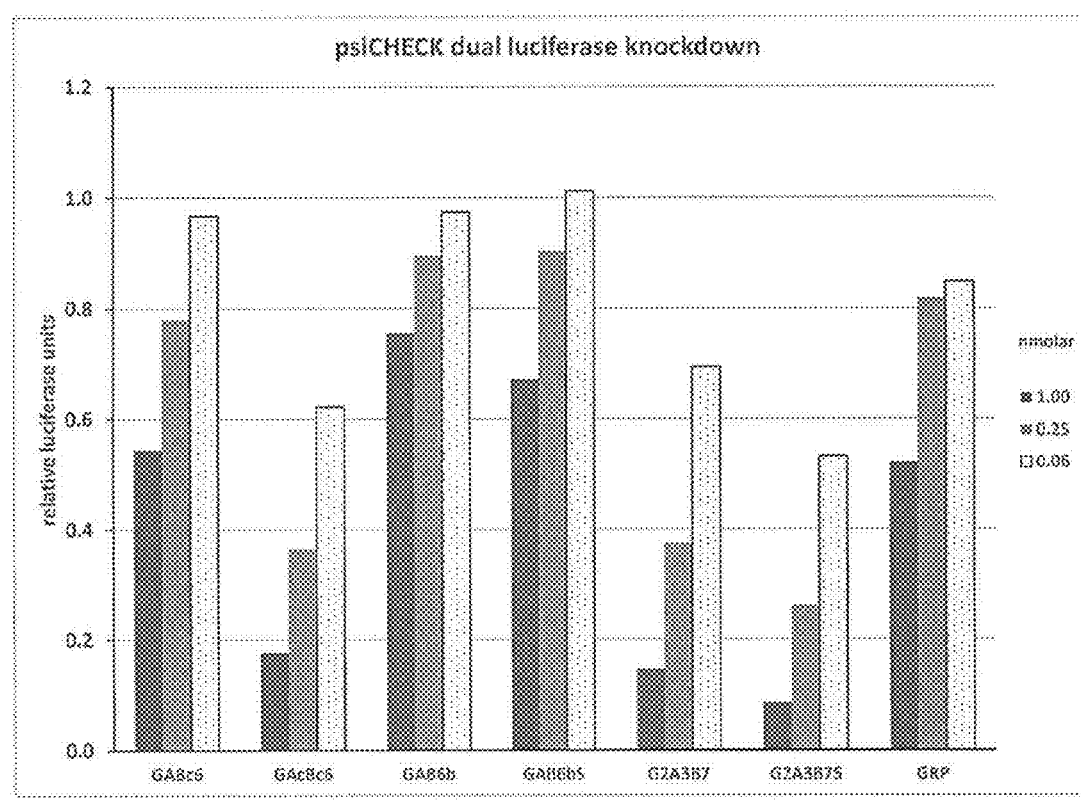

FIG. 31 shows a Northern blot of exemplary Medusa complexes with and without signal strands and controls. Lane M, RNA size markers, number of nucleotides is indicated. Lane 1, G Ac B4 SEQ ID NO: 1, SEQ ID NO: 58 (5' mA mA mG mG mU C C C T G A T C G A C G A A G A G C U C A U C A G G G U A A C mU A mG A mG A U mC C C U C A G A C G C A A G T-3'); lane 2, G Ac Bc (SEQ ID NO: 1 and SEQ ID NO: 59 (5' G G U A A C U A G A G A U C C C U C A G A C G C A A G T-3'); lane 3, GAB6b (SEQ ID NO:1, SEQ ID NO: 5, SEQ ID NO: 8 and SEQ ID NO: 9); lane 4, G A B6b S (SEQ ID NO: 1, SEQ ID NO: 5, SEQ ID NO: 8, SEQ ID NO:9 and SEQ ID NO: 16); lane 5, G A B6c (SEQ ID NO: 1, SEQ ID NO: 5, and SEQ ID NO: 19); lane 6, G A B6c S (SEQ ID NO: 1, SEQ ID NO: 5, SEQ ID NO: 19, and SEQ ID NO: 16); lane 7, G Ac B6b (SEQ ID NO: 1, SEQ ID NO: 2, SEQ ID NO: 8 and SEQ ID NO: 9); lane 8, G Ac B6c (SEQ ID NO: 1, SEQ ID NO: 2 and SEQ ID NO: 19); lane 9, G RP (SEQ ID NO: 1 and SEQ ID NO: 4). Region between Lanes M and 1 contain unrelated constructs FIG. 32 shows the results of a dual luciferase assay with the exemplary Medusa construct A Gc6, G Ac Bc6, G A B6b S, G2 A3 B7, G2 A3 B7S and G RP at 1.0, 0.25 and 0.6 nMolar concentrations.

Figure 33:
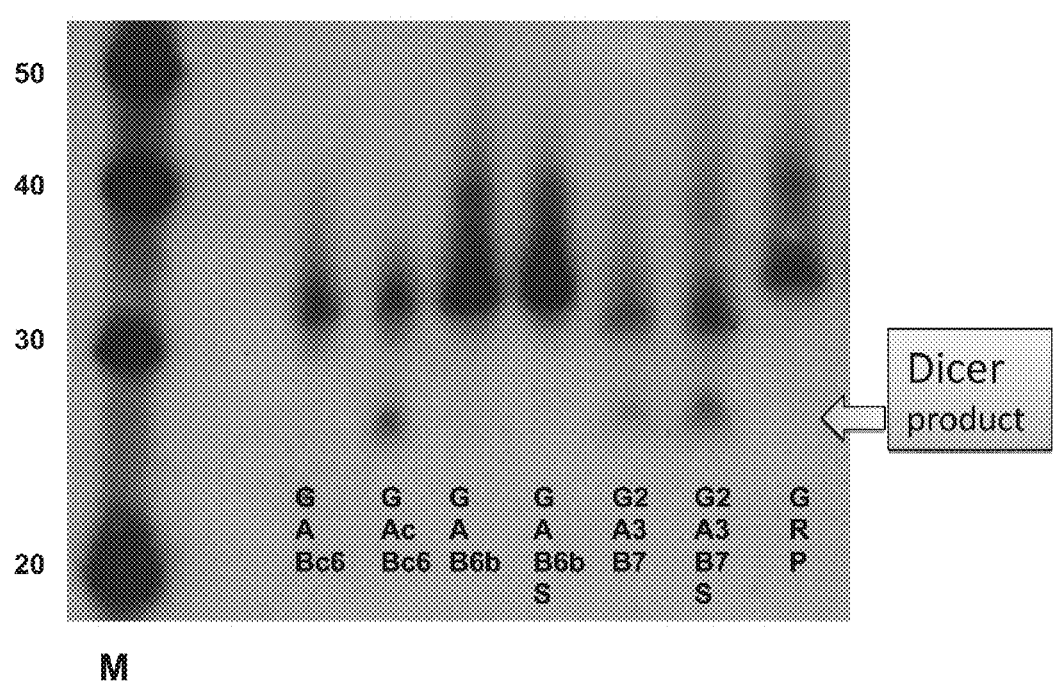

FIG. 33 shows a Northern blot of exemplary Medusa complexes with and without signal strands and controls. Lane M, RNA size markers, number of nucleotides is indicated. Probe (oligo 544) hybridizes to intact guide strand G (29 nucleotides) seen in all lanes and the approximately 21 nucleotide Dicer product, indicated by the arrow, seen with G Ac Bc6, G2 A3 B7 and G2 A3 B7 S (lanes 2, 5 and 6, respectively).

Figure 34:
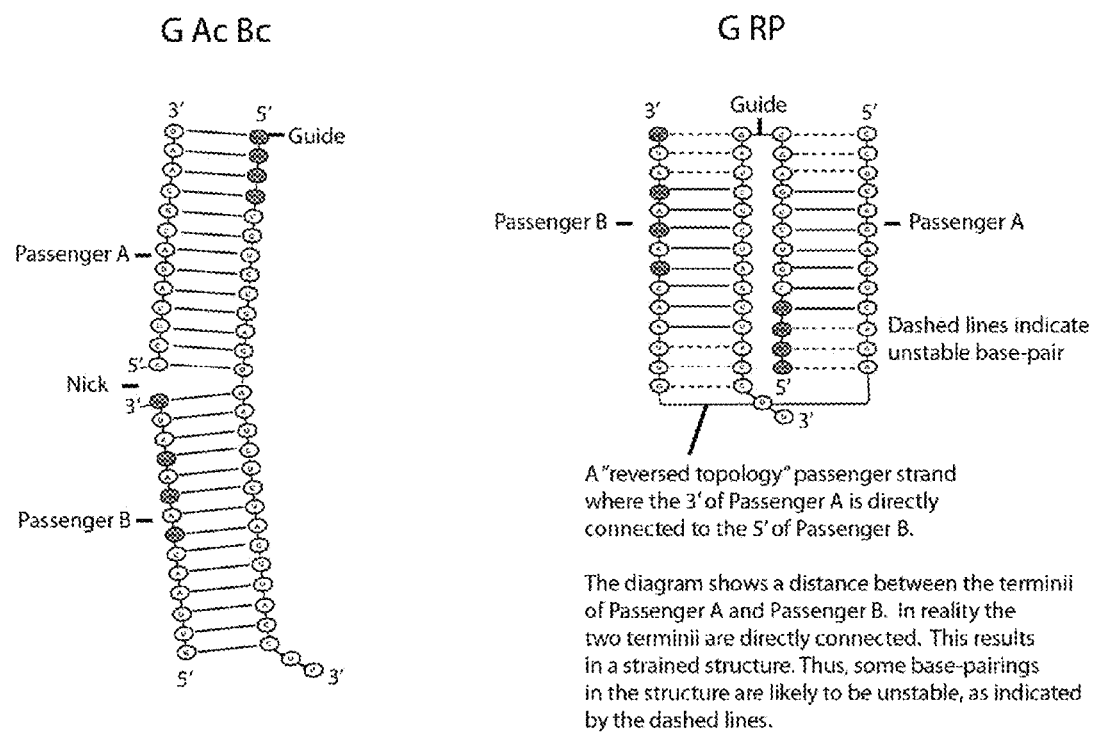

FIG. 34 shows an unlocked (G Ac Bc (SEQ ID NO: 1, SEQ ID NO: 2, and SEQ ID NO: 3)) and a locked (G RP (SEQ ID NO: 1, and SEQ ID NO: 4)) RNAi targeting domain. G Ac Bc (SEQ ID NO: 1, SEQ ID NO: 2, and SEQ ID NO: 3) and G RP (SEQ ID NO: 1, and SEQ ID NO: 4) have identical sequences, but in G RP the 3' of Passenger A is directly linked to the 5' of Passenger B, comprising a single "reversed topology" passenger strand. This linkage locks the RNAi targeting domain into a folded conformation that minimizes proper Dicer processing.

Figure 35:
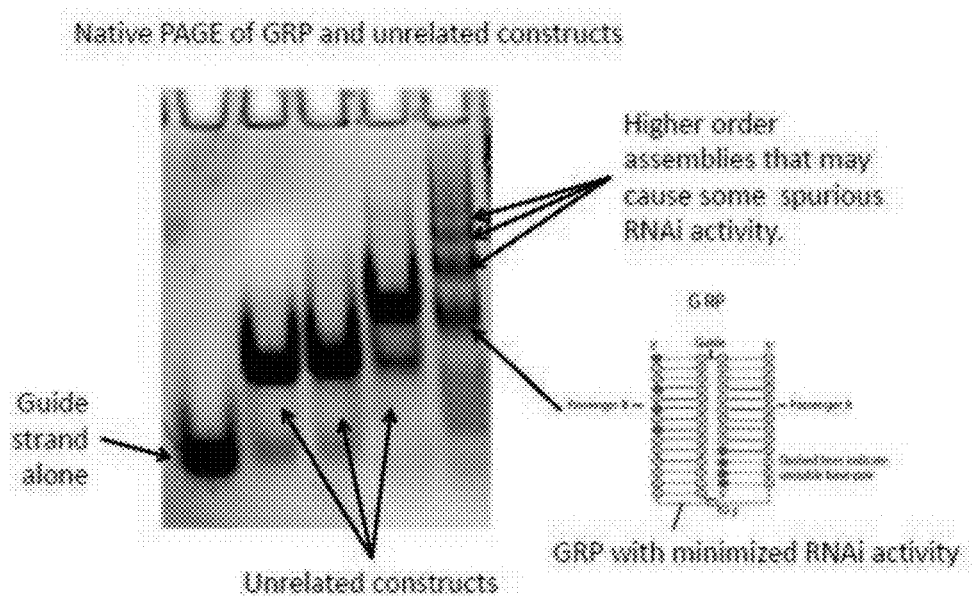

FIG. 35 shows the assembled G RP (SEQ ID NO: 1, and SEQ ID NO: 4) product. The individual strands composing G RP SEQ ID NO: 1, and SEQ ID NO: 4) or G Ac Bc (SEQ ID NO: 1, SEQ ID NO: 2, and SEQ ID NO: 3) were ordered from a commercial company, Thermo Scientific. For assembly the strands composing G Ac Bc (SEQ ID NO: 1, SEQ ID NO: 2, and SEQ ID NO: 3) or G RP (SEQ ID NO: 1, and SEQ ID NO: 4) were combined at 1 micromolar concentration in 1×PBS buffer (approximately 150 mM KCl with other components), heated to ~90 degrees Celsius, and allowed to cool to room temperature. During this process the strands self-assemble into either G Ac Bc (SEQ ID NO: 1, SEQ ID NO: 2, and SEQ ID NO: 3) or G RP (SEQ ID NO: 5). The resulting G RP (SEQ ID NO: 1, and SEQ ID NO: 4) products were assessed by running through 8% non-denaturing polyacrylamide gel in 1×TBE buffer following standard practices in the art. The first lane on the left shows the band corresponding to the Guide strand alone. In the G RP (SEQ ID NO: 1, and SEQ ID NO: 4) lane, there is a clear band showing a construct corresponding to the G RP construct in the correct conformation. In this conformation, Dicer processing is minimized. In addition, there are a number of higher molecular weight lanes, corresponding to incorrect, multimeric assemblies of G (SEQ ID NO: 1) and RP (SEQ ID NO: 4) strands. These higher molecular weight products can have spurious Dicer processing and RNAi activity. If desired, these products can be removed by filtering using HPLC, or filtration membranes with the appropriate molecular weight cutoff, or by extracting them using native polyacrylamide gel electrophoresis.

Figure 36:
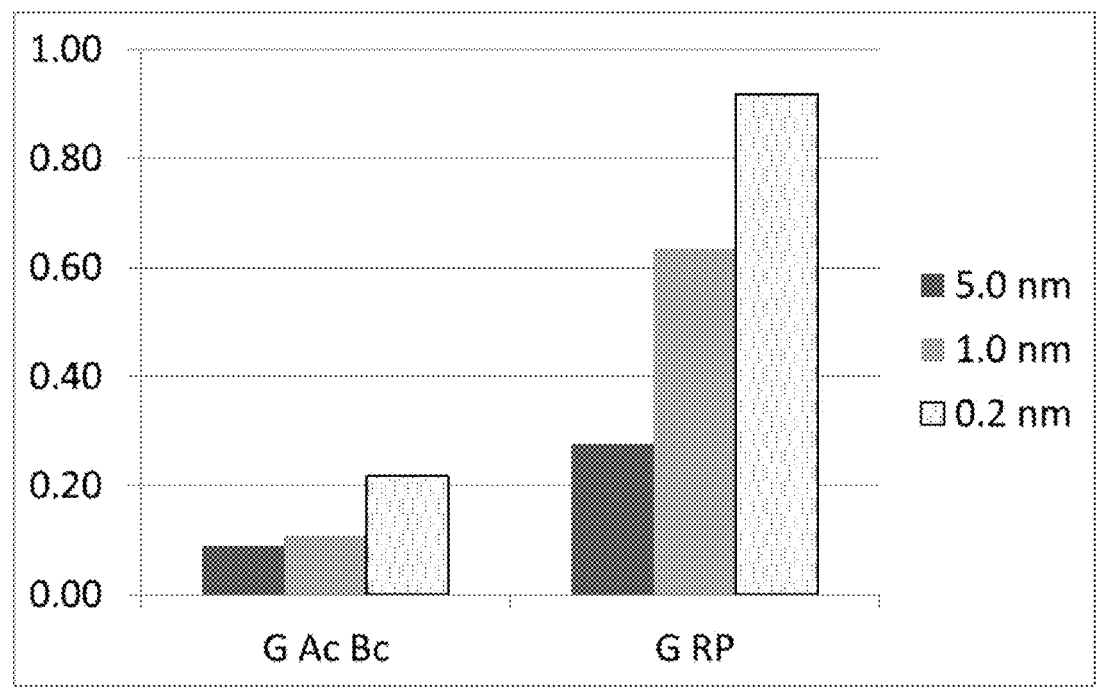

FIG. 36 shows the results of a dual luciferase assay with G Ac Bc and G RP exemplary Medusa complexes at 5.0, 1.0 and 0.2 nMolar concentrations.

Figure 37:
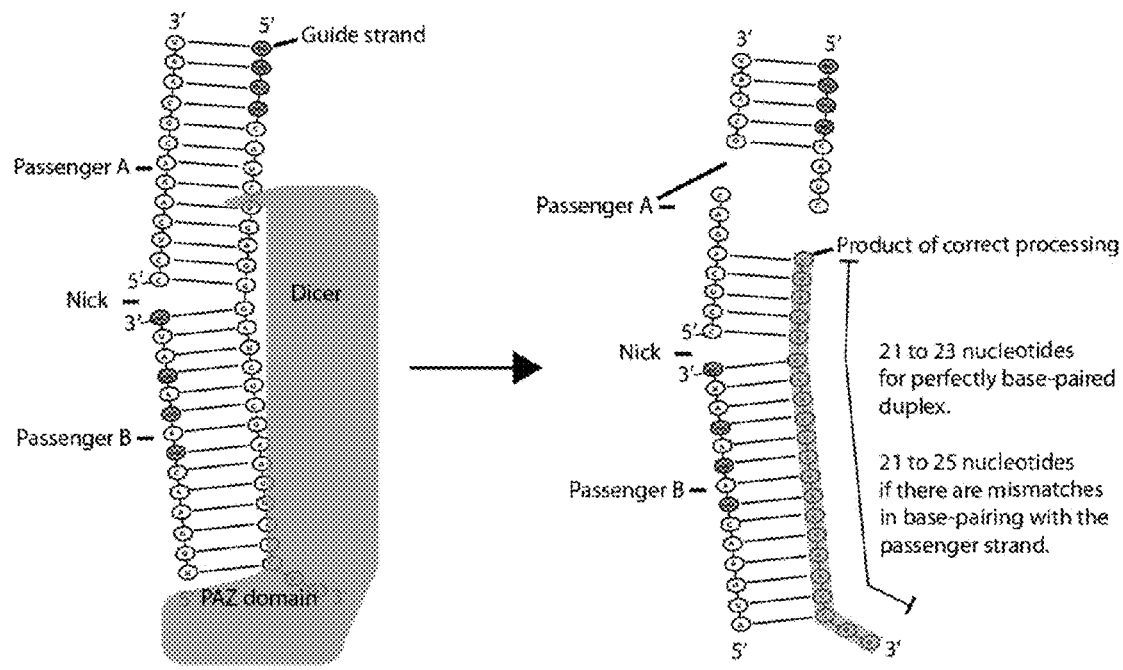

FIG. 37 shows the definition of Dicer processing. For a duplex RNAi targeting domain with a guide strand, such as the one shown (G Ac Bc (SEQ ID NO: 1, SEQ ID NO: 2, and SEQ ID NO: 3) from FIG. 34), correct processing occurs when PAZ domain of Dicer binds to 3' of the Guide strand and the endonuclease domain of Dicer cleaves the 5' end of the guide strand in the position indicated. For a perfectly base-paired RNAi targeting domain, this should produce a 21 to 23 nucleotide long product, highlighted in gray. For an imperfect duplex, the product can be up to 25 nucleotides long.

DETAILED DESCRIPTION

Herein described are signal activatable constructs for enzyme-assisted molecular delivery and related components, compositions, methods and systems.

The term "signal activatable construct" as used herein indicates a molecular complex that can have more than one conformation, and at least one of the conformations results from the binding of a signal molecule to the molecular complex. Typically, the conformation associated to the binding of a signal molecule to the molecular complex is also associated to a chemical and/or biological activity that characterizes the conformation as active with respect to the identified activity. Accordingly, signal activatable constructs herein described can have at least one active conformation and at least one inactive conformation with respect to the enzymatic activity of the enzyme assisted molecular delivery. Switching between an inactive conformation to an active conformation is triggered by binding of the signal molecule to the construct.

Signal activatable constructs and related components herein described comprise one or more polynucleotides. The term "polynucleotide" as used herein indicates an organic polymer composed of two or more monomers including nucleotides, nucleosides or analogs thereof. The term "nucleotide" refers to any of several compounds that consist of a ribose or deoxyribose sugar joined to a purine or pyrimidine base and to a phosphate group and that is the basic structural unit of nucleic acids. The term "nucleoside" refers to a compound (such as guanosine or adenosine) that consists of a purine or pyrimidine base combined with deoxyribose or ribose and is found especially in nucleic acids. The term "nucleotide analog" or "nucleoside analog" refers respectively to a nucleotide or nucleoside in which one or more individual atoms have been replaced with a different atom or a with a different functional group. Exemplary functional groups that can be comprised in an analog include methyl groups and hydroxyl groups and additional groups identifiable by a skilled person.

Exemplary monomers of a polynucleotide comprise deoxyribonucleotide, ribonucleotides, LNA nucleotides and PNA nucleotides. The term "deoxyribonucleotide" refers to the monomer, or single unit, of DNA, or deoxyribonucleic acid. Each deoxyribonucleotide comprises three parts: a nitrogenous base, a deoxyribose sugar, and one or more phosphate groups. The nitrogenous base is typically bonded to the 1' carbon of the deoxyribose, which is distinguished from ribose by the presence of a proton on the 2' carbon rather than an —OH group. The phosphate group is typically bound to the 5' carbon of the sugar. The term "ribonucleotide" refers to the monomer, or single unit, of RNA, or ribonucleic acid. Ribonucleotides have one, two, or three phosphate groups attached to the ribose sugar. The term "locked nucleic acids" (LNA) as used herein indicates a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA. LNA nucleotides can be mixed with DNA or RNA bases in the oligonucleotide whenever desired. The locked ribose conformation enhances base stacking and backbone pre-organization. This significantly increases the thermal stability (melting temperature) of oligonucleotides. LNA oligonucleotides display unprecedented hybridization affinity toward complementary single-stranded RNA and complementary single- or double-stranded DNA.

Structural studies have shown that LNA oligonucleotides induce A-type (RNA-like) duplex conformations. The term "polyamide polynucleotide", "peptide nucleic acid" or "PNA" as used herein indicates a type of artificially synthesized polymer composed of monomers linked to form a backbone composed of repeating N-(2-aminoethyl)-glycine units linked by peptide bonds. The various purine and pyrimidine bases are linked to the backbone by methylene carbonyl bonds. Since the backbone of PNA contains no charged phosphate groups, the binding between PNA/DNA strands is stronger than between DNA/DNA strands due to the lack of electrostatic repulsion. PNA oligomers also show greater specificity in binding to complementary DNAs, with a PNA/DNA base mismatch being more destabilizing than a similar mismatch in a DNA/DNA duplex. This binding strength and specificity also applies to PNA/RNA duplexes. PNAs are not easily recognized by either nucleases or proteases, making them resistant to enzyme degradation. PNAs are also stable over a wide pH range. In some embodiments, polynucleotides can comprise one or more non-nucleotidic or non nucleosidic monomers identifiable by a skilled person.

Accordingly, the term "polynucleotide" includes nucleic acids of any length, and in particular DNA, RNA, analogs thereof, such as LNA and PNA, and fragments thereof, possibly including non-nucleotidic or non-nucleosidic monomers, a each of which can be isolated from natural sources, recombinantly produced, or artificially synthesized. Polynucleotides can typically be provided in single-stranded form or double-stranded form (herein also duplex form, or duplex).

A "single-stranded polynucleotide" refers to an individual string of monomers linked together through an alternating sugar phosphate backbone. In particular, the sugar of one nucleotide is bond to the phosphate of the next adjacent nucleotide by a phosphodiester bond. Depending on the sequence of the nucleotides, a single-stranded polynucleotide can have various secondary structures, such as the stem-loop or hairpin structure, through intramolecular self-base-paring. A hairpin loop or stem loop structure occurs when two regions of the same strand, usually complementary in nucleotide sequence when read in opposite directions, base-pairs to form a double helix that ends in an unpaired loop. The resulting lollipop-shaped structure is a key building block of many RNA secondary structures. The term "small hairpin RNA" or "short hairpin RNA" or "shRNA" as used herein indicate a sequence of RNA that makes a tight hairpin turn and can be used to silence gene expression via RNAi.

A "double-stranded polynucleotide", "duplex polynucleotide" refers to two single-stranded polynucleotides bound to each other through complementarily binding. The duplex typically has a helical structure, such as double-stranded DNA (dsDNA) molecule or double stranded RNA, is maintained largely by non-covalent bonding of base pairs between the strands, and by base stacking interactions.

The constructs and compolenents herein described are suitable in many embodiments for enzyme assisted molecular delivery. The term "molecular delivery" as used herein indicates any process by which controlled activation of molecular complexes regulates the release of a chemical compound for various purposes.

The term "enzyme-assisted" as used herein is defined to mean any chemical process where a protein or other chemical entity is used to catalyze or increase the rate of a chemical reaction. The protein used for this purpose can include, but is not limited to, chains of amino acids (natural or unnatural), that may or may not contain other chemical variations and can have a defined secondary structure. The chemical reaction can include, but is not limited to, reactions of RNA or portions of RNA, DNA or portions of DNA, and/or any nucleotide or derivative thereof. Typically, enzymes catalyze reactions through binding to specific or aspecific target molecular portions usually indicated as binding sites.

In several embodiments, the enzyme-assisted molecular delivery herein described is an XRN1 assisted molecular delivery. In several embodiments, the enzyme-assisted molecular delivery herein described is an XRN1 assisted molecular delivery. The term "XRN1" as used herein refers to an exoribonuclease enzyme that is capable of degrading ribopolynucleotides by removing terminal nucleotides from the 5' terminus of the ribopolynucleotide. As used herein the term "XRN1" comprises any enzymes whether naturally occurring or synthetically modified including any enzyme modified in one or more residues which substantially retain an exoribonuclease activity such as the one herein described. Naturally occurring XRN1 enzymes which are members of the XRN1 family can be found in many organisms including yeast, nematode, fruit fly, and human. XRN1 is also referred as Pacman, KEM1, SEP1, DST2, RAR5 SKIT and DST2 to one skilled in the art.

In several embodiments, the enzyme-assisted molecular delivery herein described is an RNAase H assisted molecular delivery. The term "RNAse H" as used herein refers to a nonspecific endonuclease that is able to catalyze RNA cleavage via a hydrolytic mechanism. In particular RNase H's ribonuclease activity cleaves a 3'-O—P bond of RNA in a DNA:RNA duplex to produce 3' hydroxyl and 5' phosphate terminated products. RNAase H cleaves the RNA strand in DNA:RNA duplexes. The minimal substrate for RNAse H cleavage activity is usually a 5 to 7 base pair long stretch of duplex DNA:RNA. As used herein the term "RNAase H" comprises any enzymes whether naturally occurring or synthetically modified including any enzyme modified in one or more residues which substantially retain an endonucleasic activity such as the one herein described. Naturally occurring RNAase H enzyme which are members of the RNAse H family can be found in nearly all organisms, from archaea to prokaryote and eukaryote are identifiable by a skilled person. In human cells, RNAse H commonly cleaves the RNA sequence of a DNA:RNA duplex at a position that is 5 nucleotides from the 5' end of the RNA sequence forming the duplex. If the duplex is longer than 7 base pairs, RNAse H can cleave at additional positions to the 3' of the first cleavage site. The mammalian RNAse H class enzymes cleave the RNA portion of DNA:RNA duplexes. RNAse H class enzymes constitute the dominant mechanism of activity for many antisense oligonucleotide drugs. RNAse H can be typically active both in the cytoplasm and the nucleus.

In particular in some embodiments, the enzyme assisted molecular delivery is directed to release a targeting domain with a biological environment and in particular within a cell, and the release of the targeting domain can be catalyzed by XRN1 or RNAaseH in combination with dicer and/or an argonaute enzyme.

A "domain" in the sense of the present disclosure indicates a part of a given polynucleotide having a structure specifically associated with a function and that exist independently of the rest of the polynucleotide. The structure/function association in a domain is typically conserved during the chemical and/or biological reaction associated with the polynucleotide.

A "targeting domain" as used herein indicates a domain of a polynucleotide associated with the function of binding or reacting with a predetermined target within a biological environment and in particular within a cell.

The term "target" as used herein indicates an analyte of interest. The term "analyte" refers to a substance, compound, moiety, or component whose presence or absence in a sample is to be detected. Analytes include but are not limited to biomolecules and in particular biomarkers. The term "biomolecule" as used herein indicates a substance, compound or component associated with a biological environment including but not limited to sugars, amino acids, peptides, proteins, oligonucleotides, polynucleotides, polypeptides, organic molecules, haptens, epitopes, biological cells, parts of biological cells, vitamins, hormones and the like. The term "biomarker" indicates a biomolecule that is associated with a specific state of a biological environment including but not limited to a phase of cellular cycle, health and disease state. The presence, absence, reduction, upregulation of the biomarker is associated with and is indicative of a particular state. The "biological environment" refers to any biological setting, including, for example, ecosystems, orders, families, genera, species, subspecies, organisms, tissues, cells, viruses, organelles, cellular substructures, prions, and samples of biological origin.

Exemplary targeting domains in the sense of the present disclosure comprise siRNA, saRNA, microRNA and additional polynucleotides identifiable by a skilled person.

In embodiments herein described, the targeting domain of the disclosure a duplex RNA duplex RNA of about 19 to about 30 bp length comprising a guide strand complementary bound to a passenger strand nicked in two passenger strand segments having from about to 2 bp to about 17 bp length and allowing the targeting domain duplex RNA to adopt a folded conformation and an unfolded conformation. In the folded conformation opposite ends of the targeting domain duplex RNA are in a configuration which minimizes processing of the guide strand by dicer and/or an argonaute enzyme. In the unfolded conformation, the opposite ends of the targeting domain duplex RNA are in a configuration allowing processing of the guide strand by dicer and/or an argonaute enzyme.

Figure 1:
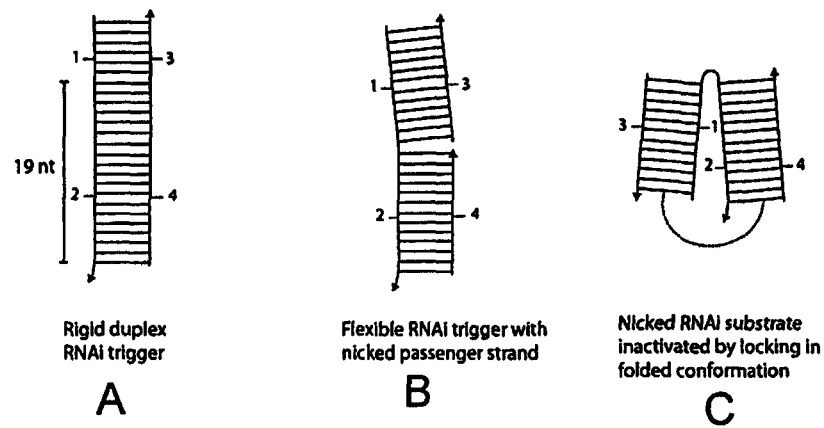
FIG. 1 shows a schematic illustration of a targeting domain inclusive of segments 1, 2, 3 and 4, according to an embodiment herein described showing the general structure (FIG.

Reference is made to the schematic illustration of FIG. 1 which shows an exemplary targeting domain according to an embodiment herein described, in a depiction schematically illustrating the RNA duplex comprised in an exemplary targeting domain (FIG. 1, panel A) the unfolded conformation of the exemplary targeting domain of FIG. 1, panel A (FIG. 1, panel B) and the folded conformation of the exemplary targeting domain of FIG. 1, panel A (FIG. 1, panel C).

In the illustration of FIG. 1 the targeting domain comprises a guide strand (1,2) complementary and complementary binding to passenger strand (3,4) to form an RNA duplex.

The term "complementary" as used herein indicates a property of single stranded polynucleotides in which the sequence of the constituent monomers on one strand chemically matches the sequence on another other strand to form a double stranded polynucleotide. Chemical matching indicates that the base pairs between the monomers of the single strand can be non-covalently connected via two or three hydrogen bonds with corresponding monomers in the another strand. In particular, in this application, when two polynucleotide strands, sequences or segments are noted to be complementary, this indicates that they have a sufficient number of complementary bases to form a thermodynamically stable double-stranded duplex. Double stranded of complementary single stranded polynucleotides include dsDNA, dsRNA, DNA:RNA duplexes as well as intramolecular base paring duplexes formed by complementary sequences of a single polynucleotide strand (e.g. hairpin loop).

The term 'complementary bind", "base pair", "complementary base pair" as used herein with respect to nucleic acids indicates the two nucleotides on opposite polynucleotide strands or sequences that are connected via hydrogen bonds. For example, in the canonical Watson-Crick DNA base pairing, adenine (A) forms a base pair with thymine (T) and guanine (G) forms a base pair with cytosine (C). In RNA base paring, adenine (A) forms a base pair with uracil (U) and guanine (G) forms a base pair with cytosine (C). Accordingly, the term "base pairing" as used herein indicates formation of hydrogen bonds between base pairs on opposite complementary polynucleotide strands or sequences following the Watson-Crick base pairing rule as will be applied by a skilled person to provide duplex polynucleotides. Accordingly, when two polynucleotide strands, sequences or segments are noted to be binding to each other through complementarily binding or complementarily bind to each other, this indicate that a sufficient number of bases pairs forms between the two strands, sequences or segments to form a thermodynamically stable double-stranded duplex, although the duplex can contain mismatches, bulges and/or wobble base pairs as will be understood by a skilled person.

The term "thermodynamic stability" as used herein indicates a lowest energy state of a chemical system. Thermodynamic stability can be used in connection with description of two chemical entities (e.g. two molecules or portions thereof) to compare the relative energies of the chemical entities. For example, when a chemical entity is a polynucleotide, thermodynamic stability can be used in absolute terms to indicate a conformation that is at a lowest energy state, or in relative terms to describe conformations of the polynucleotide or portions thereof to identify the prevailing conformation as a result of the prevailing conformation being in a lower energy state. Thermodynamic stability can be detected using methods and techniques identifiable by a skilled person. For example, for polynucleotides thermodynamic stability can be determined based on measurement of melting temperature $T_m$, among other methods, wherein a higher $T_m$ can be associated with a more thermodynamically stable chemical entity as will be understood by a skilled person. Contributors to thermodynamic stability can include, but are not limited to, chemical compositions, base compositions, neighboring chemical compositions, and geometry of the chemical entity.

In particular, in the exemplary targeting domain described in FIG. 1, segment (3) is configured to complementary bind segment (1) in a (1):(3) duplex, and segment (4) is configured to complementary bind a portion of segment (2) in a (2):(4) duplex. Mismatches and bulges in either the (1):(3) or (2):(4) duplexes are permitted as long as the as long as the melting temperatures $T_m$ of (1):(3) and (2):(4) duplexes are predicted to be greater than the operating temperature (e.g. 37° C. in embodiments in which detection of formation of RNA duplex is desired through methods known to one skilled in the art such as Native PAGE followed by visualization or UV-vis spectroscopy). In embodiments herein described, duplex formation can be verified by Native PAGE or UV vis spectroscopy or additional techniques identifiable by a skilled person.

In particular in the illustration of FIG. 1, a 19 nt region is indicated on the guide strand (1,2) which complementary binds the passenger strand (3,4) to provide a thermodynamically stable double stranded polynucleotide at a desired operating temperature. Accordingly, in the exemplary illustration of FIG. 1, the 2 base overhang of segment (2) does not need to be complementary to the segment (4), and the region of segment (1) outside the 19 nt region does not need to be complementary to the segment (3) to obtain a thermodynamically stable double stranded structure.

In the illustration of FIG. 1, panel A, the guide strand comprises segment (1) covalently linked at one end to a segment (2) and the passenger strand comprising a segment (3), covalently linked at one end to a segment (4). The term "covalent binding" or "covalently linked" as used herein indicates connection between two segments through formation of a chemical bonding that is characterized by sharing of pairs of electrons between atoms, known as the covalent bond. Examples covalent binding can include, but are not limited to covalent bonds formed between any two of the following: RNA or portions RNA, DNA or portions of DNA, any nucleotide or derivative thereof, and/or enzyme.

In particular the exemplary illustration of FIG. 1, panel A, guide strand (1,2) is the guide strand of an RNAi trigger, which in the illustration of FIG. 1 is a siRNA, but can be other RNAai triggers such as a Dicer substrate siRNA, a miRNA or other Dicer substrates (see e.g. FIG. 20).

In the illustration of FIG. 1, panel B, the passenger strand (3,4) is nicked into passenger strand segments (3) and (4). The term "nicked" as used herein with reference to a polynucleotide strand of a double stranded polynucleotides indicates a gap in the direct covalent linkage between two nucleotides of the polynucleotide chain forming the strand that are engaged in complementary binding within double stranded polynucleotide. Accordingly, an RNA duplex comprising a nicked passenger strand can be obtained by cleaving the covalent linkage between suitable nucleotides e.g. by using suitable endoribonucleases (such as an RNAase III enzyme) or by synthesis of a double stranded polynucleotide with selected dideoxyribonucleotides used to introduce the nick as will be understood by a skilled person. Additional approaches will also be identifiable by the skilled person directed to obtain a passenger strand in which two of the nucleotides forming the polynucleotide chain engaged in the complementary binding with the guide strand are not directly covalently linked to each other. For example, in the illustration of FIG. 1, panel B segments (3) and (4) can be connected by an unstructured covalent linker (e.g. PEG or polynucleotide loop) as long as the linker allows (3) and (4) to adopt a folded conformation that prevents RNAi activity. In the illustration of FIG. 1, panel B if an unstructured linker is introduced between 3 and 4, the unstructured linker can have a fully stretched length of at least 2 nm.

In the illustration of FIG. 1, panel C, to inactivate the RNAi substrate, a link is introduced between the two ends of the duplex to force the fold illustrated. In particular in the illustration of FIG. 1, panel C, a covalent link is included between the terminal backbone positions or bases on two ends of the duplex to lock the two ends of the targeting domain. Alternatively, the lock can bind together two interior positions on (2):(4) and (1):(3), in a configuration allowing the resulting structure migrate at a substantially different rate in 10% Native PAGE gel compared to the conformation of FIG. 1, panel A and FIG. 1, panel B In the exemplary illustration of FIG. 1, panel C the linkage between the two opposite ends of the targeting domain provide a configuration of the opposite ends such that those ends are at an angle of about 10° between each other. Additional suitable configurations of the opposite ends suitable for a folded conformation of the targeting domain comprise angles up to about 90° as will be understood by a skilled person. Calculation of the angle between the opposite ends of the targeting domain can be performed by estimating the length of a duplex segment to be approximately 0.34 nm per basepair, and the maximum length of an unstructured polynucleotide of less than or equal to 20 nucleotides to be approximately 0.5 nm per nucleotide, and then using trigonometry to calculate the maximum possible angle assuming the estimated duplex lengths and the maximum unstructured polynucleotide length. If the different segments are linked via a non-polynucleotide linker, such as a C3 or a polyethylene glycol linker, then for a short linker the one can use the maximum possible length of the linker as calculated from the length of the constituent molecular bonds and angles to calculate the maximum angle via trigonometry. For unstructured polynucleotide linkers longer than 20 nucleotides or polymer linkers longer than 20 polymer units, the average end to end distance can also be calculated using polymer physics and an approximate range of motion can be established by considering the energetic penalty of stretching the unstructured polymer beyond its average end to end distance. In these cases the bending angle should be estimated to remain below the maximum angle of 90 degrees with at least 90% probability. In a solution targeting domains herein described are expected to change in accordance with temperature, length of linkage between the opposite ends and additional parameters identifiable by a skilled person.

Additionally, Forster Resonance Energy Transfer (FRET) experiments can be used to experimentally estimate the angle in solution by attaching a quencher fluorophore pair or two fluorophores known to have FRET activity on the arms of the construct adjacent to the angle. The distance between the FRET pairs, and hence the distance between their attachment points on the construct, can then be estimated by recording and analyzing fluorescence signals from the construct in solution.

In the exemplary illustration of a targeting domain in the sense of the present disclosure provided in FIG. 1, switching from the unfolded conformation of FIG. 1, panel B to the folded conformation of FIG. 1, panel C and vice versa is determined by various factors such as presence or absence of the covalent linkage length of the covalent linkage between the opposite ends of the domain, operating temperature, the salt concentration, the structure of the linkage between the opposite ends of the domain, the presence in solution of molecules that can affect the structure of the linkage, and additional factors identifiable by a skilled person.

Reference is also made to the exemplary illustration of FIG. 2 in which different attachment of the targeting domain in a folded conformation are shown. In some embodiments no extension of the 3' of the guide strand beyond the two base overhang is included to increase proper processing of the guide strand. In some embodiments if the 3' of the guide strand is extended, a non-nucleic acid linker can be comprised in particular when minimization of the interference of the 3' overhang with processing of the guide strand and its proper functioning in RISC is desired. In this connection reference is made for example to Wang et al (2009) incorporated herein by reference in its entirety.

Variations in the targeting domain and related molecular construct shown in the illustration of FIG. 1 and FIG. 2 are identifiable by a skilled person in view of the present disclosure. For example, (1):(3) does not have to be the same length as (2):(4), ii) separately, (1):(3) and 2:4 can exceed the length of an RNA duplex of about 18 bp; iii) neither (1):(3) or (2):(4) can be so short that the melting temperature of the duplex is calculated to be less than the operating temperature of the construct considering all modifications according to the present disclosure; and v) in embodiments wherein the construct is to be used in a cell the RNAi substrate overall can be no longer than 30 bp to prevent immunogenic toxicity.

In some embodiments, constructs herein described are signal activatable construct that comprise a locking sensor configured for providing different conformations upon binding of a signal molecule to a suitable segment of the locking sensor through interrelation of various segments of the locking sensor. In particular, in several embodiments the locking sensor is configured to provide different conformations following binding of the locking sensor to a signal molecule that can be signal polynucleotide or another molecule able to complementarily bind a suitable portion of the locking sensor. The term "signal polynucleotide" as used herein indicates a polynucleotide that is capable of acting as a signal molecule for the signal activated constructs and related components herein described. Accordingly, a signal polynucleotide herein described is capable of triggering a switch between an inactive conformation and an active conformation of the signal activated molecular construct upon binding to a segment of the signal activated construct.

The term "segment" as used herein indicates a portion of a signal activated construct having chemical and/or biological properties that are functional to changes in conformation of the signal activated construct or components thereof, and/or to a related ability to perform the enzyme assisted release herein described.

In some embodiments the locking sensor comprises a toehold segment, a displacement segment, and an activation segment. In particular in those embodiments herein described each of an activation segment, a toehold segment, and a displacement segment comprises at least one polynucleotide portion configured so that i) the toehold segment is complementary to a signal polynucleotide or other suitable signal molecule; ii) the activation segment is complementary to the displacement segment; iii) the displacement segment is complementary to the signal polynucleotide.

Reference is made to the illustration of FIG. 3 to FIG. 8, showing molecular complexes of the disclosure in which an exemplary targeting domain (100) is locked in a folded conformation (FIG. 3, panel A, 3, panel C, 4, panel A, 4, panel C, 5, panel A, 5, panel C, 6, panel C, 6, panel C, 7, panel A, 7, panel C, 8, panel A, 8, panel C) or presented in an unfolded conformation (FIG. 3, panel B, 3, panel D, 4, panel B, 4, panel D, 5, panel B, 5, panel D, 6, panel B, 6, panel D, 7, panel B, 7, panel D, 8, panel B, 8, panel D).

In the molecular complex of FIGS. 3 to 8 the locking sensor (200) comprises a toehold segment (7), a displacement segment (6), and an activation segment (5) complementary bound the displacement segment (6). In the molecular complex of FIGS. 3 to 8 the locking sensor (200) is covalently linked to the targeting domain (100) through covalent linkage of first strand (60) and second strand (50) to an end of the targeting domain (100) as illustrated in each figure.

In the exemplary embodiments of FIGS. 2 and 3 the signal activatable construct adopts thermodynamically stable inactive and active conformations depending on binding presence of a signal polynucleotide. In particular, the signal activatable construct adopts an inactive conformation in absence of the signal molecule (FIG. 3, panel A, 3, panel C, 4, panel A, 4, panel C, 5, panel A, 5, panel C, 6, panel A, 6, panel C, 7, panel A, 7, panel C, 8, panel A, 8, panel C), and switch to an active conformation upon binding of the signal molecule (FIG. 3, panel B, 3, panel D, 4, panel B, 4, panel D, 5, panel B, 5, panel D, 6, panel B, 6, panel D, 7, panel B, 7, panel D, 8, panel B, 8, panel D).

In the illustration of FIG. 3 to FIG. 8 the signal molecule is provided by a signal polynucleotide (FIGS. 3 to 6 and FIG. 8) and an aptamer (FIG. 7). Additional signal molecule can be applied to the exemplary constructs of FIG. 3 to FIG. 8 as will be understood by a skilled person. Suitable signal molecules and in particular signal polynucleotides can be artificially synthesized in or typically are already present in the environment wherein activation of the construct is desired cytoplasm of cells and analogous biochemical environments, such as a cell lysate. Exemplary signal polynucleotides according to the present disclosure include but are not limited to a synthetic polynucleotide, RNA sequence present in cytoplasm or nuclei of cells, such as mRNA, non-coding RNA, microRNA, microRNA precursors, small interfering RNA, aptamers, tRNA, and by-products of abortive RNA transcription, RNA splicing or RNA degradation. The signal polynucleotide can be present in a free form or bound to RNA binding proteins such as RISC. Additional exemplary signal molecules comprise protein and small molecules as will be understood by a skilled person.

In the illustration of FIG. 3 to FIG. 8, the inactive conformation of the molecular complexes is converted into the active conformation following binding of signal polynucleotide to the toehold segment (7), and the displacement segment (6), to displace the activation segment (5) which in the active conformation is presented as a single stranded signal polynucleotide for processing by ribonucleases such as an XRN1.

The term "displacement", "strand displacement reaction" or "branch migration reaction" as used herein generally indicates the process in which two polynucleotide strands with partially or full complementarity hybridize, displacing in the process one or more prehybridized strand or sequence. The strand displacement process can be experimentally tested or measured according to techniques herein described (see e.g. Examples 2 to 5) and identifiable by a skilled person.

Accordingly, in embodiments exemplified by of FIG. 3 to FIG. 8 the activation segment of the locking sensor complementary binds the displacement segment in an inactive conformation. In those embodiments, complementary binding of a signal molecule which can be a signal polynucleotide to the toehold segment result in an activated conformation the displacement segment and the toehold segment are displaced by the signal molecule. In particular when signal molecule is a signal polynucleotide the signal polynucleotide complementary binds the toehold segment and the displacement segment to form a signal duplex displacing the activation segment from the displacement segment.

In particular in some embodiments, in the locking sensor herein described and related constructs, binding of the signal molecule and in particular complementary binding between the signal polynucleotide and the displacement segment is more thermodynamically stable than complementary base paring between the displacement segment and the activation segment, and complementary binding between the displacement segment and the activation segment is more thermodynamically stable than complementary base paring between different portions of the activation segment.

In signal activatable constructs herein described, the relative thermodynamic stability of the various segments of the locking sensor is configured to trigger a switch from an inactive conformation to an active conformation upon binding of a signal molecule. Accordingly, switching from a conformation to another can be controlled based on a comparison of the free energy of the related systems. The term "free energy" as used herein is defined to mean a thermodynamic quantity that can be used to determine the spontaneity of a chemical reaction of transformation. Where the chemical transformation is the conversion of one polynucleotide conformation to another polynucleotide conformation, comparing the free energies of the polynucleotide conformations can be used to indicate which conformation will predominate. For example, free energy can be used to estimate thermodynamic stability of polynucleotide double-strand duplex and/or polynucleotide secondary structure that is more thermodynamically stable, but it is not limited to this use. Free energy can be estimated by computational methods, among other means.

In several embodiments, the inactivated conformation of the locking sensor or related signal activatable constructs, the melting temperature of double-stranded duplex formed by the activation segment and the displacement segment is at least about 25° C. so that the double-stranded duplex formed by the activation segment and the displacement segment is more thermodynamically stable formed by different portions of the activation segment, activation segment and toehold segment at room temperature. This is to ensure that in the absence of the signal molecule, the construct adopt the inactive conformation, with the activation segment complementarily binds to the displacement segment, rather than associating with the activation segment. The strand melting temperature (Tm) of the double-stranded duplex formed by the protection segment and the displacement segment can be experimentally tested or measured (see e.g. Example 6 to 8). Accordingly, the experiment to characterize the strand displacement reaction as described in Example 8 can use a construct comprising both the sensor domain and the targeting domain. In particular, the fluorophore quencher pair can be placed at multiple positions along the duplex formed by the displacement segment and the second segment or the displacement segment and the protection segment to allow assessment of strand displacement. Thermodynamic stability is affected by various parameters such as composition of the specific solution, pressure, temperatures as well as other conditions identifiable by a skilled person.

In configurations of the activation segment, toehold segment and displacement segment in an inactive conformation suitable to transform to an active conformation in presence of the complementary signal polynucleotide, are such that the binding of the of the complementary signal polynucleotide to the toehold segment and the displacement segment has a melting temperature (Tm) of at least about 25° C. In some of those embodiments, sequence length and composition of toehold segment and displacement segment is such that binding of the signal polynucleotide to the toehold segment and displacement segment is at least as stable as the binding between the activation segment and the displacement segment to minimize partial displacement of the activation segment from the displacement segment upon binding of the signal polynucleotide.

For example. in embodiments exemplified by FIGS. 3-5 and 8, the toehold segment and the signal polynucleotide can have at least 3 consecutive base pairs to initiate binding to the signal polynucleotide and the strand displacement process, and the toehold typically comprise be at least 4 consecutive base pairs to allow functioning at the human body temperature of 37° C. Additionally, in some embodiments, sequences of the displacement segment and activation segment can be configured with respect to the complementarity of the displacement segment and signal polynucleotide so that up to every base-pair exchange is at least equal-energy, to minimize incomplete displacement process. For example, according to some embodiments, if at certain position of the duplex, the displacement segment and the activation segment have a GC base-pair, then the signal polynucleotide can also have a GC base pair with the displacement segment at the corresponding position; if the displacement segment and the activation segment have a 2'-O-methyl G base pairs with a C at certain position, also the signal polynucleotide can base pair to the displacement segment with a 2'-O-methyl G base pairs with a C. In some embodiments, the complementary binding between the displacement segment with the signal polynucleotide can be at least as stable, and possible more stable, than the complementarily binding between the displacement segment and the activation segment. Accordingly, mismatches between the displacement segment and the activation segment at certain position, can correspond to mismatches between the signal polynucleotide and the displacement segment. In some embodiments stabilizing modifications such as 2'-O-methyls can be localized in the displacement segment, since that displacement segment of the construct base pairs with both the signal polynucleotide and the activation segment. In determining the configuration, length and sequence the delivery conditions can also be considered (e.g. temperature and salts concentrations).

In embodiments exemplified by the illustration of FIG. 7, displacement is performed upon binding of a signal molecule other than a signal polynucleotide (e.g. protein or small molecule). The related stability during the design can be calculated by determining the related thermodynamic free energy. In particular the signal molecule can be selected so that the signal molecule displacement-toehold segment complex has a lower free energy and greater thermodynamic stability of the locking sensor RNA duplex and therefore binds and displaces the duplex. In the illustration of FIG. 7, the construct is designed so that the thermodynamic free energy of binding for the construct where (6) and (7) are bound to the ligand is lower than the thermodynamic free energy of binding of (6) with (5). Determination of the free energy for a complex where the signal molecule is a non-nucleic acid signal molecule can be performed for example by measuring transition of the energy of construct assembled with varying concentrations of the signal molecule in a calorimeter, or by the techniques exemplified in Examples 6 to 9 as will be understood by a skilled person.

The minimum length of the duplex is determined by stability considerations. If the embodiment is designed for use at room temperature, then the activation:displacement duplex should have a minimum melting temperature of 25 degrees Celsius. If the embodiment is designed for operation in a physiological environment, then the duplex should have a minimum melting temperature of 37 degrees Celsius.

The maximum allowable length for the activation:displacement duplex is determined to avoid cellular toxicity and spurious activation. The maximum allowable duplex length is 29 base-pairs to avoid activation of PKR enzymes in the cell and spurious processing by endonucleases of the RNA interference maturation pathway.

A good range of duplex lengths is 14 bp to 19 bps. This confers sufficient stability with the incorporation of chemically modified nucleotides without PKR activation and without spurious processing.

Starting with an initial duplex length, a person skilled in the art can experimentally test for thermodynamic stability, nuclease resistance and PKR activation using live cells or cell lysates via methods such as Northern blotting, immunoprecipitation, or FRET assays. If the duplex is thermodynamically unstable in the cellular environment, the duplex length should be increased. If endonuclease cleavage of the duplex occurs, the duplex length should be decreased. If PKR activation occurs, the duplex length should be decreased.

In particular, in the inactive conformation of the molecular construct according to the illustration of FIG. 3, an RNA strand displacement activated sensor is shown wherein the complementary binding of displacement segment (6) with activation segment (5) forms a thermodynamically active duplex sensor (6):(5) that can be 7 to 18 bps in length, the toehold segment (7) can be 5 to 10 bp in length, and the displacement segment (6) and the activation segment (5) are sufficiently complementary to RNA activation signal for the signal to displace 5. Displacement can be verified by those skilled in the art using suitable techniques such as quencher-fluorophore experiments.

In the illustration of FIG. 3, if the toehold segment (7) is in a terminal loop configuration as shown in FIG. 3, panel C, the loop should be larger than 4 bases with no upper limit. In the illustration of FIG. 3, to allow formation of the active structure, the length of the duplex formed by displacement segment (6) and toehold segment (7) with the activation signal, should not exceed the length of the targeting domain plus activation segment (5) and unbound portions of toehold segment (7).

In the illustration of FIG. 4 the constructs of FIG. 3 are shown in an illustration wherein unstructured region in correspondence with the covalent linking of strand (60) and (50) with the targeting domain is indicated by arrows. Introduction of unstructured regions, such as the ones indicated in FIG. 4, is functional to minimize PKR activation usually triggered by stacking of duplexes and that in this particular case can be formed by the targeting and sensor:signal stems can activate the PKR pathway, leading to cellular toxicity. In particular, in the illustration of FIG. 4, panel B the arrows indicate an exemplary schematic representation of an exemplary unstructured regions that help reduce likelihood of PKR activation, that can be placed between the sensor and targeting regions. In the illustration of FIG. 4, panel B bulges and mismatches can also be placed in the sensor:signal duplex.

In the illustration of FIG. 4, panel D, the length of segment (5) and the un-paired portion of segment (7) is controlled to be short enough to enforce a bent conformation between the targeting domain (100) and the locking sensor (200). In the illustration of FIG. 4, panel D, the maximal length of an unstructured RNA strand can be calculated as approximately 0.5 nm per base, the length of a duplex RNA segment is approximately 0.3 nm per base-pair, the length of the unstructured region indicated by the arrow in D should be shorter than the length of the sensor duplex plus the length of the targeting duplex.

In several embodiments, modified bases can be used throughout the constructs herein described to increase thermodynamic stability, and nuclease resistance, decrease toxicity, and/or increase specificity. Suitable modifications comprise, for example, 2'-O-methyls, introduction of a non-nucleic acid linker and/or an unstructured RNA segment, and terminal modifications. In particular, 2'-O-methyls can be used in particular in displacement segment (6) and toehold segment (7) to increase thermodynamic stability and prevent unwinding by RNA binding proteins. In addition, non-nucleic acid linkers can be used confer desirable properties to the construct and/or portions thereof. Exemplary non nucleic acid linkers suitable to be used herein comprise C3 linkers and tri and hexa-ethylene glycol linkers as well as any biocompatible polymeric linker group with no-nonspecific association with DNA. In particular, molecular constructs herein described can comprise A linker group with a lower persistence length than nucleic acids (e.g.: C3, polyethylene glycol) to increase flexibility at the attachment point. Such a linker group can reduce interference of long overhangs against Dicer binding. Molecular constructs herein described can also comprise a non-nucleic acid linker group to interfere with degradation by exonucleases and endonucleases, including RNAi pathway enzymes. Molecular constructs herein described can further comprise an unstructured RNA segment to have non-canonical interactions with other RNA segments, leading to unpredictable tertiary conformations. Molecular constructs herein described can further comprise a terminal modification can prevent binding of the PAZ domain of Dicer, as well as other terminal modifications useful for preventing Dicer binding, such as Inverted dT Fluorescein and other groups incompatible with the PAZ domain listed from last patent.

In the illustration of FIG. 5, position of chemical modifications is schematically illustrated. In particular, in the illustration of FIG. 5 exemplary regions are shown where chemical modifications of the activatable constructs herein described can be introduced to obtain one or more of the above mentioned effects. According to the illustration of FIG. 5 suitable regions comprise the strands (50) and (60) linking the locking sensor to the targeting domain (modification A and Modification B) and the terminal portion of the toehold (7) lining the toehold (7) to the displacement segment (6) (Modification C).

In the illustration of FIG. 6, an exemplary activatable construct is shown including toehold having different structures. In particular, in the illustration of FIG. 6, panel A and FIG. 6, panel B, the sensor binding portion of the locking sensor is switched to the 5' side of the passenger strand. in the illustration of FIG. 6, panel C and FIG. 6, panel D an extra hairpin is added to the toehold increase the overall length of the duplex region of the sensor binding strand, thus increasing the specificity.

In the illustration of FIG. 7 an exemplary construct is shown in which activation between the inactive conformation to the active conformation of the construct can be performed by non-nucleic acid RNA activation signal such as aptamers. In particular, in the illustration of FIG. 7, panel A to FIG. 7, panel C a schematic illustration is provide of strand displacement reactions also work for aptamers in which, the activating RNA strand is replaced by ligand which binds to the sensor. In the illustration of FIG. 8 an exemplary construct is shown presenting an alternate sensor geometry. In particular. In the designs illustrated in FIGS. 3 to 1, the 5' and 3' ends of the passenger strand are extended to form the strands (60) and (50) and then the displacement segment (6) toehold segment (7) on one side and the activation segment (5) on the other side of the locking sensor (see FIGS. 3 to 7)

In the illustration of FIG. 8, the 5' end of the passenger strand and the 5' end of the guide strand are extended to form the sensor, the former constraints on the length of (1):(3) and (2:)(4) still apply; the geometric constraint on 5:6 is that when the linkers connecting 5:6 to the targeting domain are fully stretched (e.g. about 0.5 nm per nucleotide), the angle formed by 1-2 should still be less than 90 degrees. A skilled person can identify the constraints of this conformation based on trigonometry calculations.

In several embodiments of the signal activatable constructs herein described exemplified by the construct of FIGS. 3 to 8, in absence of a signal polynucleotide, the activation segment and the displacement segment form a first duplex through complementary binding portions, wherein in the presence of the signal polynucleotide, the displacement segment complementary binds the signal polynucleotide and the activation segment is displaced and presented for processing by XRN1. In particular, the XRN1 enzyme can degrade the activation segment (5) presented in the active form of the molecular construct allowing binding and processing of the targeting domain by Dicer or other enzyme of the RNAai inactivation pathway.

Various other configurations of the activatable constructs herein described can be identified by a skilled person upon reading of the present disclosure.

A schematic representation of an overall method to provide a targeting domain and an activable construct herein described is illustrated in FIG. 9. In particular the exemplary construct of FIG. 9 inactivates in human cells as shown in Examples 2 and 5 and has a folding with small energetic cost which results in good thermodynamic stability for the folded state as shown in example 5. In the illustration of FIG. 10, the construct of FIG. 9 is shown with an indication of possible chemical modifications directed to increase stability of the construct and activation efficiency following binding of an RNA activating signal to the toehold segment. In particular, 2'-O-methyl nucleotides in the indicated positions increase thermodynamic stability and nuclease resistance for the INACTIVE state and increase stability of toehold binding to the signal polynucleotide. The 3' terminus of the signal binding toehold has and inverted dT modification to increase exonucleases resistance and prevent spurious binding to the PAZ domain of Dicer. The C3 linker in the indicated position minimizes interference of the 5' overhang from interfering with Dicer processing in the ACTIVE state, as shown in example 4. The C3 linker, in conjunction with adjacent 2'-O-methyl and phosphorothioate modifications on the same strand, prevents 5' exonucleases degradation from proceeding beyond the overhang into the targeting domain.

In the activation: displacement duplex, it is preferred that thermodynamically stabilizing modifications are made to the side that binds the signal polynucleotide. This ensures the thermodynamic and kinetic favorability of binding to the correct signal polynucleotide.

In the illustration of FIG. 3 to FIG. 8, upon processing of the activation segment (5) in the active conformation of the molecular construct, the targeting binding domain (100) is presented in a conformation suitable to be processed by an enzyme of the RNAai inactivation pathway. In particular, in the targeting domain illustrated in FIGS. 3 to 8, processing is expected to be performed by Dicer in combination with an argonaute enzyme of the RNAi inactivation pathway. In variants where the targeting domain has a different length (e.g. 19 to 22 bp) processing of a targeting domain in an unfolded form and in particular within a construct in active conformation according to the present disclosure can be performed by one or more argonaute enzymes.

Figure 11:
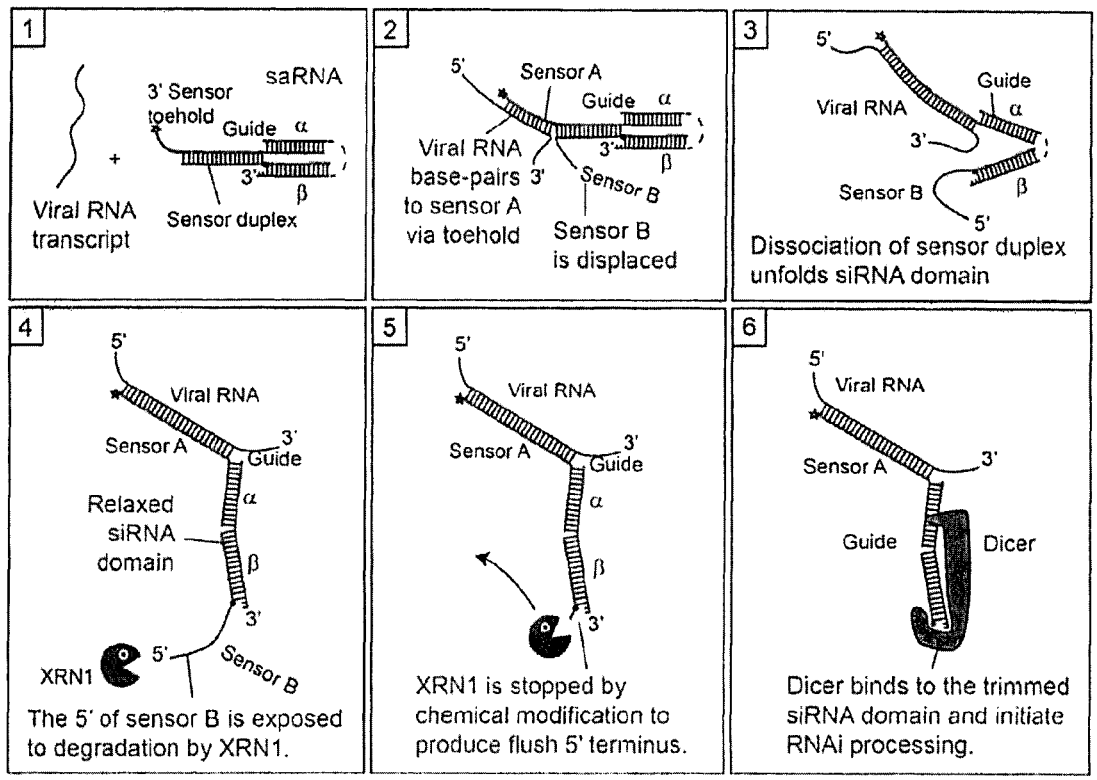

A schematic representation of an exemplary switching of a construct herein described from an inactive to active form and subsequent processing of the targeting domain by an RNAai inactivation pathway enzyme is illustrated in FIG. 11. In particular in the illustration of FIG. 11, a molecular construct is provided in an inactive form together with a suitable signal polynucleotide in the form of a viral RNA transcript (FIG. 11, frame 1), upon binding of the viral RNA transcript to the toehold of the construct the displacement segment is displaced from the activation segment (FIG. 11, frame 2) to provide an activated construct in which the toehold segment and the displacement segment are complementary bound to the viral RNA transcript and the targeting domain is released in an unfolded conformation (FIG. 11, frame 3). In the construct in active conformation of FIG. 11, the activation segment of the locking sensor is presented as a single strand at the 5' terminus of the targeting domain for binding to a XRN1 enzyme (FIG. 11, frame 4) which degrades the activation segment up to the 5' end of the targeting domain (FIG. 11, frame 5) thus providing a targeting domain in an unfolded conformation suitable to be processed by Dicer or other suitable enzyme of the RNAai inactivation pathway (FIG. 11, frame 6). Variations of the method schematically illustrated in FIG. 11, will be identifiable by a skilled person upon reading of the present disclosure.

For example, in addition to having different configuration of the constructs, modifications can be performed to increase the stability and/or the efficient processing of the activated construct through RNAai activity. In particular additional process steps to increase RNAi activity can comprise reduction of long 5' and 3' overhangs near the PAZ binding domain of the RNAi substrate (3' end of the Guide strand) inhibit Dicer processing as will be understood by a skilled person. Additional suitable approaches to improve RNAi activity on the targeting domain comprise: i) increase the flexibility of the linker between the overhang and the RNAi substrate by using a non-nucleic acid linker; ii) allowing an exonuclease to degrade the overhang and using chemical modifications to stop the exonuclease at a specific point; and/or iv) creating an endonuclease domain (e.g., a RNAse H domain) to allow clipping of the overhang by an endonuclease.

Figure 12:
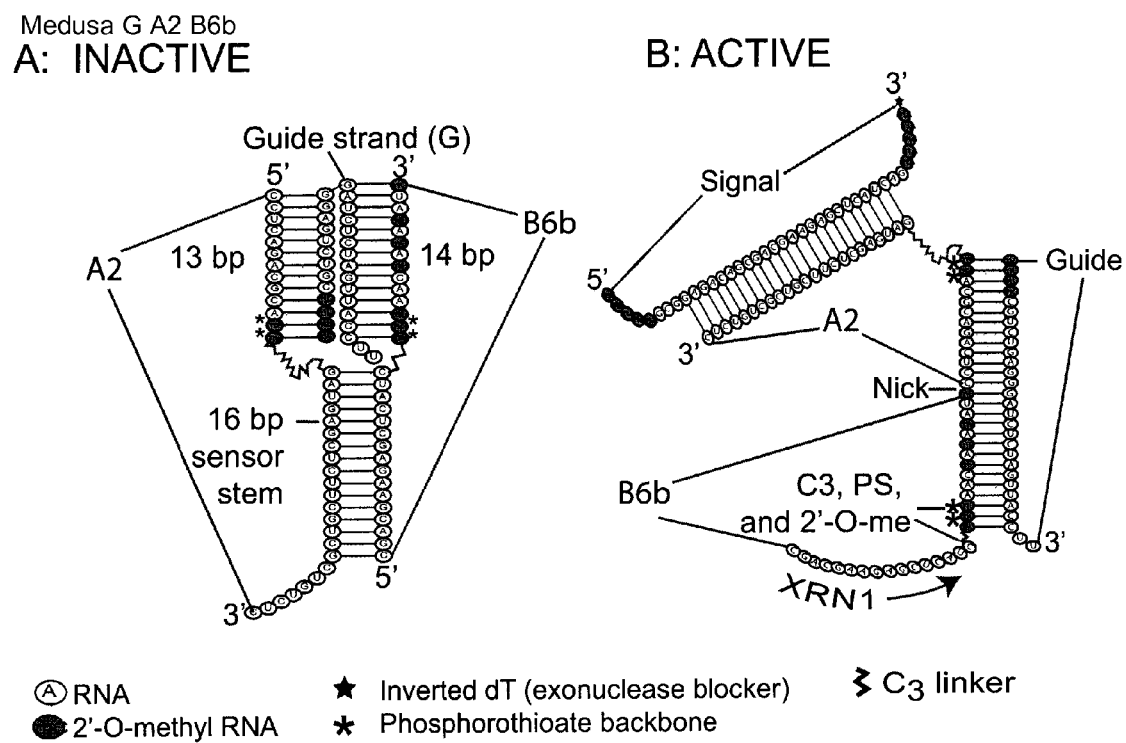
Figure 13:
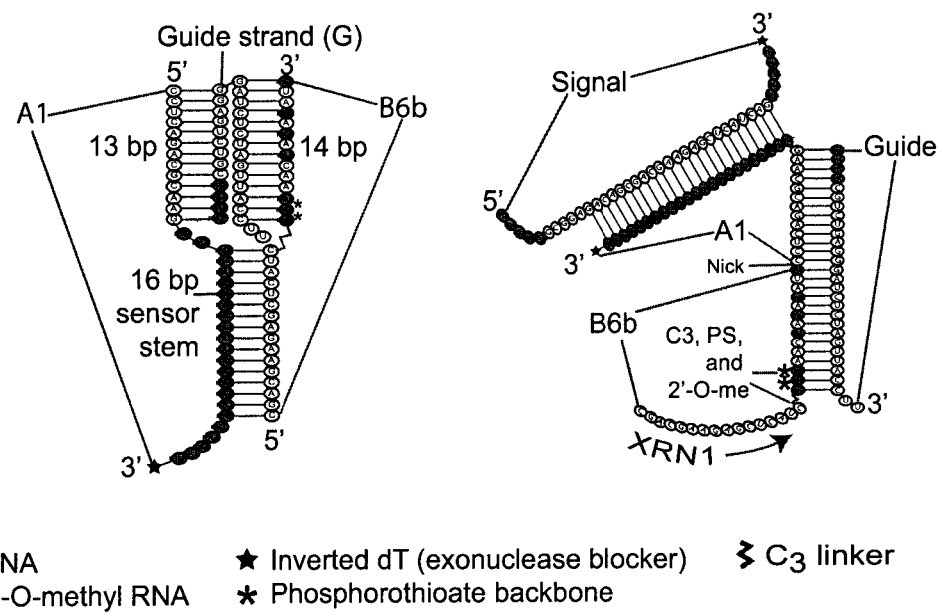
Figure 14:
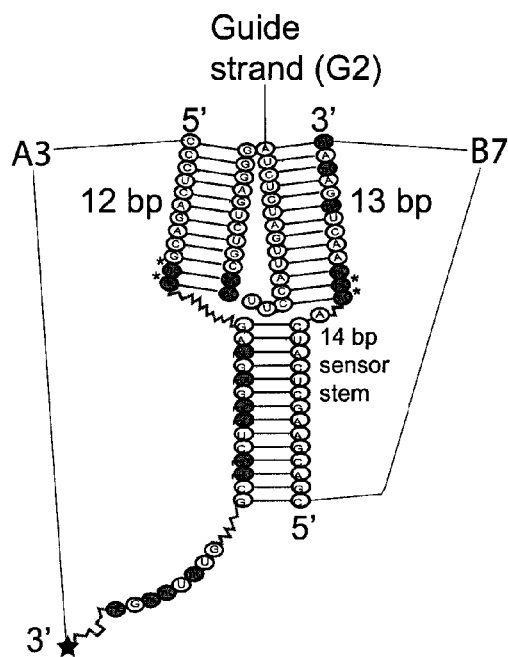
Figure 14:
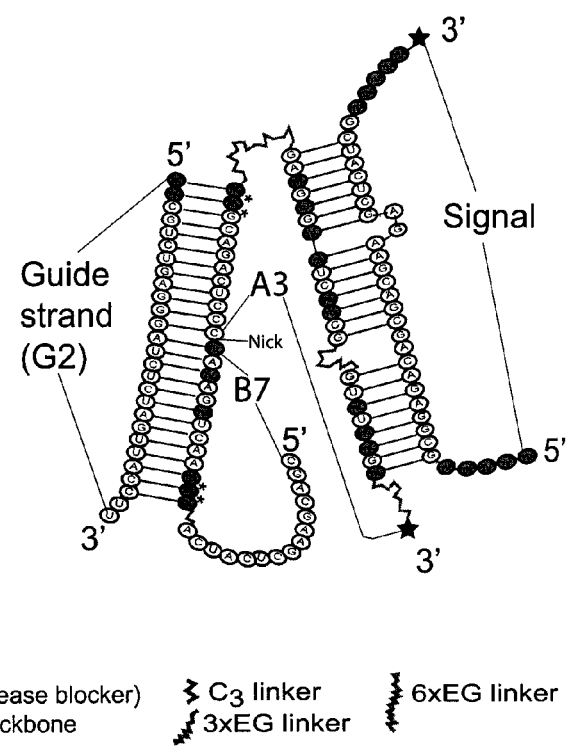

The illustration of FIGS. 12 to 15 show possible constructs modified to increase efficiency of RNAai activity following switch of an XRN1 based construct from an inactive conformation (OFF conformation) to an active conformation (ON conformation). In particular, FIG. 12 shows an XRN1 activated version with reduced turn OFF. FIG. 13 shows an XRN1 activated version with turn OFF improved using 2'-O-me modifications to stabilize sensor stem. FIG. 14 shows an XRN1 activated version with ON/OFF activity ratio improved by adding features to reduce PKR recognition resulting in a less stable duplex RNA.

In some embodiments, in the locking sensor herein described the activation segment can comprise a DNA portion and an RNA portion, the DNA portion of the activation segment complementary to the RNA portion of the activation segment. In those embodiments, when the displacement segment is displaced from the activation segment the DNA portion of the activation segment complementarily binds the RNA portion of the activation segment to provide an RNAase H binding site presented for binding.

Figure 15:
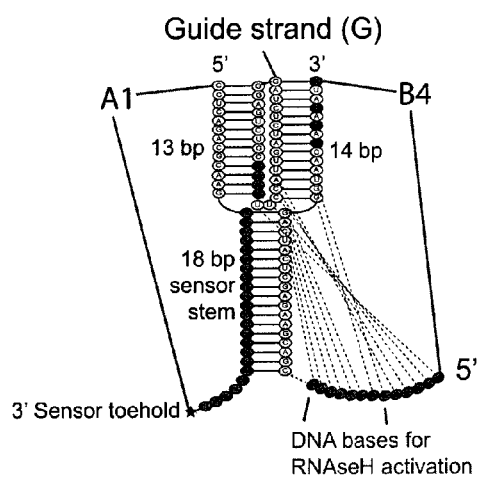
Figure 15:
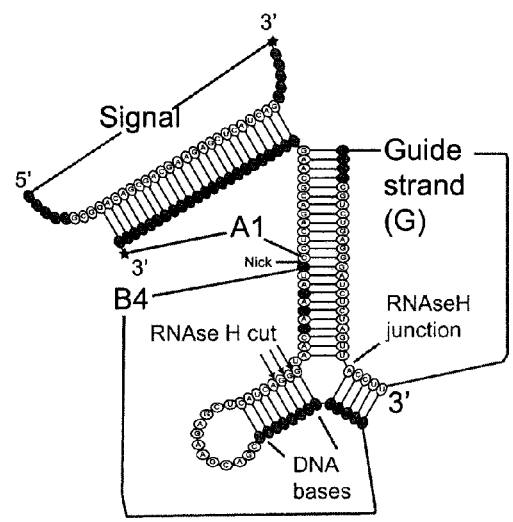

Reference is made to the illustration of FIG. 15 wherein an exemplary embodiment of the RNAase H activated design is described. In particular, in the illustration of FIG. 15, panel A the activation segment is shown to comprise a DNA portion at the 5' terminus configured in connection with the remaining portion of the activation segment so that upon displacement of the displacement segment, the such DNA portion complementary binds to RNA portions of the activation segment forming a three-way activation junction (see FIG. 15, panel B). This kind of junction can have a melting temperature of at least about 15° C. In particular, in some embodiments, a three-way activation junction such as the one illustrated in FIG. 15, panel B can comprise a DNA:RNA duplex of at least 5 consecutive base pairs that is composed of unmodified nucleotides. In embodiments in which the activatable constructs herein described comprise a targeting domain that is activated by RNAaseH based design, selection of the sequences is to be performed so that in absence of the signal molecule, the complementary binding between RNA portions of the activation segment and the displacement segment is thermodynamically more stable of the complementary binding of the RNA portion of the activation segment with the DNA portion of the activation segment. Also the configuration is such that upon binding of the signal molecule to the toehold segment and consequent displacement of the displacement segment from the activation segment, the RNA portion of the activation segment complementary binds the DNA portion of the same segment in a thermodynamically stable three way junction.

The melting temperature of the three-way activation junction of an activated construct such as the one exemplified in FIG. 15, panel B can be experimentally tested or measured using standard methods after removing the displacement segment from the construct. In this particular, embodiment, formation of the three-way activation junction is associated to the correct placement of the DNA:RNA duplex, and hence, positioning of the cleavage site of RNAse H in the construct. Possible variations of this structure can be envisioned by a skilled person in view of the present disclosure. For example, phosphorothioate backbone modifications can be applied to the DNA activation sequence to enhance DNA stability without affecting RNAse H activity. The strand melting temperature (Tm) of the activation junction can be experimentally tested or measured (see e.g. Examples 6 to 8).

The illustration of FIG. 15 illustrates an exemplary sensor locked siRNA design that utilizes RNAse H activation domain to remove the 5' overhang. The guide strand is 29 nucleotides long with 13 base pairs and 14 base-pairs complementary to the two pieces of the passenger strand. On the left is the inactive domain. The 3' and 5' extensions of the passenger strands form an 18 base pair sensor duplex. The 3' sensor toehold is 5 nucleotides on.

In the targeting domain, the 5' of the guide strand is modified with 2'-O-methyl bases to increase thermodynamic stability and nuclease resistance. The rest of the guide strand is unmodified to avoid interference with RISC functioning. The passenger side contains interspersed 2'-O-methyl bases to increase thermodynamic stability.

In the sensor, the side of the sensor which binds to the activation signal is entirely 2'-O-methyl to increase nuclease resistance, thermodynamic stability, and avoid destabilization by RNA chaperone proteins. The 3' terminus of the sensor toehold has an inverted dT modification to inhibit binding of Dicer to the sensor stem. The sensor stem is also kept below 19 base pairs to avoid Dicer processing. The 5' extension of the sensor stem is responsible for formation of the RNAse H processing domain. In addition to the DNA bases, the RNA bases in the 5' extension are 2'-O-methyl modified to increase nuclease resistance.

Figure 16:
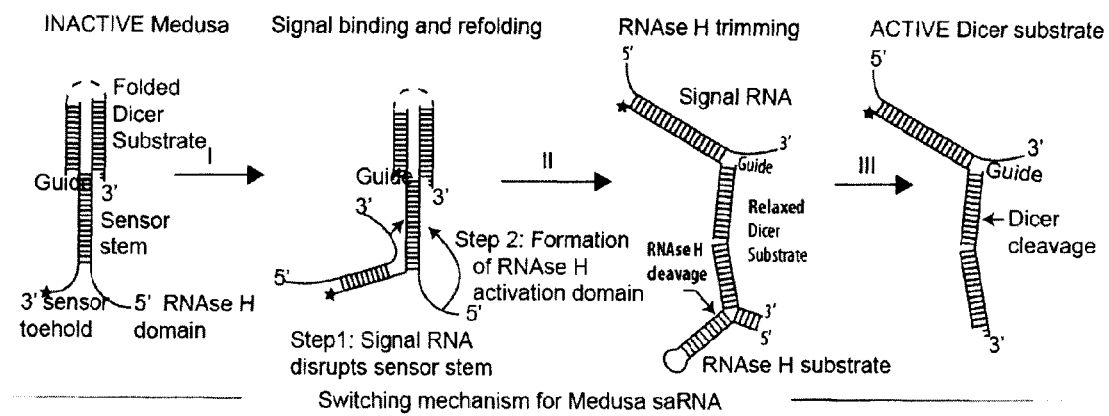

In the configuration of activatable constructs based on the RNAase H activated design according to factors to considered comprise: i) specific secondary and tertiary structure of the construct; ii) thermodynamic and kinetic stability in the presence of RBPs; iii) spurious processing; iv) PKR sensing; v) nuclear vs. cytoplasmic trafficking; vi) nuclease degradation; v) signal binding; vi) signal background; and/or vii) RNAi pathway processing as will be understood by a skilled person In the illustration of FIG. 16 an activation process for RNAse H activated construct is shown In particular an inactive construct is provided (Medusa in FIG. 16, panel A) which is then contacted with a signal polynucleotide (arrow I of FIG. 16) for signal binding and consequent displacement of the displacement segment from the activation segment (FIG. 16, panel B) and resulting switch of the construct from the inactive conformation to the active form (arrow II of FIG. 16) which is then subjected to reaction with RNAaseH (FIG. 16, panel B) for release of the targeting domain of the construct in an active form (arrow III of FIG. 16) for processing by Dicer or other enzyme of the RNAai pathway (FIG. 16, panel D).

In the construct of FIG. 16, panel D as well as in other constructs herein described (see e.g. FIGS. 3 to 10) in which the active form presents an activated targeting domain for processing with Dicer or other enzyme of the RNAai pathway, the activated domain binds at the end opposite to the one presenting the activated targeting domain, a signal duplex formed by the toehold segment and the displacement segment and the signal polynucleotide. In some of those embodiments, modifications of residues of the displacement segment and/or activation segment can be performed to increase efficiency of the RNAai processing of the activated targeted domain as will be understood by a skilled person.

For example, the thermodynamic stability of toehold binding to the activation signal can be increased via incorporation of 2'-O-methyl bases or locked nucleic acid (LNA) bases.

The exemplary illustrations of FIGS. 17 to 18 show possible constructs modified to increase efficiency of RNAai activity following switch of an RNAaseH based construct from an inactive conformation to an active conformation. In particular, FIG. 17 shows a construct in which the nucleotides of the toehold segment and displaced segment are 2-O-methyl ribonucleotides to increase stability of the construct and minimize unwinding of the locking sensor duplex RNA in absence of a signal complementary molecule. FIG. 18 shows an additional construct where portions of the displacement segments and the targeting domain comprise 2-O-methyl modified ribonucleotides and an inverted dT can be incorporated at the 3'-end of an oligo, leading to a 3'-3' linkage which inhibits both degradation by 3' exonucleases and extension by DNA polymerase. A further modification of the residues of the duplex is introduction of phosphorothioate linkage to protect the oligo from nuclease degradation as will be understood by a skilled person. In the illustration of FIG. 18 a C3 linker is also included in the target binding portion of the locking sensor to introduce unstructured linker to minimize activation of PKR degradation.

In the construct of FIG. 18 the 5' extension of the passenger strand can be degraded by XRN1 or another 5' exoribonuclease, or Dicer can interact with the targeting domain to process the guide strand without degradation of the 5' overhang (see also construct of FIG. 10). To allow this interaction, a C3 linker is placed at the position joining the 5' overhang to the passenger strand. In the ACTIVE state, the C3 linker serves two purposes. First, in case of exoribonucleolytic degradation of the 5' overhang, the C3 linker, in conjunction with adjacent 2'-O-methyl modifications and phosphorothioate backbone modifications, stops exoribonucleolytic processing. Second, the C3 linker gives extra flexibility prevent the 5' overhang from interfering with the processing of the targeting domain by Dicer. In the INACTIVE state, the C3 linker, along with the 2 un-paired bases on the opposite side of the sensor stem, connect the sensor stem to the targeting domain with sufficient slack to allow the structure to form correctly.

FIG. 19 schematically illustrates exemplary PKR interactions that can interfere with the stability and functionality of activatable constructs herein described herein provided for guidance purpose and are not intended to be limiting the scope of the present disclosure. A first set of interactions comprises exosome interactions in which the exosome binds onto the 3' tail degrades strand A of the illustrated construct or stably binds strand A of said construct (see FIG. 19, panel A). This type of interactions are verifiable by a skilled person for example degradation can be verified by Northern blot, and a strand A with PEG spacer to block degradation can also be tested by Northern blot as an additional verification. In particular in FIG. 19 panel A the 3' extension on sensor A extends the duplex just past the 30 bp limit for PKR activation in FIG. 19, panel B additional hypothesis for PKR is illustrated in which PKR binding excludes Dicer processing thus interfering with the RNAai activity.

Accordingly, a cellular immunity sensor for duplex RNA can: i) activate when two PKR proteins dimerize on minimal substrates of 28 to 30 bp; ii) be tolerant of mismatches; iii) Substrate needs to be coaxial; iv) A single mismatch every 8 bp reduces activation; v) activation can be suppressed by chemical modifications, but 2'-O-Me has no such function.

FIG. 20 shows exemplary variations to the basic structure of the targeting domain illustrated in its inactive conformation, and in particular small interfering RNA (siRNA), dicer substrate small interfering RNA (DsiRNA), synthetic miRNA analogues (miRNA). In particular in the illustration of FIG. 19: the siRNA is 17b to 19 bp with symmetric 2 nt 3' overhangs and is therefore not processed by Dicer (first panel); DsiRNA is equal to or longer than 19 bp to allow Dicer processing equal to or lower than 30 bp to avoid cellular toxicity and is processed by Dicer; the shRNA is similar to DsiRNA but in a hairpin form and is processed by Dicer; the miRNA is roughly 17 bp to 30 bp RNA hairpins; mismatches and bulges; and is processed by Dicer or Dicer free pathways. Exemplary sensor locked siRNA are shown in FIGS. 10 and 18.

Although only polynucleotide targeting domains are shown in the illustration of FIGS. 1 to 20 and in other figures of the present disclosure, in various embodiments of signal activatable construct herein described a targeting domain can comprise a molecule other than RNA or a polynucleotide configured to be delivered to a target with the cells in the presence of the signal polynucleotide. Exemplary types of cargo molecule that can be comprised in all or in part as a targeting domain according to the current disclosure include but are not limited to peptides, small, molecules aptamers, antibodies, and other chemical compound identifiable by a person skilled in the art.

In those embodiments, the targeting domain formed by the cargo molecule or attaching the cargo molecule, can be carried and delivered by constructs herein described wherein the segments of the sensor domain are arranged in various configurations which allow switching of the construct from an inactive conformation to an active conformation with respect to the enzyme assisted release of the targeting domain as will be understood by a skilled person upon reading of the present disclosure. For example in embodiments, wherein the targeting segment is configured for delivery of a cargo molecule, the cargo molecule can be covalently linked to the 3' terminus of the passenger strand or to the 5' of the guide strand for targeting domain of 25 bp or longer. In those embodiments wherein the cargo molecule comprises a cargo such as a polynucleotide aptamer, the cargo molecule can be non-covalently attached to the construct for example through complementarily binding to the 5' terminus of the guide strand segment of the targeting domain or other base pairing segment linked to the displacement segment in a configuration that does not interfere with the binding of the signal molecule and allows release of the cargo with the displacement segment following RNAai processing of the guide strand. In particular, in some of the embodiments wherein a duplex formed between the cargo molecule and the passenger strand segment of the targeting domain or other base pairing segment, the duplex can have a melting temperature of at least 15° C.

Signal activatable constructs and related components herein described can be designed and manufactured based on techniques described herein and/or identifiable by the skilled person upon reading of the present disclosure. In particular the configuration of the segments of the constructs can be identified and designed based on calculation of the thermodynamic stability of the various conformation of the segments and constructs as a whole. For example, thermodynamic stability of polynucleotide conformation dependents on several factors identifiable by a skilled person, including its i) chemical composition (for example, DNA:RNA duplex is less than RNA:RNA duplex); ii) base composition (for example, G/C base paring is more stable than A/T base paring, which is approximately as stable as G/T, G/U wobble base pairing, and the formation of a stable RNA hairpin requires at least 3 G/C base pairs or at least 5 A/U, G/U base pairs); iii) nearest neighbors such as presence of mismatches, open ends, and junctions near a base-pair can substantially influence its energy contribution according to the second-nearest neighbor model (for example, the stacking of successive base-pairs is primarily responsible for the stability of DNA helices); iv) non-canonical base pairing (for example, RNA and DNA can form triple helix and quadraplex structures via Hoogsteen base-pairing, which is less stable base pairings than canonical base pairing); v) Geometry (e.g. polynucleotide sequences can only adopt secondary structures that are geometrically consistent or similar with the known tertiary structural characteristics of RNA and DNA helices); vi) Environmental factors, such as pH value, counter-ion concentration and temperature and additional factors identifiable by a skilled person.

Accordingly, designing the polynucleotide sequences comprised in the signal activatable construct can be performed identifying the combination of length, sequence, complementarity and substitutions that is associated with a desired relative thermodynamic stability resulting in the configuration herein described and the environment wherein the enzyme assisted molecular delivery is desired. For example, in several embodiments, in absence of a signal polynucleotide, an inactive conformation of the signal activatable construct typically has approximately 3 extra G/C base pairs or 5 extra A/U or G/U base pairs as compared to the activated conformation formed in presence of the signal polynucleotide. Specific sequences of desired signal polynucleotides can be identified by a skilled person based on environment (and in particular, specific cells and tissues) where delivery is desired. Also, the number of complementary base pairs between the protection segment and displacement segment is typically more than that between the protection segment and the activation segment. For applications where molecular delivery in cells is desired, polynucleotide sequences can be designed according to the corresponding physiological conditions, such as approximately, pH 7.3-7.4, about 150 millimolar potassium or sodium chloride or equivalent salt, and about 37° C.

For base pairing between unmodified DNA segments or between unmodified RNA segments, the base-pairing energies and the most stable secondary structure conformations can be estimated by computational methods known to and well established in the art. Several packages are available and published in documents also discussing in detail factors affecting the energy and stability of nucleic acid secondary structures. Exemplary publications describing the packages and factore comprise for i) *NUPACK web server*: J. N. Zadeh, et al., (2011); ii) *NUPACK analysis algorithms*: R. M. Dirks et al., (2007); R. M. Dirks et al., (2003); R. M. Dirks et al., (2004); iii) *NUPACK design algorithms*: J. N. Zadeh et al., (2011); iv) *mfold web server*: M. Zuker, (2003); A. Waugh et al., (2002); M. Zuker et al., (1998); v) *UNAFold & mfold*: N. R. Markham et al., (2008); M. Zuker, et al., (1999); M. Zuker, (1994); J. A. Jaeger et al., (1990); M. Zuker, (1989); vi) *Free energies for RNA*: D. H. Mathews et al., (1999); A. E. Walter et al., (1994); vii) *Methods and theory of RNA secondary structure prediction*: D. H. Mathews et al., (2007); D. H. Mathews et al., (2006); D. H. Mathews et al. $3^{rd}$ edition, John Wiley & Sons, New York, Chapter 7, (2005); D. H. Mathews et al., (2004); M. Zuker, (1984); M. Zuker et al., (1981) D. H Mathews et al (2010); viii) *Exemplary mfold & UNAFold applications*: J.-M. Rouillard et al., (2003); J.-M. Rouillard, et al., (2002). In addition, since some polynucleotide structures typically fluctuate between an ensemble of secondary structure conformations, the composition of the relevant ensemble can be determined using computational methods known in the art (see for example, see Ye Ding et al., (2005), herein incorporated by reference in its entirety).

Accordingly, in several embodiments, design of a polynucleotide sequence of the sensor domain of the signal activatable construct herein described, can be performed for sequences or portions of sequences consisting of unmodified DNA and/or RNA base pairs, by computational methods and/or software packages to calculate the free energy of the sequence and the secondary structure conformation. In embodiments, wherein polynucleotide sequences comprise derivatives of nucleotides, such as chemically modified bases and analogues, and/or chimeric polynucleotide sequences composed of a mixture of deoxyribonucleotides and ribonucleotides, design can be performed by computationally designing unmodified RNA structures with the desired secondary structure conformations and thermodynamic stability, and then introducing one or more chemical modifications to achieve the desired thermodynamic stability. Exemplary chemical modifications comprise replacement of nucleotides that are needed to be base-paired to form a desired secondary structure with modified nucleotides that are known to increase thermodynamic stability (e.g. 2'-O-methyl modified nucleotides, LNA, PNA and Morpholino). Additional exemplary modifications comprise replacement of nucleotides that are not desired according to a certain thermodynamic stability with modified nucleotides to ensure that the resulting modified structures are likely to retain the desired secondary structure conformations and thermodynamic stability (e.g. replace a ribonucleotide base with a deoxyribonucleic base). A person skilled in the art will be able to identify other suitable modifications upon reading of the current disclosure.

The signal activatable construct designed according the present disclosure can be synthesized using standard methods for oligonucleotide synthesis well establish in the art, for example, see Piet Herdewijn, (2005), herein incorporated by reference in its entirety.

The synthesized oligonucleotide can be allowed to form its secondary structure under a desirable physiological condition, (e.g. 1× phosphate buffered saline at pH 7.5 with 1 mmolar concentration $MgCl_2$ at 37° C.). The formed secondary structure can be tested using standard methods known in the art such as chemical mapping or NMR. For example, see Stephen Neidle, (2008), herein incorporate by reference in its entirety. The designed construct can be further modified, according to the test result, by introducing or removing chemical modifications, mismatches, wobble pairings, as necessary, until the desired structure is obtained.

In some embodiments, in presence of a signal polynucleotide, the free energy of the construct in an activated conformation is at least about 5 kcal/mol lower than that of the construct in an inactive conformation.

In some embodiment, the free energy of complementary base-paring between the protection segment and the displacement segment is at least about 10 kcal/mol lower that the free energy of complementary base-paring between the DNA activation sequence and the RNA activation substrate.

In some embodiment, the targeting domain comprises a first segment and a second segment, wherein the first segment and the second segment form a polynucleotide duplex through complementarily binding with each other; and the 3' terminus of the second segment is adjacently connected with the protection segment of the sensor domain both segments.

In some embodiments, the guide strand, passenger strand, activation segment, displacement segment and toehold segment of the signal activatable construct are mainly composed of RNA and/or RNA derivatives.

The term "derivative" as used herein with reference to a first compound (e.g. RNA or ribonucleotide) indicates a second compound that is structurally related to the first compound and is derivable from the first compound by a modification that introduces a feature that is not present in the first compound while retaining functional properties of the first compound. Accordingly, a derivative of a molecule of RNA, usually differs from the original molecule by modification of the chemical formula that might or might not be associated with an additional function not present in the original molecule. A derivative molecule of RNA retains however one or more functional activities that are herein described in connection with complementary base paring with other nucleotides. Typically, ribonucleotides and deoxyribonucleotides can be modified at the 2', 5', or 3' positions or the phosphate backbone chemistry is replaced. Exemplary chemical modifications of a ribonucleotide according to the current disclosure include 2'-o-methyl RNA, 2'-Fluoro RNA, locked nucleic acid (LNA), peptide nucleic acid (PNA), morpholino, phosphorothioate oligonucleotides, and the like that are identifiable by a skilled person (see e.g. "Modified Nucleosides: in Biochemistry, Biotechnology and Medicine. Piet herdewijn (Editor), Wiley-VCH, 2008, herein incorporated by reference in its entirety). Also applicable are nucleosides which are not normally comprised in DNA and RNA polynucleotides, such as inosine. In some embodiments, a single oligonucleotide can be composed of more than one type of the above derivatives.

In particular, according to several embodiments herein described, the guide strand and passenger strand of the targeting domain comprise unmodified ribonucleotides. In other embodiments, the guide strand and passenger strand of the targeting domain can comprise modified ribonucleotides, such as 2'-O-methyl modification, 2'-fluoro modification, 2'-amino modification or LNA; the exposed 5' terminus of the passenger strand can have modifications configured to minimize processing by the XRN1. For example, 5' terminus of the passenger strand can have at least 1, and in particular 2 2-O-methyl ribonucleotide. Similarly the 3' terminus of the guide strand can have modifications configured to block processing by the endonucleases enzyme Dicer. For example, 3' terminus of the first segment can have at least 1, and in particular 2 deoxyribonucleotides. In some embodiments, the protection segment can comprises unmodified ribonucleotides and/or some modified ribonucleotides, such as 2'-O-methyl modification, 2'-fluoro modification, 2'-amino modification or LNA. In particular, in some embodiments, the two nucleotides immediately flanking the desired RNAse H cleavage site within the RNA activation sequence can be formed by unmodified ribonucleotides.

In some embodiments, the activation segment comprises a DNA activation sequence formed by unmodified deoxyribonucleotides. In particular in some of these embodiments the construct is an RNAaseH based construct.

In some embodiments, the displacement segment and the toehold segment can comprise modified ribonucleotides or derivatives, such as 2'-O-methyl modification, 2'-fluoro modification, 2'-Amino modification or LNA; the exposed terminus of the toehold segment can also have modifications configured to block processing by endonucleases enzyme Dicer. For example, the exposed terminus of the toehold segment can comprise at least one, and in particular two, phosphorothioate deoxyribonucleotides.

In several embodiments, the toehold segment can comprise a polynucleotide sequence (herein also toehold sequence) that is at least 3 nucleotides in length and is fully complementary to at least a portion of the signal polynucleotide. This configuration of the toehold segment is expected to allow binding of a signal polynucleotide to bind to the signal activatable construct and initiate the branch migration process. A smaller toehold sequence is expected to result in better sequence specificity for signal discrimination, while a longer toehold sequence is expected to result in an increased ability to bind to the signal polynucleotides to form a desired secondary structure with respect to the ability of a shorter toehold segment. In some embodiments, the toehold segment can be arranged in single-stranded form and free of secondary structure. In particular, in some of those embodiments, the toehold sequence can be 4 to 12 nucleotides in length. In some embodiments, the toehold segment is composed of unmodified ribonucleotide. In particular, in other embodiments, the toehold segment comprises modified nucleotide configured for improved nuclease resistance. Exemplary modifications include but are not limited to 2'-O-methyl modification, 2'-Fluoro modifications, inclusions of LNA and PNA, and the like that are identifiable by a skilled person.

In some embodiments, the signal can be a single signal polynucleotide of a length shorter than 30 nucleotides, the toehold segment and the displacement segment is fully complementary to the signal polynucleotide. In other embodiments, the signal can be formed by multiple homologous signal polynucleotides. In these embodiments, the signal polynucleotides can be tested with a sensor design. Mismatches and wobble pairings or permissive bases such as inosine can be placed at positions in the 3:5 duplex corresponding to the variable sequences. In particular, in several embodiments, the Tm for the duplex formed by the signal polynucleotides with the toehold segment and the displacement segment is typically at least 25° C. and is typically at least equal to the operating temperature under which the construct will be used. In some embodiments, the 3' terminus of the sensor domain can have Dicer blocking groups which are identifiable by a skilled person.

In some embodiments, where the toehold segment is arranged as or within a single-stranded loop (see exemplary embodiments in FIG. 4, panel C, FIG. 5, panel C and FIG. 7, panel C), the loop can be sufficiently large to avoid topological constraints that present a kinetic barrier to displacement of the activation segment from binding to the displacement segment by the signal polynucleotide. To test whether the loop is as large as desired, the strand displacement process of the construct can be tested using the methods such as the one described in Example 8. Further, in some embodiments the signal polynucleotide used in the experiment, can be selected to approximate the expected state of the signal in the cell. In particular, in embodiments wherein the signal polynucleotide is expected to be a short oligonucleotide or RNA segment, such as a miRNA, a short oligonucleotide of the same sequence as the signal polynucleotide can be used in experiments to simulate the topological constraints imposed by having the toehold segment in a hairpin loop. In embodiments wherein the signal is an mRNA sequence, a polynucleotide having the same sequence as the mRNA as the signal nucleotide can be used to simulate the topological constraints imposed by having the toehold segment in a hairpin loop. In embodiments wherein the region known to bind to the toehold segment is in a hairpin loop, the signal nucleotide used in the displacement experiment can have the toehold sequence in a hairpin loop to simulate the topological constraints imposed by having the toehold segment in a hairpin loop.

In embodiments wherein strand displacement does not occur, the size of the hairpin loop can be increased to decrease the topological constraint by increasing the loop size. For example, in some embodiments, the size can be increased using an unstructured polynucleotide or polymer linker between the toehold segment and the other segments (e.g. either between the toehold segment and the activation segment or, usually less favorably, between the toehold segment and the displacement segment). In particular in various embodiments, the loop can have at least about 20 unstructured nucleotides.

Single stranded regions in the hairpin loop and in other areas can be protected by chemical modifications if not conflicting with other design objectives. 2'-O-methyl, 2'-fluoro, LNA, 2'-amino and other modified RNA nucleosides can replace RNA. Phosphorothioate deoxyribonucleotides can replace unmodified deoxyribonucleotides for RNAseH segment.

In some embodiment, wherein the locking sensor comprises more than one polynucleotide the melting temperature of the duplex formed by the displacement segment and the activation segment is at least 5° C. above the expected operating temperature under which the construct is used, (e.g. 37° C. for the use in human cells) in order to prevent spurious activation.

In some embodiments, the toehold segment can be connected to the displacement segment through covalent linkage. In particular, in some embodiments, the toehold segment can be arranged to the 3' terminus of the displacement segment (see exemplary embodiments in FIGS. 3 to 5). In some embodiments, the toehold segment can be arranged as a single strand terminal sequence of the sensor domain; in other embodiments, the toehold segment can be provided as a single strand middle sequence of the sensor domain, which can be arranged within a loop structure of the sensor domain. In particular, in some embodiments, where the toehold domain can be arranged within a loop structure of the sensor domain, the loop can comprise at least 20 nucleotide unmodified nucleotides, which in some cases can be ribonucleotides. In some embodiments, the toehold segment can be at least 3 nucleotides in length. In particular, in some embodiments, the toehold segment can be at least 4 nucleotides in length.

In some embodiments, the activation segment can be kept to the minimum length necessary for efficient formation of an activation junction to kinetically minimize spurious activation usually associated with binding of a large terminal loop in the sensor domain to a partially deprotected activation site as a result of partial displacement of (5) by a partially complementary polynucleotide that is not the intended signal polynucleotide. Accordingly, the activation segment can be at least 5 nucleotides in length, and in particular less than 10 nucleotides in length. Additional lengths of the loop can be identified by a skilled person taking into account that the possibility of having complementary binding of a strand to the loop that result in displacement of the displacement segment from the activation segment in view of a desired experimental design Alternatively, in some embodiments, the toehold segment links the 3' terminus of the activation segment and the 5' terminus of the displacement segment, and is arranged as a loop between the activation segment and the displacement segment, (see e.g. FIGS. 3, 4, 5 and 7. In particular, FIG. 3, panel C shows a schematic illustration of the signal activatable construct in an inactive conformation, where the toehold segment (segment 7) is arranged at the 3' terminus of protection segment (segment 6) and the 5' terminus of the displacement segment (segment 5), and is located in the loop of a stem-loop structure formed by the activation segment and the displacement segment. FIG. 3, panel D shows schematic illustration of an activated conformation of the signal activatable construct according to the embodiment as shown in FIG.

3, panel C. In this activated conformation, portions (1) and (3) form a double-stranded duplex through base paring, portions (2), (4) form a double-stranded base pairing, and together they form the activated targeting domain.

In some embodiments, in absence of a signal polynucleotide, the displacement segment and the protection segment form a double-stranded duplex. In particular, the double-stranded duplex formed by the displacement segment and the protection segment can have up to 30 consecutive base pairs, if the duplex comprises only unmodified ribonucleotides. In other embodiments, the double-stranded duplex formed by the displacement segment and the protection segment can be longer than 30 base pairs, if the duplex comprises mismatches and/or modified ribonucleotides. In particular, mismatches and/or modifications are expected to contribute to preventing activation of innate immune system and/or increase stability. Exemplary modifications to the first and the second segments include but are not limited to 2'-O-methylation, 2'-Fluoro modifications, 2'-amino modifications, and inclusion of LNA or PNA nucleotides. In particular 2'-O-methylation can be used to passivate against innate immune activation. In some embodiments, the displacement segment is at least 12 nucleotides in length. In some embodiments, the displacement segment can be at least 14 nucleotides in length.

In some embodiments, the construct is configured to minimize immune responses. In these embodiments, each consecutive 30 base pairs duplex can have at least 5% 2'-O-methyl modifications (Molecular Therapy (2006) 13, 494-505, herein incorporated by reference in its entirety) or one or two mismatches. In other embodiments, the construct is configured to stimulate immune responses. In these embodiments, the construct can comprises at least one consecutive 30 base-pair duplex with no 2'-O-methyl modifications when the construct is in the activated conformation. For example, the total length of the toehold segment and the displacement segment can be at least 30 nucleotides without 2'-O-methyl modifications, and will be perfectly base paired with the signal polynucleotide sequence.

In some embodiments an activated conformation of the activatable construct herein described or related component (e.g. locking sensor), a DNA portion comprised in the activation segment (herein also DNA activation sequence or portion) binds to an RNA portion comprised in the protection segment (herein RNA activation sequence) through complementary base paring to form a RNAase H binding site.

In human cells, RNAse H commonly cleaves the RNA sequence of a DNA:RNA duplex at a position that is 5 nucleotides from the 5' end of the RNA sequence forming the duplex. If the duplex is longer than 7 base pairs, RNAse H can cleave at additional positions to the 3' of the first cleavage site. Accordingly, the DNA:RNA duplex formed in the activated conformation according to the current disclosure can be at least 5 nucleotides, and in particular 7-8 nucleotides. In particular, in some embodiments, the DNA activation sequence is no longer than 10 nucleotides. In particular, in several embodiments, an RNAase H cleavage site comprises a DNA:RNA duplex of at least 5 consecutive base pairs, in particular, the DNA:RNA duplex has 7 consecutive base pairs. In some embodiments, cleavage rate is expected to increase if 8 or more consecutive base pairs are present in the duplex, but there will be multiple cleavage sites. Higher Tm of the DNA:RNA duplex is expected to generally improve cleavage efficiency. In some embodiments, Tm can be greater than or equal to the expected operating temperature. For example, when working at room temperature, Tm can be about 25° C. or more. In another example when operating in human cells, Tm can be 37° C. or more. In particular, Tm can be not lower than about 15° C. In the DNA:RNA duplex, deoxyribonucleotides can be replaced with phosphorothioate deoxyribonucleotides. The nucleotides flanking the DNA activation sequence in the activation segment can be unmodified ribonucleotides to keep the highest RNAase cleavage efficiency. Alternatively, flanking nucleotides can also be modified ribonucleotides, such as 2'-O-methyl ribonucleotides, 2'-Fluoro ribonucleotides, or LNA.

FIG. 16 shows the products of RNAse H cleavage of the activated signal activatable construct according to the embodiment shown in FIG. 16. A double-stranded RNA molecule is released from a remanent. The released double-stranded RNA molecule is bound to the signal molecule on one terminus and has at least 2-base single-stranded overhang at the 3' of the toher terminus and therefore can be used as a siRNA or a suitable substrate for Dicer. Other exemplary embodiments can be also found in FIGS. 15 and 17.

In some embodiments, the sensor domain is configured to avoid immune activation in the cell, wherein the sensor domain forms a double strand duplex with the signal polynucleotide of no longer than about 30 bp. In other embodiments, the sensor domain is configured to induce immune activation in the cell, wherein the sensor domain forms a double strand duplex with the signal polynucleotide of longer than about 30 bp.

In some embodiments where the double-stranded duplex formed by the displacement segment and the protection segment is longer than 16 base pairs, and in particular, the exposed 3' terminus of the double-stranded duplex comprises modifications configured to block processing of Dicer.

In some embodiments, the guide strand is configured to interfere with a target intracellular process of the cells through RNAi in presence of the signal polynucleotide. Accordingly suitable targeting domain include siRNA, microRNA and additional duplex structure suitable to be used in connection with RNA interfering.

The term "RNA interfering" or "RNAi" as used herein refers to a mechanism or pathway of living cells that controls level of gene expression that has been found in many eukaryotes, including animals. The RNAi pathway has many important roles, including but not limited to defending cells against parasitic genes such as viral and transposon genes, directing development and regulating gene expression in general. The enzyme Dicer, which is an endoribonuclease in the RNAse III family, initiates the RNAi pathway by cleaving double-stranded RNA (dsRNA) molecules into short fragments of dsRNAs about 20-25 nucleotides in length. Dicer contains two RNase III domains and one PAZ domain; the distance between these two regions of the molecule is determined by the length and angle of the connector helix and determines the length of the siRNAs it produces. Dicer cleaves with the highest efficiency dsRNA substrates 21 bp and longer with a two-base overhang at the 3' end.

The small fragments of dsRNAs produced by Dicer are known as small interfering RNA (siRNA). The term "small interfering RNA" or "siRNA", sometimes also known as short interfering RNA or silencing RNA, refers to a class of dsRNA molecules which is typically 20-25 nucleotides in length and plays a variety of roles in biology. The most notable role of siRNA is its involvement in the RNAi pathway. In addition to its role in the RNAi pathway, siRNA also acts in RNAi-related pathways, including but not limited to several antiviral pathways and shaping chromatin structure of a genome.

Each siRNA is unwound into two single-stranded (ss) ssRNAs, namely the passenger strand and the guide strand. The passenger strand is degraded, while the guide strand is incorporated into a multiprotein complex, known as the RNA-induced silencing complex (RICS). RICS uses the incorporated ssRNA as a template for recognizing a target messenger RNA (mRNA) molecule that has complementary sequence to the ssRNA. Upon binding to the target mRNA, the catalytic component of RICS, Argonaute, is activated, which is an endonuclease that degrades the bound mRNA molecule.

Similar to siRNAs, microRNAs (miRNAs) also mediate the RNAi pathway. The term "microRNA" or "miRNA" as used herein indicates a class of short RNA molecules of about 22 nucleotides in length, which are found in most eukaryotic cells. miRNAs are generally known as post-transcriptional regulators that bind to complementary sequences on target mRNA transcripts, usually resulting in translational repression and gene silencing.

miRNAs are encoded by miRNA genes and are initially transcribed into primary miRNAs (pri-miRNA), which can be hundreds or thousands of nucleotides in length and contain from one to six miRNA precursors in hairpin loop structures. These hairpin loop structures are composed of about 70 nucleotides each, and can be further processed to become precursor-miRNAs (pre-miRNA) having a hairpin-loop structure and a two-base overhang at its 3' end.

In the cytoplasm, the pre-miRNA hairpin is cleaved by the RNase III enzyme Dicer. Dicer interacts with the 3' end of the hairpin and cuts away the loop joining the 3' and 5' arms, yielding an imperfect miRNA:miRNA duplex about 22 nucleotides in length. Overall hairpin length and loop size influence the efficiency of Dicer processing, and the imperfect nature of the miRNA:miRNA base pairing also affects cleavage. Although either strand of the duplex can potentially act as a functional miRNA, only one strand is usually incorporated into RICS where the miRNA and its mRNA target interact.

In those embodiments, wherein the guide strand is configured for interfering a target intracellular process through RNAi, the double-stranded duplex typically formed by the guide strand and passenger strands can have a melting temperature (Tm) of at least about 25° C. In particular, the 5' terminal nucleotide of the guide strand can be base paired to one of the passenger strands. In some embodiments, nicked double-stranded duplex formed by the guide strand and passenger strands are stable under conditions of the environment where delivery will be performed. In embodiments where RNAi is performed in mammals the nicked double-stranded duplex typically formed by the guide strand and passenger strand can have a melting temperature (Tm) of at least about 37° C.

In some embodiments, a double-stranded polynucleotide duplex with a 3' overhang of 2 nucleotides in length is most efficiently bound by the PAZ domain of the endonucleases enzyme Dicer (Jin-Biao Ma, et al, 2004). In human cells, RNAse H commonly cleaves the RNA sequence of a DNA:RNA duplex at a position that is 5 nucleotides from the 5' end of the RNA sequence forming the duplex. If the duplex is longer than 7 base pairs, RNAse H can cleave at additional positions to the 3' of the first cleavage site. Accordingly, in embodiments using an RNAse H substrate, the DNA:RNA duplex formed in the activated conformation according to the current disclosure is at least 5 nucleotides, and in particular 7-8 nucleotides.

In those embodiments where the targeting domain is configured to interfere with a target intracellular process of the cells through RNAi, the first segment and the second segment are at least 16 nucleotides in length. In particular, in some embodiments, they are no short than 22 nucleotides. In particular, in some embodiments, the second segment is at least 2 nucleotides longer than the first segment. Accordingly, in some embodiment, the double-stranded duplex formed by the first segment and second segment has a 2-base single strand overhang at the 3' terminus of the second segment.

In particular, in some embodiments, the double-stranded duplex formed by the first segment and the second segment are no longer than 30 consecutive base pairs, if the duplex comprises only unmodified ribonucleotides. In other embodiments, the double-stranded duplex formed by the first segment and the second segment can be longer than 30 base pairs, if the duplex comprises mismatches and/or modified ribonucleotides. The mismatches and/or modifications are likely to prevent activation of innate immune system. Exemplary modifications to the first and the second segments include but are not limited to 2'-O-methylation, 2'-Fluoro modifications, 2'-amino modifications, and inclusion of LNA or PNA nucleotides. In particular, 2'-O-methyl, 2'Fluoro, 2'amino, LNA and PNA are expected to improve stability of the structure.

Further, in these embodiments, at least one at least one strand of the duplex is configured for interfering a target intracellular process through RNAi. In some embodiments, the at least one strand is at least partially complementary to a target gene sequence for silencing that gene through RNAi. In other embodiments, the at least one strand is at least partially complementary to a common sequence shared by multiple genes or members of a gene family. In other embodiments, the at least one strand is configured to be incorporated into a protein complex to activate the complex and/or the substrate of the complex or to initiate a cascade of activation of downstream effectors of the complex. In some embodiments, from 2 to 8 bases of the at least one strand incorporated into RISC is complementary with a target gene forming a "seed region" usually considered particularly important for RNAi activity as will be understood by a skilled person.

According to several embodiments, the duplex formed by the guide strand and the passenger strand has a blunt end at the 3' end of the guide strand. The duplex formed by the first segment and the second segment is at least 21 bp long. In particular, the first 21 nucleotide from the 3' terminus of the guide strand is configured for interfering a target intracellular process through RNAi, and the $21^{st}$ and $22^{nd}$ 5' terminus of the first segment and from the 3' terminus of the second segment are unmodified RNA nucleotides so as to allow efficient Dicer processing after signal activation of the signal activatable construct.

In other embodiments, the 3' terminal region of segments other than the guide strand comprises modifications to inhibit RNAi loading pathway enzyme processing from the 3' terminus of the first segment. In particular, in some embodiments, the last at least 1 base at the 3' terminal region of the first segment is a DNA modified DNA base. In particular, the last 2 nucleotides at the 3' terminal region of the first segment is a DNA modified DNA base. In other embodiments, the 3' terminal region of segment 1 is chemically modified. Exemplary modifications includes but are not limited to 3'-O-propanediol modifications, 3'-O-fluorescin modifications, 3'-puromycin modifications, 3'-inverted dT modifications, inverted Dideoxy-T modifications and the like that are identifiable by a skilled person in the art.

In some embodiments, the double-stranded duplex formed by the activation and displacement segments have additional modifications at the 3' terminus of segment 7 and/or the 5' terminus of segment 5 to further prevent processing of the inactivate construct by RNAi loading pathway enzymes, such as Dicer. In some embodiments, (see FIG. 6, panel C) the 3' terminus of segment 7 has additional secondary structures, such as a terminal polynucleotide hairpin with 4-15 bp long stem. In some embodiments, the 3' terminus of segment 7 is connected with a synthetic polynucleotide structure, such as a DNA or RNA multi-crossover tile, a DNA or RNA origami, a DNA or RNA crystal, and other structures identifiable by a person skilled in the art.

In particular, in some embodiments, at least one of the passenger segments and the guide segment comprises a sequence homologous to an endogenous microRNA sequence. More particularly, in some embodiment, the first segment and the second segment have the exact same sequence and structure as a known or predicted mammalian pre-miRNA. In some embodiments, at least one of the t passenger segments and the guide segment has the same sequence as a known or predicted mammalian miRNA. In some embodiments, the double-stranded duplex formed by the passenger and guide segments comprises mismatches and/or bulges configured to mimic a known or predicted mammalian miRNA. In some embodiments at least one of the passenger segments or guide segment is homologous to the sequence of a known or predicted mammalian miRNA. The term "homologous" or "homology" used herein with respect to biomolecule sequences as indicates sequence similarity between at least two sequences. In particular, according to the current disclosure, a homologous sequence of a mammalian miRNA can have the same sequence located at base position 2-7 from the 5' terminus of the guide strand of the miRNA.

In some embodiments, the targeting domain is configured to deliver a cargo molecule other than a polynucleotide in the presence of the signal polynucleotide. In these embodiments, the targeting domain can also comprise a double-stranded polynucleotide duplex as part of the cargo. Reference is made to the constructs illustrated in The term "aptamers" as used here indicates oligonucleic acid or peptide molecules that bind a specific target. In particular, nucleic acid aptamers can comprise, for example, nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Aptamers are useful in biotechnological and therapeutic applications as they offer molecular recognition properties that rival that of the antibodies. Peptide aptamers are peptides that are designed to specifically bind to and interfere with protein-protein interactions inside cells. In particular, peptide aptamers can be derived, for example, according to a selection strategy that is derived from the yeast two-hybrid (Y2H) system. In particular, according to this strategy, a variable peptide aptamer loop attached to a transcription factor binding domain is screened against the target protein attached to a transcription factor activating domain. In vivo binding of the peptide aptamer to its target via this selection strategy is detected as expression of a downstream yeast marker gene The term "small molecule" as used herein indicates an organic compound that is of synthetic or biological origin and that, although might include monomers and/or primary metabolites, is not a polymer. In particular, small molecules can comprise molecules that are not protein or nucleic acids, which play a biological role that is endogenous (e g inhibition or activation of a target) or exogenous (e.g. cell signaling), which are used as a tool in molecular biology, or which are suitable as drugs in medicine. Small molecules can also have no relationship to natural biological molecules. Typically, small molecules have a molar mass lower than 1 kg·mol$^{-1}$. Exemplary small molecules include secondary metabolites (such as actinomicyn-D), certain antiviral drugs (such as amantadine and rimantadine), teratogens and carcinogens (such as phorbol 12-myristate 13-acetate), natural products (such as penicillin, morphine and paclitaxel) and additional molecules identifiable by a skilled person upon reading of the present disclosure.

The terms "peptide" and "oligopeptide" usually indicate a polypeptide with less than 50 amino acid monomers, wherein the term "polypeptide" as used herein indicates an organic linear, circular, or branched polymer composed of two or more amino acid monomers and/or analogs thereof. The term "polypeptide" includes amino acid polymers of any length including full length proteins and peptides, as well as analogs and fragments thereof. As used herein the term "amino acid", "amino acidic monomer", or "amino acid residue" refers to any of the twenty naturally occurring amino acids, non-natural amino acids, and artificial amino acids and includes both D an L optical isomers. In particular, non-natural amino acids include D-stereoisomers of naturally occurring amino acids (these including useful ligand building blocks because they are not susceptible to enzymatic degradation). The term "artificial amino acids" indicate molecules that can be readily coupled together using standard amino acid coupling chemistry, but with molecular structures that do not resemble the naturally occurring amino acids. The term "amino acid analog" refers to an amino acid in which one or more individual atoms have been replaced, either with a different atom, isotope, or with a different functional group but is otherwise identical to original amino acid from which the analog is derived.

In an embodiment, a targeting domain can be attached to a locking sensor herein described with methods and approaches identifiable by a skilled person. In particular, attachment can be performed at a portion of the protection domain configured for binding the targeting domain (e.g. presenting a suitable functional group) and presented for binding in the sensor domain. The term "attach" or "attached" as used herein, refers to connecting or uniting by a bond, link, force or tie in order to keep two or more components together, which encompasses either direct or indirect attachment where, for example, a first molecule is directly bound to a second molecule or material, or one or more intermediate molecules are disposed between the first molecule and the second molecule or material. The term "present" as used herein with reference to a compound or functional group indicates attachment performed to maintain the chemical reactivity of the compound or functional group as attached. Accordingly, a functional group presented on a segment, is able to perform under the appropriate conditions the one or more chemical reactions that chemically characterize the functional group. Exemplary target binding portion herein described comprise a monomer presented in the 5' terminus of the protection domain. A skilled person will be able to identify additional suitable portions, including intermediate compound or functional groups used to covalently attach the targeting domain with the protection domain at any suitable portion. In particular the target binding portion of the protection segment and the activation domain are typically attached of the RNA portion of the protection segment.

In some embodiments, a system for intracellular information processing and controlling of cells is described. The system comprising two or more signal activatable constructs as described for simultaneously combined or sequential use in the cells, in which the targeting domain of at least one construct of the two or more constructs is configured to release a second signal in the presence of the signal polynucleotide, and the second signal is configured to activate one or more construct of the two or more constructs.

In some embodiments, one or more signal activatable constructs and/or component thereof including sensor domains can be used in a method for XRN1 or RNAse H assisted signal activated molecular delivery in cells. The method comprises delivering to the cells an effective amount of one or more of the signal activatable construct described herein possibly preceded by contacting the sensor domain with a suitable targeting domain to provide the construct.

In some embodiments, RNA and DNA nanostructures herein described can allow specific biomolecules to trigger specific changes in their secondary, tertiary and quaternary structure. These characteristics are comprised in several embodiments of activatable constructs herein described as will be understood by the skilled person to develop novel switching mechanisms that work with endogenous nucleases to activate or release therapeutic cargo.

In one embodiment, a sensor gated siRNA can be provided with selectively activated RNAi activity in cells expressing a specific RNA sequence. The activating sequence switches ON the siRNA by binding to its sensor domain and triggering internal conformational changes that induce processing by endogenous RNAse H or XRN1. The result is an active Dicer substrate that can direct targeted RNAi.

As disclosed herein, the signal activated constructs and related components herein described can be provided as a part of systems for enzyme assisted molecule delivery, including any of the deliveries described herein. The systems can be provided in the form of kits of parts. In a kit of parts, the signal activated constructs and related components and other reagents to perform enzyme-assisted delivery can be comprised in the kit independently. The signal activated constructs and related components can be included in one or more compositions, and each construct or component can be in a composition together with a suitable vehicle.

Additional components can include labeled molecules and in particular, labeled polynucleotides, labeled antibodies, labels, microfluidic chip, reference standards, and additional components identifiable by a skilled person upon reading of the present disclosure. The terms "label" and "labeled molecule" as used herein as a component of a complex or molecule referring to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" as used herein indicates the signal emitted from the label that allows detection of the label, including but not limited to radioactivity, fluorescence, chemiluminescence, production of a compound in outcome of an enzymatic reaction and the like.

In some embodiments, detection of molecule delivery can be carried either via fluorescent based readouts, in which the labeled antibody is labeled with fluorophore, which includes, but not exhaustively, small molecular dyes, protein chromophores, quantum dots, and gold nanoparticles. Additional techniques are identifiable by a skilled person upon reading of the present disclosure and will not be further discussed in detail.

In particular, the components of the kit can be provided, with suitable instructions and other necessary reagents, in order to perform the methods here described. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like)

In some embodiments, one or more signal activated constructs and/or related components, (e.g. sensor domain) herein described are comprised in a composition together with a suitable vehicle. The term "vehicle" as used herein indicates any of various media acting usually as solvents, carriers, binders or diluents for signal activated constructs and related components that are comprised in the composition as an active ingredient. In particular, the composition including the signal activated constructs and related components can be used in one of the methods or systems herein described.

In some embodiments, a composition for XRN1 and/or RNAse H assisted signal activated molecular delivery in can comprise one or more of the signal activatable construct as described together with a suitable vehicle. In some embodiments, the vehicle is suitable for delivering the signal activatable construct to cells. Exemplary suitable vehicles according to the current disclosure include but are not limited to nanoparticle, such as cyclodextrin, gold nanoparticle and dendrimer; liposome and liposome analogues; conjugated aptamer; conjugated antibody; conjugated cell penetrating peptide or peptide analogue; carbon nanotubes; conjugated fatty acids and quantum dots.

In some embodiments, the signal activated constructs and related components herein described are comprised in pharmaceutical compositions together with an excipient or diluent.

The term "excipient" as used herein indicates an inactive substance used as a carrier for the active ingredients of a medication. Suitable excipients for the pharmaceutical compositions herein described include any substance that enhances the ability of the body of an individual to absorb the signal activated constructs and related components herein described or combinations thereof. Suitable excipients also include any substance that can be used to bulk up formulations with the peptides or combinations thereof, to allow for convenient and accurate dosage. In addition to their use in the single-dosage quantity, excipients can be used in the manufacturing process to aid in the handling of the peptides or combinations thereof concerned. Depending on the route of administration, and form of medication, different excipients can be used. Exemplary excipients include, but are not limited to, antiadherents, binders, coatings, disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluents include any substance that can decrease the viscosity of a medicinal preparation.

In particular, in some embodiments, disclosed are pharmaceutical compositions which contain at least one signal activated constructs and related components as herein described, in combination with one or more compatible and pharmaceutically acceptable vehicles, and in particular with pharmaceutically acceptable diluents or excipients. In those pharmaceutical compositions the signal activated constructs and related components can be administered as an active ingredient for treatment or prevention of a condition in an individual.

The term "treatment" as used herein indicates any activity that is part of a medical care for, or deals with, a condition, medically or surgically.

The term "prevention" as used herein indicates any activity which reduces the burden of mortality or morbidity from a condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

The term "condition" as used herein indicates a physical status of the body of an individual (as a whole or as one or more of its parts), that does not conform to a standard physical status associated with a state of complete physical, mental and social well-being for the individual. Conditions herein described include but are not limited disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms.

The wording "associated to" as used herein with reference to two items indicates a relation between the two items such that the occurrence of a first item is accompanied by the occurrence of the second item, which includes but is not limited to a cause-effect relation and sign/symptoms-disease relation.

The term "individual" as used herein in the context of treatment includes a single biological organism, including but not limited to, animals and in particular higher animals and in particular vertebrates such as mammals and in particular human beings.

For example in some embodiments, a multi-stage therapeutic nanoparticles can be provided that utilize XRN1 and/or RNAaseH activated release of a cargo in a cell to achieve controlled step-wise disassembly and cargo release in target environment such as solid tumor micro environments.

A skilled person will be able to identify further application and in particular therapeutic applications as well as cargo molecules to be used as active agents in the treatment and design a corresponding signal activatable construct to be administered according to the features of the construct and the desired effect. In particular, in applications wherein signal activatable construct is desired system administration of the agent can be performed. In embodiments, where an activated construct is instead used, topical administration to the specific target cell and tissue can be performed.

Further advantages and characteristics of the present disclosure will become more apparent hereinafter from the following detailed disclosure by way or illustration only with reference to an experimental section.

EXAMPLES

The synthesized signal activatable constructs herein disclosed are further illustrated in the following examples, which are provided by way of illustration and are not intended to be limiting.

The following material and methods were used in the experiments illustrated in the following examples.

Northern Blot Analysis:

HCT116 cells were transfected using with the indicated Medusa complexes or controls at a final concentration of 1 nMolar with pBluescript (pBS) as carrier, using Lipofectamine2000 according to the manufacturer's (Invitrogen) protocol. The cell medium (American Type Culture Collection, recommended formulation) was replaced at 18 hours post-transfection. Total cell RNA was harvested using RNASTAT60 (amsbio) according to the manufacturer's instructions, except for the addition of a 1:1 phenol:chloroform pH 6.7 extraction prior to precipitation. For Northern analysis, 15 ug of total RNA in 1× formamide loading buffer was run on a 10% urea/PAGE gel, using $^{32}$P-end-labeled Ambion Decade size markers. The RNA was transferred to Hybond XL (Amersham) using the BioRad TransBlot SD (semi-dry) cell. Transferred RNA was cross-linked to the membrane using the UV Stratalinker 2400 (Stratagene) pre-set conditions. Membranes were prehybridized 6-10 hours at 37 degrees Celsius with Perfeethyb Plus (Sigma) and hybridized in the same buffer overnight at 37 degrees Celsius with 5-10 pmoles of $^{32}$P-end-labeled oligo probes as shown. After 2×SSC/1% SDS washes at 37 Celsius, the membranes were exposed using Kodak BioMax film and intensifying screens at −80 C and developed according to the manufacturer's instructions.

Transfections for Luciferase Analyses:

HCT116 cells were transfected using with the indicated exemplary activatable complexes or controls at a final concentration of 1 nMolar with pBluescript (pBS) as carrier, using Lipofectamine2000 according to the manufacturer's (Invitrogen) protocol. The cell medium was replaced at 18 hours post-transfection. One day before transfection, cells were seeded in growth medium without antibiotics so that cells would reach 90-95% confluency at the time of transfection (as recommended by Invitrogen protocols). Each well was transfected with a final DNA mix consisting of: 40 nanograms (ng) psiCHECK (Promega) plasmid bearing a Firefly luciferase (Fluc) control reporter and a *Renilla* luciferase (Fluc) reporter with the target in the 3' UTR; 120 ng pBluescript carrier DNA; and an amount of Medusa complex 10× with respect to the final concentration indicated in the specific experiment in a 20 ul final volume ($\frac{1}{10}$ th the final) of OptiMEM (Invitrogen). An equal volume of a $\frac{1}{50}$ dilution of Lipofectamine2000 in OptiMEM was added (bringing the volume to $\frac{1}{5}$ th the final) and incubated according to the manufacturer's instructions. The liposome/DNA complexes were added, along with fresh complete medium to the cells to give a final volume of 200 ul. Total cell RNA was harvested using RNASTAT60 (amsbio) according to the manufacturer's instructions, except for the addition of a 1:1 phenol:chloroform pH 6.7 extraction prior to precipitation. To reduce sample to sample variability, the psiCHECK target mix was made in batch and aliquoted to allow 3 technical replicates (wells) for each condition. The Medusa complexes were diluted to the appropriate concentration in OptiMEM with the Lipofectamine2000 dilution (also made in batch). Two complete sets of triplicates were run per experiment: one using and psiCHECK vector without the U5 siRNA target (as a check for non-target specific knockdown) and a second using the psiCHECK with the U5 siRNA target in the *Renilla* luciferase 3' UTR. After transactions, samples were collected for luciferase analysis.

Example 1

Exemplary Activatable Constructs

Exemplary molecular constructs were provided having the features summarized in Tables 1 and 2 below.

TABLE 1

RNA Complexes and Component Strands

| Complexes Abbreviation | Sequences | SEQ ID NO: |
|---|---|---|
| G Ac Bc | | |
| G | mC mU mU mG C G U C U G A G G G A U C U C U A G U U A C C U U | 1 |
| Ac | C C U C A G A C G C A A G idT | 2 |
| Bc | G G U A A C U A G A G A U C | 3 |
| G RP | | |
| G | mC mU mU mG C G U C U G A G G G A U C U C U A G U U A C C U U U | 1 |
| RP | C C U C A G A C G C A A G G G U A A C mU A mG A mG A U mC | 4 |
| G | mC mU mU mG C G U C U G A G G G A U C U C U A G U U A C C U U U | 1 |
| A1 | C C U C A G A C G C A A G mC mU mG mA mU mG mA mG mC mU mC mU mU mC mG mU mC mG mC mU mG mU mU idT | 5 |
| B1 | mA mA mG mG mU dC dC dC dT dG dA dT C G A C G A A G A G C U C A U C A G G G U A A C U A G A G A U C | 6 |
| G | mC mU mU mG C G U C U G A G G G A U C U C U A G U U A C C U U | 1 |
| A1 | C C U C A G A C G C A A G mC mU mG mA mU mG mA mG mC mU mC mU mU mC mG mU mC mG mC mU mG mU mU idT | 5 |
| B4 | mA mA mG mG mU dC dC dC dT dG dA dT C G A C G A A G A G C U C A U C A G G G U A A C mU A mG A mG A U mC | 7 |
| G A1 B6b | | |
| G | mC mU mU mG C G U C U G A G G G A U C U C U A G U U A C C U U | 1 |
| A1 | C C U C A G A C G C A A G mC mU mG mA mU mG mA mG mC mU mC mU mU mC mG mU mC mG mC mU mG mU mU idT | 5 |
| B6b | C G A C G A A G A G C U C A U C _-_ C3 _-_ mG * mG * mU A A C mU A mG A mG A U mC | 8, 9 § |
| G2 A3 B7 | | |
| G2 | mC mG C G U C U G A G G G A U C U C U A G U U A C C U U | 10 |
| A3 | C C C U C A G A C G mC * mG * _-18S-_ G A mU G mA G-- mC mU U C mG mU C G _-9S-_ G U mC U mC mC G mC 9S idT | 11, 12, 13 § |
| B7 | C G A C G A A G C U C A U C A _-_ C3 _-_ mG * mG * mU A A C U mA G A mG A mU | 14, 15 § |
| tat activator strand | | |
| S | mA mA mA mA mA G C G G A G A C A G C G A C G A A G A G C U C A U C A G mA mA mA mA mA idT | 16 |
| G Ac Bc | | |
| G | mC mU mU mG C G U C U G A G G G A U C U C U A G U U A C C U U | 1 |
| Ac | C C U C A G A C G C A A G idT | 2 |
| Bc | G G U A A C U A G A G A U C | 3 |

TABLE 1-continued

RNA Complexes and Component Strands

| Complexes Abbreviation | Sequences | SEQ ID NO: |
|---|---|---|
| G RP | | |
| G | mC mU mU mG C G U C U G A G G G A U C U C U A G U U A C C U U U | 1 |
| RP | C C U C A G A C G C A A G G G U A A C mU A mG A mG A U mC | 4 |
| G | mC mU mU mG C G U C U G A G G G A U C U C U A G U U A C C U U U | 1 |
| A1 | C C U C A G A C G C A A G mC mU mG mA mU mG mA mG mC mU mC mU mU mC mG mU mC mG mC mU mG mU mU idT | 5 |
| B1 | mA mA mG mG mU dC dC dC dT dG dA dT C G A C G A A G A G C U C A U C A G G G U A A C U A G A G A U C | 6 |
| G | mC mU mU mG C G U C U G A G G G A U C U C U A G U U A C C U U | 1 |
| A1 | C C U C A G A C G C A A G mC mU mG mA mU mG mA mG mC mU mC mU mU mC mG mU mC mG mC mU mG mU mU idT | 5 |
| B4 | mA mA mG mG mU dC dC dC dT dG dA dT C G A C G A A G A G C U C A U C A G G G U A A C mU A mG A mG A U mC | 7 |
| G A1 B6b | | |
| G | mC mU mU mG C G U C U G A G G G A U C U C U A G U U A C C U U | 1 |
| A1 | C C U C A G A C G C A A G mC mU mG mA mU mG mA mG mC mU mC mU mU mC mG mU mC mG mC mU mG mU mU idT | 5 |
| B6b | C G A C G A A G A G C U C A U C - C3 - mG * mG * mU A A C mU A mG A mG A U mC | 8, 9 § |
| G2 A3 B7 | | |
| G2 | mC mG C G U C U G A G G G A U C U C U A G U U A C C U U | 10 |
| A3 | C C C U C A G A C G mC * mG * -18S- G A mU G mA G-- mC mU U C mG mU C G -9S- G U mC U mC mC G mC 9S idT | 11, 12, 13 § |
| B7 | C G A C G A A G C U C A U C A - C3 - mG * mG * mU A A C U mA G A mG A mU | 14, 15 § |
| tat activator strand | | |
| S | mA mA mA mA mA G C G G A G A C A G C G A C G A A G A G C U C A U C A G mA mA mA mA mA idT | 16 |

§ Sequences connected by a linker as indicated in the Sequences column

In particular, Table 1 indicates for each exemplary molecular construct the specific sequences of the strands that are complementary bound to provide the molecular constructs, herein described. The corresponding configuration is illustrated in FIGS. 21-32 each identifying the construct by the corresponding abbreviation.

Additional features of the complexes listed in table 1 are summarized in Table 2

TABLE 2

Complexes and component strand features

| Complex Name | Abbreviation | # nt | Description | Sequence 5' -> 3' | Notes | SEQ ID NO: |
|---|---|---|---|---|---|---|
| Medusa guide 29mer | G or G1 | 29 | U5K2 targeting guide strand for the medusa | mC mU mU mG C G U C U G A G G A U C U C U A G U U A C C U U | | 1 |
| Medusa sensor A binds to act strand | A or A1 | 37 | Sensor A version 1 for medusa | C C U C A G A C G C A A G mC mU mG mA mU mG mA mG mC mU mC mU mU mC mG mU mC mG mC mU mG mU mU idT | | 5 |
| Medusa sensor B with RNAse H activation | B1 | 44 | Sensor B version 1 for medusa | mA mA mG mG mU dC dC dC dT dG dA dT C G A C G A A G A G C U C A U C A G G G U A A C U A G A G A U C | overlapping 586, 585 and senB LNA homologies | 6 |
| Medusa passenger A control | Ac | 14 | Truncated sensor A strand for medusa control, 3' end of passenger (together with Bc, homologous to guide) | C C U C A G A C G C A A G idT | | 2 |
| Medusa passenger B control | Bc | 14 | Truncated sensor B strand for medusa control, homologous to 3' end of guide; with Ac homologous to entireity of guide | G G U A A C U A G A G A U C | | 3 |
| Tat 28 base act strand | S | 39 | Tat/Rev signal activator, 28 nt to fit extended toehold | mA mA mA mA mA G C G G A G A C A C G A C G A A G A G C U C A U C A G mA mA mA mA mA idT | overlapping 179, 585 homologies | 16 |
| Medu sen B V4 | B4 | 44 | Sensor B with 7 base DNA region shifted from 2 and 3 and extra 2'-o-me to stabilize act stem. RNAseH-activated, e.g in Ac Bv4 G | mA mA mG mG mU dC dC dC dT dG dA dT C G A C G A A G A G C U C A U C A G G G U A A C mU A mG A mG A U mC | overlapping 586, 585 and senB LNA homologies | 7 |
| Medusa reverse linked passenger strand | RP | 27 | Ac and Bc linked in reverse topology (3' of Ac is linked to 5' of Bc) | C C U C A G A C G C A A G G G U A A C mU A mG A mG A U mC | | 4 |

TABLE 2-continued

Complexes and component strand features

| Complex Name | Abbreviation | # nt | Description | Sequence 5' -> 3' | Notes | SEQ ID NO: |
|---|---|---|---|---|---|---|
| Medusa B v6a 18bp sensor | B6a | 32 | Sensor B, XRN1 5' removal, 18bp sensor | C G A C G A A G A G C U C A U C A G - C3 - mG * mG * mU A A C mU A mG A mG A U mC | overlapping 58S and senB LNA homologies | 17, 18 [S] |
| Medusa B v6b 16bp sensor | B6b | 30 | Sensor B, XRN1 5' removal, 16bp sensor | C G A C G A A G A G C U C A U C - C3 - mG * mG * mU A A C mU A mG A mG A U mC | overlapping 58S and senB LNA homologies | 8, 9 [S] |
| Medusa B v6 control | Bc6 | 14 | Bc, but with terminal C3 and phosphorothioates, and 2'-o-me to mimic truncated Bv6 products | C3 mG * mG * mU A A C mU A mG A mG A U mC | | 19 |
| Medusa H1 | H1 | 67 | | G A C A G C G A C G A A G G C G A C G G C C3 *mG * mG * U A A C U A G A G A U C 18S 18S C C U C A G A C G C A *mA *mG 18S G C C G U C G C A *G C U C* *A U C A G* idT | Clasp, 5' end homologous to middle of 179 (shown), the 3 5' end of 58S, and 3' end of J1 (-6 to -18, inclusive) and 3' end homologous to bases J1 5', 1-10 | 20, 21, 22, 23 [S] |
| Medusa Av2 | Av2 | 36 | | C C U C A G A C G C A *mA *mG 18S G A U G A G C U C U U C G U C G C U G U C U C | | 24, 25 [S] |
| Medusa G2 | G2 | 27 | non-methylated sequence same as G; G had 5' mC mU mU mG | mC mG C G U C U G A G G G A U C U C U A G U U A C C U U | | 14 |
| Medusa J2 | J2 | 27 | | 9S mC U mG A U mG A 9S mG mC U mC U mU C mG U_ 18S_mC G mC U mG U mC U mC mC 18S idT | | 26, 27, 28 [S] |
| Medusa A3 | A3 | 35 | | C C C U C A G A C G mC * mG * 18S G A mU G mA G -- mC mU C mG mU C G_9S G U mC U mC mC G mC 9S idT | CUGAUGAG CUCUUCGU CGCUGUCU CCGC -- GAUGAG-CUUCGUCG - GUCUCCGC Bubbled to interrupt continuous helix in portion indicated with double dash | 11, 12, 13 [S] (in sequence 5' -> 3' column), 2 9 (in Notes column) |

TABLE 2-continued

Complexes and component strand features

| Complex Name | Abbreviation | # nt | Description | Sequence 5' -> 3' | Notes | SEQ ID NO: |
|---|---|---|---|---|---|---|
| Medusa B7 | B7 | 28 | | C G A C G A A G C U C A U C A C3 mG * mG * mU A A C U mA G A mG A mU | overlapping 586, 585 and senB LNA homologies | 14, 15 [§] |

The wording 18S, 9S reported in bold fonts indicates PEG linkers.
[§] The sequences are connected by a linker as indicated in the sequence 5'_->3' column The probes used for detection of the construct are listed in Table 3 below.

TABLE 3

Probes for medusa constructs and related segments

| Name | Abbreviation | Description | Sequence | SEQ ID NO: | Detected sequence | SEQ ID NO: | Notes |
|---|---|---|---|---|---|---|---|
| Sensor A LNA Probe | | LNA probe for Medusa sensor A | CTT + GC + GTCTGAGG | 30 | CCUCAG ACGCAA G | 31 | |
| Sensor B LNA Probe | | LNA probe for Medusa sensor B | GA + TC + TCTAGT + TACC | 32 | GGUAAC UAGAGA UC | 33 | |
| RH3'TP1 | 541 | 3' toe passenger strand probe | CAGACTTTGTT GGATTTGAAA | 34 | UUUCAA AUCCAA CAAAGU CUG | 35 | |
| RH3'GP6.31 | 542 | 3' Toe Guide Probe 6-31 | CTTCAAGCCA GACTTTGTTGG ATTTG | 36 | CAAAUC CAACAA AUCUGG CUUGAA G | 37 | |
| RH3'GP51.72 | 543 | 3' Toe Guide probe 51-72 | ACAGCGACGA AGAGCTCATC AG | 38 | CUGAUG UGCUCU UCGUCG CUGU | 39 | |
| U5K2GPrb | 544 | Probe for HIV-1 U5K2 shRNA guide strand. cf 564 | GGTAACTAGA GATCCCTCAG A | 40 | (TCT)GA GGGAUC UCUAGU UACC | 41 | |
| Med1Sen A3'Pr | 584 | Probe for 3' end of Medusa 1 sensor A toehold region. | ACAGCGACGA AGAGCTCATC AG | 42 | CUGAUG AGCUCU UCGUCG CUGU | 43 | |
| Med1Sen BStPr | 585 | Probe for sensor stem of Medusa 1 RNAseH activation strand (sensor B). | CCCTGATGAG CTCTTCGTCG | 44 | CGACGA AGAGCU CAUCAG GG | 45 | |
| Med1Sen B5'Pr | 586 | Probe for 5' end of Medusa 1 RNAseH activation strand (sensor B). | CTTCGTCGATC AGGGTCCTT | 46 | AAGGAC CCUGAU CGACGA AG | 47 | |

Example 2

Stability of an Exemplary Activatable Construct

The G A1B4 construct was assembled by combining all three component strands at 1:1:1 and annealing per standard experimental procedures. The construct was then transfected at 1 nM concentration in to HCT 116 cells for 24 hours. After 24 hours, the cells were lysed and the RNA extracted for Northern Blot. Different probes are used to prove for the presence of the Guide (left), A1 (middle), and B4 (right) strands.

The results illustrated in FIG. 29 show the stability of the component strands of the locked siRNA constructs in human HCT116 cells. In particular, the results of these experiments show that each strand is present, with little detectable signs of degradation. This shows that each component strand of the G A1 B4 sensor locked siRNA is stable in human HCT116 cells for at least 24 hours.

Example 3

Confirmation of RNAai Processing of the Guide Strand in Exemplary Complexes by Luciferase Analysis To test successful release and processing of the guide strand from a targeting domain in an activated conformation of the exemplary molecular complexes of Example 1 Applicants performed dual Luciferase assays whose results are illustrated in FIG. 30.

In particular FIG. 30 shows functioning of the different implementations of the complexes in dual luciferase assays. In these dual Luciferase assays the ratio of *Renilla* Luciferase to Firefly Luciferase luminosity is compared to a negative control. A value of 1.0 signifies undetectable RNAi activity. A value of 0.0 constitutes perfect RNAi activity, meaning there is zero activity from the *Renilla* luciferase target of RNAi knockdown. In FIG. 30 panel D, a series of positive controls are used to show activity of the targeting domains.

Medusa control, also known as G Ac Bc (SEQ ID NO: 1, SEQ ID NO: 2, SEQ ID NO:3), is shown to have very good RNAi knockdown at all levels. G Ac B6c (SEQ ID NO: 1, SEQ ID NO: 2, and SEQ ID NO: 19) is a variant of Medusa control with 2'-O-methyl modifications, phosphoriothioate modifications and a C3 linker. It simulates the targeting domain of G A1 B6b (SEQ ID NO: 1, SEQ ID NO: 5, SEQ ID NO: 8 and SEQ ID NO: 9), shown in FIG. 10. This complex has less RNAi activity compared to Medusa control, but is still able to have significant and target specific RNAi knockdown of *Renilla* luciferase. When a 5' extension is added, as in G Ac B6b (SEQ ID NO: 1, SEQ ID NO: 2, SEQ ID NO: 8 and SEQ ID NO: 9), there is no impact on the RNAi activity compared with G Ac B6c (SEQ ID NO: 1, SEQ ID NO: 2, and SEQ ID NO: 19). This illustrates that the combination of C3 linker modification and 2'-O-methyl and phosphorothioate modifications added is effective in preventing the 5' overhang from interfering with correct Dicer processing of the targeting domain.

G Ac B4 mimics the targeting domain of G A1 B4. Although not as effective as G Ac B6b, it still has significant detectable RNAi activity against the *Renilla* luciferase target, illustrating that the RNAase H trimming mechanism of G A1 B1 and G A1 B4 is effective in allowing for proper processing of the targeting domain.

In particular, in panels A and B, the inactive and active forms of two RNAase H activated designs for the sensor locked siRNA are compared with positive controls. In panel A, compared with the positive controls (dsiRNA and Medusa Control), G A1 B1 has significantly reduced RNAi activity. When activated (G A1 B1+signal), there is a detectable and significant increase in the RNAi activity. Similarly, in panel B, G A1 B4 has significantly less RNAi activity than Medusa control, and the activated form (G A1 B4+signal) has increased RNAi activity.

In panel C, G A1 B6b (SEQ ID NO: 1, SEQ ID NO: 5, SEQ ID NO: 8 and SEQ ID NO: 9), the XRN1 activated design as illustrated in FIGS. 10 and 18, is tested. Compared with Medusa control, the "inactive" G A1 B6b (SEQ ID NO: 1, SEQ ID NO: 5, SEQ ID NO: 8 and SEQ ID NO: 9) has significantly lower RNAi activity. When a signal is activated, the RNAi activity increases for the 5.0 nM and 1.0 nM transfection concentrations.

In the examples illustrated in FIG. 30, the spurious RNAi activity of the "INACTIVE" state constructs are likely caused by spurious opening of the locking sensor in the cellular environment. This can be ameliorated by increasing the thermodynamic stability of the locking sensor via incorporation of modified bases such as LNA.

Example 4

Confirmation of Accessibility and Processing of Medusa Complex Segments in HCT116 Cells To confirm the accessibility of the individual segments of exemplary molecular Applicants transfected some of the constructs tested in Example 3 into HCT116 cells, extracted RNA, and performed a Northern blot with probes specific to the different segments of the complex to observe presence as well as processing.

FIG. 31, some of the constructs shown in FIG. 30 are tested on a Northern blot. In particular, in the illustration of FIG. 31, Probe (oligo 544) (SEQ ID NO: 40) hybridizes to intact guide strand G (29 nucleotides) (SEQ ID NO: 1) seen in lanes 1-9 and the approximately 21 nucleotide Dicer product, indicated by the arrow, visible in lanes 1,2, 7 and 8. Importantly, Dicer products are visible for lane 7 (G Ac B6) (SEQ ID NO: 1, SEQ ID NO: 2, SEQ ID NO: 8 and SEQ ID NO: 9), lane 8 (G Ac Bc6) (G Ac Bc6) (SEQ ID NO: 1, SEQ ID NO: 2, and SEQ ID NO: 19), lane 1 (G Ac B4) (G Ac B4) (SEQ ID NO: 1, SEQ ID NO: 2, SEQ ID NO: 7), and lane 2 (G Ac Bc) (G Ac Bc) (SEQ ID NO: 1, SEQ ID NO: 2, SEQ ID NO: 3), indicating the sensor domains are correctly processed by Dicer. However, lane 5 and lane 6 showed little detectable Dicer product. This indicates that the 3' overhang on sensor A (SEQ ID NO: 5) or on sensor A (SEQ ID NO: 5) bound to the signal RNA is inhibitory for Dicer processing. This is likely caused by the right side of FIG. 19, where the duplex domain in sensor A (SEQ ID NO: 5) overhang or sensor A (SEQ ID NO: 5)::signal RNA stem stacks with the targeting domain, forming a RNA duplex longer than 30 base-pairs. This can induce binding by the PKR protein, a cellular immune sensor, which can interfere with processing by Dicer.

In FIG. 14, Applicants design an implementation, G2 A3 B7 (SEQ ID NO: 10, SEQ ID NO: 11, SEQ ID NO: 12, SEQ ID NO: 13, SEQ ID NO: 14, and SEQ ID 15), to circumvent this effect. Compared with G A1 B6b (SEQ ID NO: 1, SEQ ID NO: 5, SEQ ID NO: 8 and SEQ ID NO: 9) (FIG. 10), G2 A3 B7 (SEQ ID NO: 10, SEQ ID NO: 11, SEQ ID NO: 12, SEQ ID NO: 13, SEQ ID NO: 14, and SEQ ID 15) uses connecting triethylene glycols and hexaethylene glycols and mismatches between the signal binding domain and the signal to create mismatches in the duplex formed by the signal (SEQ ID NO:

16) and the sensor strand, and create an unstructured domains separating the targeting domain and the signal bound sensor domain. This reduced PKR activation. However, the 14 bp sensor stem, with reduced 2'-O-methyl content, is less thermodynamically stable than the 16 bp and 18 bp sensor domains of G A1 B6b (SEQ ID NO: 1, SEQ ID NO: 5, SEQ ID NO: 8 and SEQ ID NO: 9) and G A1 B1, G A1 B4 (SEQ ID NO: 1, SEQ ID NO: 5, SEQ ID NO: 7). Thus, there are two effects, seen in FIG. 32.

The ACTIVE version, G2A3B7S (G A3 B7+signal), has much increased RNAi activity on the dual luciferase assay than GAB6bS (G A1 B6b+signal), due to the PKR avoidance features. However, the INACTIVE conformation, G2A3B7 (G2 A3 B7), also has greater baseline RNAi activity compared with GAB6b* (G A1 B6b). This is due to the decreased stability of the sensor domain. One can also see, however, that G2A3B7S is more active than G2A3B7, indicating that the locking sensor, though unstable, is having some effect.

To obtain better shut-off, the sensor stem for G2A3B7 can be increased to as long as 18 bp, contain uniform 2'-O-methyl bases, or incorporate other stabilizing chemical modifications such as LNA bases.

FIG. 32 is a northern blot on the same set of constructs. Most notably, G2 A3 B7 S (SEQ ID NO: 10, SEQ ID NO: 11, SEQ ID NO: 12, SEQ ID NO: 13, SEQ ID NO: 14, SEQ ID 15, and SEQ ID NO: 16) has a detectable Dicer product. In fact it has more product than the INACTIVE conformation G2 A3 B7 (SEQ ID NO: 10, SEQ ID NO: 11, SEQ ID NO: 12, SEQ ID NO: 13, SEQ ID NO: 14, SEQ ID 15). On the same gel, Dicer products are not detected for GAB6b (SEQ ID NO: 1, SEQ ID NO: 5, SEQ ID NO: 8 and SEQ ID NO: 9) or GAB6bs (SEQ ID NO: 1, SEQ ID NO: 5, SEQ ID NO: 8 and SEQ ID NO: 9 and SEQ ID NO: 16). As the luciferase test shows, both GA1B6b (SEQ ID NO: 1, SEQ ID NO: 5, SEQ ID NO: 8 and SEQ ID NO: 9) and GA1B6bS (SEQ ID NO: 1, SEQ ID NO: 5, SEQ ID NO: 8 and SEQ ID NO: 9 and SEQ ID NO: 16) have some RNAi activity. However, the amount of Dicer product produced may be lower than the detection limit of Northern blog.

Note that in these examples, the spurious Dicer processing and RNAi activity for the INACTIVE constructs is likely the result of the spurious dissociation of the sensor domain. Dicer likely has minimal interaction with the locked siRNA when the targeting domain is actually folded as shown in FIG. 1.

FIG. 33 shows a Northern blot of exemplary Medusa complexes with and without signal strands and controls. Lane M, RNA size markers, number of nucleotides is indicated. Probe (oligo 544) (SEQ ID NO: 40) hybridizes to intact guide strand G (29 nucleotides) (SEQ ID NO:1) seen in all lanes and the approximately 21 nucleotide Dicer product, indicated by the arrow, seen with G Ac Bc6 (SEQ ID NO: 1, SEQ ID NO: 2, and SEQ ID NO: 19), G2 A3 B7 (SEQ ID NO: 10, SEQ ID NO: 11, SEQ ID NO: 12, SEQ ID NO: 13, SEQ ID NO: 14, SEQ ID 15) and G2 A3 B7 S (SEQ ID NO: 10, SEQ ID NO: 11, SEQ ID NO: 12, SEQ ID NO: 13, SEQ ID NO: 14, SEQ ID 15, and SEQ ID NO: 16) (lanes 2, 5 and 6, respectively).

Example 5

Structure Assembly and Processing of an Exemplary Molecular Construct

An exemplary molecular construct was assembled and tested for processing as illustrated below.

FIG. 34 shows an unlocked (G Ac Bc) (SEQ ID NO: 1, SEQ ID NO: 2, SEQ ID NO: 3) and a locked (G RP) (SEQ ID NO: 1, SEQ ID NO: 4) RNAi targeting domain. G Ac Bc (SEQ ID NO: 1, SEQ ID NO: 2, SEQ ID NO: 3) and G RP (SEQ ID NO: 1, SEQ ID NO: 4) have identical sequences, but in G RP (SEQ ID NO: 1, SEQ ID NO: 4) the 3' of Passenger A (SEQ ID NO: 5) is directly linked to the 5' of Passenger B (SEQ ID NO: 6), comprising a single "reversed topology" passenger strand. This linkage locks the RNAi targeting domain into a folded conformation that minimizes proper Dicer processing.

FIG. 35 shows the assembled G RP (SEQ ID NO: 1, SEQ ID NO: 4) product. The individual strands composing GRP (SEQ ID NO: 1, SEQ ID NO: 4) or G Ac Bc (SEQ ID NO: 1) were ordered from a commercial company, Thermo Scientific. For assembly the strands composing G Ac Bc (SEQ ID NO: 1, SEQ ID NO: 2, SEQ ID NO: 3) or G RP (SEQ ID NO: 1, SEQ ID NO: 4) or G RP were combined at 1 micromolar concentration in 1×PBS buffer (approximately 150 mM KCl with other components), heated to ~90 degrees Celsius, and allowed to cool to room temperature. During this process the strands self-assemble into either G Ac Bc (SEQ ID NO: 1, SEQ ID NO: 2, SEQ ID NO: 3) or G RP (SEQ ID NO: 1, SEQ ID NO: 4). The resulting G RP (SEQ ID NO: 1, SEQ ID NO: 4) products were assessed by running through 8% non-denaturing polyacrylamide gel in 1×TBE buffer following standard practices in the art. The first lane on the left shows the band corresponding to the Guide strand alone. In the G RP (SEQ ID NO: 1, SEQ ID NO: 4) lane, there is a clear band showing a construct corresponding to the G RP (SEQ ID NO: 1, SEQ ID NO: 4) construct in the correct conformation. In this conformation, Dicer processing is minimized. In addition, there are a number of higher molecular weight lanes, corresponding to incorrect, multimeric assemblies of G (SEQ ID NO: 1) and RP (SEQ ID NO: 4) strands. These higher molecular weight products can have spurious Dicer processing and RNAi activity. If desired, these products can be removed by filtering using HPLC, or filtration membranes with the appropriate molecular weight cutoff, or by extracting them using native polyacrylamide gel electrophoresis.

FIG. 36 shows dual luciferase assay of G Ac Bc (SEQ ID NO: 1, SEQ ID NO: 2, SEQ ID NO: 3) compared with G RP (SEQ ID NO: 1, SEQ ID NO: 4). The Y axis indicates relative strength of the *Renilla* luciferase:Fire fly luciferase ratio compared with a negative control. 1.0 is the level at which there is no detectable RNAi activity. 0.0 would constitute perfect RNAi knockdown. (Since this is a biology experiment there is some normal variation of experimental values in the range of 10% to 20%). For this experiment, G Ac Bc (SEQ ID NO: 1, SEQ ID NO: 2, SEQ ID NO: 3) transfected into HCT 116 cells at 5 nm, 1 nm, or 0.2 nm concentration reduced *Renilla* luciferase activity to near or below 20% of the nominal value. In contrast, cells transfected with G RP assemblies had much more *Renilla* luciferase activity at every concentration. This shows that there was a significant decrease in the RNAi activity of the G RP (SEQ ID NO: 1, SEQ ID NO: 4) assembly.

Although the RNAi activity of G RP (SEQ ID NO: 1, SEQ ID NO: 4) is reduced, it is still detectable. This is because the G RP (SEQ ID NO: 1, SEQ ID NO: 4) assemblies were transfected without filtration or removal of the higher molecular weight complexes seen in FIG. 35. Thus, while we expect that the correctly assembled G RP (SEQ ID NO: 1, SEQ ID NO: 4) to have minimal Dicer processing and RNAi activity, the presence of higher molecular weight complexes in this assembly is responsible for the detectable amount of RNAi activity seen in this experiment. As stated previously, if desired, the incorrect complexes can be removed from the assemblies using purification methods standard in the art, such as High Performance Liquid Chromatography, native gel electrophoresis and extraction, or molecular separation using filtration membranes with the correct molecular weight cutoff.

FIG. 37 shows the definition of Dicer processing. For a duplex RNAi targeting domain with a guide strand, such as the one shown (G Ac Bc (SEQ ID NO: 1, SEQ ID NO: 2, SEQ ID NO: 3) from FIG. 34), correct processing occurs when PAZ domain of Dicer binds to 3' of the Guide strand (SEQ ID NO: 1) and the endonuclease domain of Dicer cleaves the 5' end of the guide strand (SEQ ID NO: 1) in the position indicated. This will produce a 20 to 26 nucleotide long product, depending on base-pairing. If the targeting domain was perfectly base paired, Dicer processing will produce a 20 to 23 nucleotide long product, highlighted in gray. For an imperfect duplex, the product can be up to 26 nucleotides long.

FIGS. 31 and 33 show Northern blots that include G RP (SEQ ID NO: 1, SEQ ID NO: 4), and a positive control, G Ac Bc6, which is nearly identical in structure with G Ac Bc (SEQ ID NO: 1, SEQ ID NO: 2, SEQ ID NO: 8, SEQ ID NO: 9). A correct Dicer product is clearly seen for G Ac Bc6 (SEQ ID NO: 1, SEQ ID NO: 2, SEQ ID NO: 19) in both Northern blots, while the Dicer product for G RP (SEQ ID NO: 1, SEQ ID NO: 4) in undetectable.

Example 6

Testing and Measuring of the Melting Temperature (Tm) of the Three Way Junction of an Activated RNAaseH Based Construct Exemplary experimental procedures for testing/measuring the melting temperature of the three-way activation formed between the portions of the activation segment in constructs herein described having an RNAaseH based design.

Applicants first synthesized oligonucleotides comprising sequences of designed for the guide strand passenger strand, displacement segment and activation segment respectively using standard methods for oligonucleotide synthesis well establish in the art. Then the synthesized oligonucleotides were then purified based on their expected lengths. The purified oligonucleotides were mixed together in an RNAase free buffer containing PBS. To allow proper annealing of the oligonucleotides, the mixture was heated to about 90° C. for 1 minutes and then cooled to a desired melting temperature of about 15° C. at the rate of 1° C. every 10 seconds. After annealing, RNAse H was added to the buffer and incubated according to manufacturer's instructions to allow cleavage of the construct by RNAse H. The cleavage products were then loaded onto a denaturing polyacrylamide gel (SDS-PAGE) following by electrophoresis to examine whether a proper DNA:RNA duplex of at least 5 consecutive base pairs have formed during annealing and whether the construct was cleaved at the expected RNAse H cleavage site.

To examine whether an activation junction formed among the segments (e.g. a three-way activation junction) is formed properly, Applicants attached pairs of fluorophore/quencher to nucleotides that are expected to form base pairs between opposing strands when the activation junction is properly formed, and examined whether significant quenching of the fluorescence signal can be observed at the minimum melting temperature using fluorescent microcopy. Additionally, the fluorophore/quencher pairs can be attached to pairs of neighboring nucleotides near the junction. Alternatively, in the above experiments, the fluorophore/quencher pairs can be replaced by pairs FRET acceptor/donor fluorophores, and examine significant FRET can be observed at the minimum melting temperature.

As a complimentary approach, Applicants used a standard set of procedures known to the art to establish the secondary structure of the construct.

First, Applicants used single stranded RNA endonucleases to digest the construct, and examined whether RNA portions of the segments that are expected to form double strands were protected from the cleavage by the endonuclease by formation of proper secondary structures.

Second, Applicants used single stranded DNA endonucleases to digest the construct, and examine whether the construct is protected from the cleavage by formation of the secondary structure of the duplex.

Third, Applicants tested whether the expected duplex regions of the junction is protected from RNA modifying and RNA cleaving chemical probes using 5' or 3' radionucleotide labeling or primer extension analysis.

After the above procedures of examining the structure of the activation junction, the construct was exposed to gradual temperature increasing, and the melting temperature of the properly formed activation junction was determined by the inflection points in the UV absorption at 260 nm during the gradual temperature increasing.

The above described experiments can also be performed according to commonly used experimental protocols and procedures, such as the one described in Keril J. Blight et al., Journal Of Virology, October 1997, vol 71, p. 7345-7352 herein incorporated by reference in its entirety.

Example 7

Testing and Measuring of the Melting Temperature (Tm) of the Construct-Locking Sensor Duplex Stem Exemplary experimental procedures for testing/measuring the melting temperature (Tm) of the double-stranded duplex formed by the activation segment and the displacement segment are described below:

Applicants first synthesized oligonucleotides comprising sequences of designed for the guide strand passenger strand, activation segment, displacement segment and toehold segment respectively using standard methods for oligonucleotide synthesis well establish in the art. Then an internal fluorophore was attached to the 3' end of the displacement segment, and a quencher was attached to the 5' end of the protection segment opposing the base carrying the fluorophore. Alternative, the quencher can be attached to the 3' end of the displacement segment, while the internal fluorophore was attached to the 5' end of the protection segment opposing the base carrying the fluorophore. Also, a FRET donor/acceptor fluorophore pairs can be used instead of the fluorophore/quencher pair.

Then the oligonucleotides were purified based on their expected lengths and are mixed together in an RNAse free buffer containing PBS. To allow proper annealing of the oligonucleotides, the mixture was heated to about 90° C. for 1 minutes and then cooled to a desired melting temperature of about 25° C. at the rate of 1° C. every 10 seconds. During the annealing, the fluorescence signal was observed using a spectrofluorometer to examine whether a proper double-stranded duplex is formed between the protection segment and the displacement segment. At the melting temperature of 25° C., the fluorescence signal was quenched (if a FRET pair was used instead of the fluorophore/quencher pair, significant FRET signal between the FRET pairs is expected to be observed), which indicated that a double-stranded duplex has been formed properly between the protection segment and the displacement segment.

In addition, Applicants used the standard panel of enzymatic digest and chemical probe tests to further examine the melting temperature of the construct. Applicants used single strand endonuclease to digest the construct at or below the expected melting temperature (e.g. 25° C.) to examine whether the double-stranded portion of the displacement segment and the protection segment was protected from the endonuclease cleavage.

After the above procedures of examining the structure of the activation junction, the construct was exposed to gradual temperature increasing, and the melting temperature of the properly formed activation junction was determined by the inflection points in the UV absorption at 260 nm during the gradual temperature increasing.

Example 8

Testing and Measuring of the Strand Displacement of the Construct

Exemplary experimental procedures for testing and measuring the strand displacement of the construct are described below:

Applicants first synthesized oligonucleotides comprising sequences of designed for activation segment, displacement segment and toehold segment (locking sensor) using standard methods for oligonucleotide synthesis well establish in the art. Then an internal fluorophore was attached to the terminus of the displacement segment that is further away from the toehold segment. A quencher was attached to the terminus of the activation segment that is further away from the toehold segment. Alternative, the internal fluorophore can be attached to the terminus of the protection segment that is further away from the toehold segment, while a quencher was attached to the terminus of the displacement segment that is further away from the toehold segment. Also, a FRET donor/acceptor fluorophore pairs can be used instead of the fluorophore/quencher pair. Also synthesized was a corresponding signal polynucleotide designed for the sensor domain described above.

Then the synthesized oligonucleotides were purified based on their expected lengths and were incubated with an equal amount of the signal polynucleotide under the operating condition (e.g. 1×PBS buffer) at the expected operating temperature (e.g. 37° C.).

The change in the fluorescent signal during the process of strand displacement was monitored and recorded using a spectrofluorometer. The recorded signal was then plotted as a function of time and the kinetic rate of the displacement reaction was determined from the plot.

To examine whether the attachment of the fluorophore/quencher introduces artifacts to the displacement kinetics and whether the entire protection segment is displaced during the process, the fluorophore/quencher pair was then attached to a different pair of nucleotides selected respectively from the protection segment and the displacement segment at positions closer to the toehold segment, and the above procedures were repeated.

Example 9

Process of Designing, Synthesis and Testing the Activity of a Signal Activated Construct Exemplary processes are described below for the designing, synthesis and testing the activity of a signal activated construct, which comprise a targeting domain configured for interfering a target intracellular process through RNAi.

To design a construct, Applicants started with the analysis of a RNA sequence that was to be targeted (interference) by RNAi, such as a target mRNA or a set of target mRNAs. According to the RNA sequence to be targeted, applicants selected the sequences for the targeting domain of the construct that were known in the art.

For example, in the G2 A3 B7 (SEQ ID NO: 10, SEQ ID NO: 11, SEQ ID NO: 12, SEQ ID NO: 13, SEQ ID NO: 14, and SEQ ID NO: 15) construct shown in FIG. 15, applicants started with the Dicer substrate 27/29 mers duplex with the 29 nucleotide guide strand sequence 5'-C U U G C G U C U G A G G G A U C U C U A G U U A C C U U-3'(SEQ ID NO: 60), where the underlined portion is fully complementary to a conserved HIV-1 target RNA transcript.

Applicants introduce a nick in the passenger 27 nucleotide passenger strand complementary to this guide strand, so that the passenger strand is divided into a 13 nucleotide and a 14 nucleotide piece.

Applicants then selected a conserved portion of the HIV-1 Tat mRNA sequence as a signal polynucleotide. The signal sequence selected was long enough so that there are very few spurious matches to possible RNA transcripts from the organism's genome. In particular, the signal sequence was selected to comprise at least a difference of 4 nucleotides between the signal sequence and its nearest homologous sequence. For using in human cells, the signal polynucleotide can have a minimum length of about 14 nucleotides, but in this case a longer signal was used. Further, the signal polynucleotide was designed to have at least 4 nucleotides that complementarily bind to the toehold segment. In total, the signal nucleotide selected for the use in human cells should be at least 18 nucleotides in length.

In the construct shown in FIG. 13, the applicants chose to have a 16 bp sensor stem and a 5 nucleotide long toehold. Thus, corresponding signal polynucleotide was 21 nucleotides long.

The 5' of this signal polynucleotide was complementary to the 3' sensor toehold illustrated in FIG. 13 and the rest was complementary to the signal binding side of the 16 bp sensor stem.

At this point, the sensor domain was fully specified. The applicants then connected the signal binding strand (left side of the 16 bp sensor stem) to the 3' passenger strand and the displaced segment to the 5' piece of the passenger strand. This allows the sensor domain to lock the targeting domain into the folded, inactive conformation.

In order to ensure sufficient geometric slack to allow formation of the construct, a 2 nucleotide spacer was introduced on the signal binding side and a C3 linker was introduced between the displaced strand and the passenger strand.

The C3 linker also serves to prevent the 5' sensor overhang from interfering with Dicer processing of the ACTIVE RNAi targeting domain.

To further prevent the possible processive exonucleolytic degradation of the 5' passenger strand by XRN1, two 2'-O-methyl base modifications and 2 phosphorothioate backbone modifications were placed immediately to the 3' side of the C3 linker At this stage all segments in the sensor domain (i.e. the protection segment, displacement segment, activation segment and the toehold segment) have been specified. Using the above algorithm, Applicants designed the sensor domains for the every possible 21-nucleotides sequence of the chosen signal polynucleotide (in this case a conserved portion of the HIV-1 Tat-Rev RNA transcript. Then Applicants examined each candidate design by running the sequences through an RNA secondary structure calculation code to examine the predictions for secondary structure conformation and stability. Based on the result, applicants chose one or more candidate designs with the best stability, and the least complicated secondary structure in the toehold, and added chemical modifications to regulate base pair stability.

In particular, for increased stability, Applicants applied added 2'-O-methyl modifications to the entire signal binding side of the sensor duplex. Applicants also changed the 4 bases at the 5' terminus of the guide strand to 2'-O-methyl, and applicants changed some bases in the 3' piece of the passenger strand (the one with 14 base-pairs to the guide strand) to 2'-O-methyl. In addition, an inverted dT base was added to the 3' terminus of the sensor toehold to prevent Dicer binding.

The examples set forth above are provided to give those of ordinary skill in the art a complete disclosure and description of how to make and use the embodiments of the constructs, complexes, sensors, arrangements, devices, compositions, systems and methods of the disclosure, and are not intended to limit the scope of what the inventors regard as their disclosure. All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence. Further, the computer readable form of the sequence listing of the ASCII text file P1210-US-Sequence-Listing_ST25 is incorporated herein by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations which is not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

REFERENCES

Wu, H. et al., "Properties of cloned and expressed human RNase H1", The Journal of Biological Chemistry, Vol. 274, pp. 28270 (1999).

Zamaratski, E. et al., "A critical survey of the structure function of the antisense oligo/RNA heteroduplex as substrate for RNase H", Journal of Biochemical and Biophysical Methods, Vol. 48, pp. 189 (2001).

Cazenave, C. et al., "Characterization and subcellular localization of ribonuclease H activities from Xenopus laevis oocytes", The Journal of biological chemistry, Vol. 269, pp. 25185 (1994).

Nowotny, M. et al., "Crystal structures of RNase H bound to an RNA/DNA hybrid: substrate specificity and metal-dependent catalysis", Cell, Vol. 121, pp. 1005 (2005).

Song, J. J. et al., "The crystal structure of the Argonaute2 PAZ domain reveals an RNA binding motif in RNAi effector complexes", Nature Structural Biology, Vol. 10, pp. 1026 (2003).

Ma, J. B. et al., "Structural basis for overhang-specific small interfering RNA recognition by the PAZ domain", Nature, Vol. 429, pp. 318 (2004).

Yan, K. S. et al., "Structure and conserved RNA binding of the PAZ domain", Nature, Vol. 426, pp. 468 (2003).

Lingel, A. et al., "Structure and nucleic-acid binding of the Drosophila Argonaute 2 PAZ domain", Nature, Vol. 426, pp. 465 (2003).

Behlke, M. A. et al., "Chemical modification of siRNAs for in vivo use", Oligonucleotides, Vol. 18, pp. 305 (2008).

Rose, S. D. et al., "Functional polarity is introduced by Dicer processing of short substrate RNAs", Nucleic Acids Research, Vol. 33, pp. 4140 (2005).

Tomari, Y., et al., "A Protein Sensor for siRNA Asymmetry", Science, Vol. 306, pp. 1377, (2004).

Susan M. Freier and Karl-Heinz Altman, The ups and downs of nucleic acid duplex stability: structure-stability studies on chemically-modified DNA:RNA duplexes, Nucleic Acids Research, 1997, Vol. 25, No. 22 4429-4443

Nucleic Acids Research, 1998, Vol. 26, No. 9, 2224-2229

Nucleic Acids Research, 2005, Vol. 33, No. 16, 5082-5093

564-574 Nucleic Acids Research, 2006, Vol. 34, No. 2

Sequence-specific recognition of double helical RNA and RNA.DNA by triple helix formation, PNAS May 1, 1993 vol. 90 no. 9 3806-3810

Burge S, Parkinson G N, Hazel P, Todd A K, Neidle S (2006). "Quadruplex DNA: sequence, topology and structure". NAR 34 (19): 5402-5415. doi:10.1093/nar/gk1655

J. N. Zadeh, C. D. Steenberg, J. S. Bois, B. R. Wolfe, M. B. Pierce, A. R. Khan, R. M. Dirks, N. A. Pierce. NUPACK: analysis and design of nucleic acid systems. J Comput Chem, 32, 170-173, 2011.

R. M. Dirks, J. S. Bois, J. M. Schaeffer, E. Winfree, and N. A. Pierce. (2007) Thermodynamic analysis of interacting nucleic acid strands. SIAM Rev, 49, 65-88.

R. M. Dirks and N. A. Pierce. (2003) A partition function algorithm for nucleic acid secondary structure including pseudoknots. J Comput Chem, 24, 1664-1677.

R. M. Dirks and N. A. Pierce. (2004) An algorithm for computing nucleic acid base-pairing probabilities including pseudoknots. J Comput Chem, 25, 1295-1304.

J. N. Zadeh, B. R. Wolfe, N. A. Pierce. Nucleic acid sequence design via efficient ensemble defect optimization. J Comput Chem, 32, 439-452, 2011.

M. Zuker. Mfold web server for nucleic acid folding and hybridization prediction. Nucleic Acids Res. 31 (13), 3406-3415, 2003.

Waugh, P. Gendron, R. Altman, J. W. Brown, D. Case, D. Gautheret, S. C. Harvey, N. Leontis, J. Westbrook, E. Westhof, M. Zuker & F. Major. RNAML: A standard syntax for exchanging RNA information. RNA 8 (6), 707-717, 2002.

M. Zuker & A. B. Jacobson. Using Reliability Information to Annotate RNA Secondary Structures. RNA 4, 669-679, 1998. [Abstract][Preprint] Note: Explains color annotation of secondary structure.

N. R. Markham & M. Zuker. UNAFold: Software for Nucleic Acid Folding and Hybridization. In Data, Sequence Analysis, and Evolution, J. Keith, ed., Bioinformatics: Volume 2, Chapter 1, pp 3-31, Humana Press Inc., 2008.

M. Zuker, D. H. Mathews & D. H. Turner. Algorithms and Thermodynamics for RNA Secondary Structure Prediction: A Practical Guide In RNA Biochemistry and Biotechnology, 11-43, J. Barciszewski and B. F. C. Clark, eds., NATO ASI Series, Kluwer Academic Publishers, Dordrecht, NL, 1999.

M. Zuker. Prediction of RNA Secondary Structure by Energy Minimization. In Computer Analysis of Sequence Data A. M. Griffin and H. G. Griffin eds. Methods in Molecular Biology, Humana Press Inc., 267-294, 1994.

J. A. Jaeger, D. H. Turner & M. Zuker. Predicting Optimal and Suboptimal Secondary Structure for RNA. In Molecular Evolution: Computer Analysis of Protein and Nucleic Acid Sequences, R. F. Doolittle ed. Methods in Enzymology 183, 281-306, 1990.

M. Zuker. On Finding All Suboptimal Foldings of an RNA Molecule. Science 244, 48-52, 1989.

D. H. Mathews, J. Sabina, M. Zuker & D. H. Turner. Expanded Sequence Dependence of Thermodynamic Parameters Improves Prediction of RNA Secondary Structure J. Mol. Biol. 288, 911-940, 1999.

E. Walter, D. H. Turner, J. Kim, M. H. Lyttle, P. Müller, D. H. Mathews & M. Zuker. Coaxial stacking of helices enhances binding of oligoribonucleotides and improves predictions of RNA folding. Proc. Natl. Acad. Sci. USA 91, 9218-9222, 1994.

D. H. Mathews, W. N. Moss and D. H. Turner Folding and Finding RNA Secondary Structure in Cold Spring Harb Perspect Biol. 2010.

D. H. Mathews, D. H. Turner & M. Zuker. RNA Secondary Structure Prediction. In Current Protocols in Nucleic Acid Chemistry S. Beaucage, D. E. Bergstrom, G. D. Glick, and R. A. Jones eds., John Wiley & Sons, New York, 11.2.1-11.2. 10, 2007.

D. H. Mathews, S. J. Schroeder, D. H. Turner & M. Zuker. Predicting RNA Secondary Structure. In The RNA World, R. F. Gesteland, T. R. Cech and J. F. Atkins eds., 3rd edition, Cold Spring Harbor Laboratory Press, Cold Spring Harbor, N.Y., Chapter 22, 2006.

D. H. Mathews & M. Zuker. Predictive Methods Using RNA Sequences. In Bioinformatics: A Practical Guide to the Analysis of Genes and Proteins, A. Baxevanis and F. Ouellette eds., 3rd edition, John Wiley & Sons, New York, Chapter 7, 2005.

D. H. Mathews, M. D. Disney, J. L. Childs, S. J. Schroeder, M. Zuker & D. H. Turner. Incorporating chemical modification constraints into a dynamic programming algorithm for prediction of RNA secondary structure. Proc. Natl. Acad. Sci. USA 101 (19), 7287-7292, 2004.

M. Zuker & D. Sankoff. RNA Secondary Structures and their Prediction. Bull. Mathematical Biology 46, 591-621, 1984.

M. Zuker & P. Stiegler. Optimal computer folding of large RNA sequences using thermodynamics and auxiliary information. Nucleic Acids Res. 9, 133-148, 1981.

J.-M. Rouillard, M. Zuker & E. Gulari. OligoArray 2. 0: design of oligonucleotide probes for DNA microarrays using a thermodynamic approach. Nucleic Acids Res. 31 (12), 3057-3062, 2003.

J.-M. Rouillard, C. J. Herbert & M. Zuker. OligoArray: Genome-scale oligonucleotide design for microarrays. Bioinformatics 18 (3), 486-487, 2002.

RNA secondary structure prediction by centroids in a Boltzmann weighted ensemble, Ye Ding, Chi Yu Chan, and Charles E. Lawrence, RNA 2005. 11: 1157-1166

Oligonucleotide synthesis: methods and applications, Volume 288 of Methods in molecular biology, Piet Herdewijn, Humana Press, 2005

Principles of Nucleic Acid Structure, Stephen Neidle, 2008 Elsevier Inc, ISBN: 978-0-12-369507-9

RNA Interference in Mammalian Cells by Chemically-Modified RNA, Biochemistry 2003, 42, 7967-7975

Modified Nucleosides: in Biochemistry, Biotechnology and Medicine, Piet Herdewijn (Editor), Wiley-VCH, 2008 in-Biao Ma, Keqiong Ye & Dinshaw J. Patel Structural basis for overhang specific small interfering RNA recognition by the PAZ domain, Nature, 429, 318 (2004)

Nature Reviews Drug Discovery 8, 129-138 (February 2009) |doi:10.1038/nrd2742, Knocking down barriers: advances in siRNA delivery Simeoni, F. "Insight into the mechanism of the peptide based gene delivery system MPG: implications for delivery of siRNA into mammalian cells." Nucleic acids research 31.11 (2003):2717.

Liu, Z., Winters, M., Holodniy, M. and Dai, H. (2007), siRNA Delivery into Human T Cells and Primary Cells with Carbon-Nanotube Transporters. Angewandte Chemie, 119: 2069-2073. doi: 10.1002/ange.200604295

Aptamer mediated siRNA delivery Nucl. Acids Res. 34(10): e73 doi:10.1093/nar/gk1388

Dynamic PolyConjugates for targeted in vivo delivery of siRNA to hepatocytes PNAS 2007 104 (32) 12982-12987

Bioconjugate Chem., 2007, 18 (5), pp 1391-1396, DOI: 10.1021/bc060367e

T Cell-Specific siRNA Delivery Suppresses HIV-1 Infection in Humanized Mice, Cell, Volume 134, Issue 4, 22 Aug. 2008, Pages 577-586

A universal RNAi-based logic evaluator that operates in mammalian cells, Nature Biotechnology 25, 795-801 (2007)

Molecular Therapy (2010) 18 4, 796-802. doi:10.1038/mt.2009.321, RNA (2010), 16:1275-1284

Molecular Therapy (2006) 13, 494-505

Hong-Wei Wang, Cameron Noland, Bunpote Siridechadilok, David W Taylor, Enbo Ma, Karin Felderer, Jennifer A Doudna & Eva Nogales Structural insights into RNA processing by the human RISC-loading complex Nature Structural & Molecular Biology 16, 1148-1153 (2009)

What is claimed is:

1. A molecular complex for enzyme-assisted molecular delivery, the molecular complex comprising:
 a targeting domain comprising
  a targeting domain duplex RNA having a length of about 19 to about 30 bp, the targeting domain duplex RNA comprising a guide strand complementary bound to a passenger strand,
  wherein
   the passenger strand is nicked in two passenger strand segments each about 2 to about 17 bp long and allowing the targeting domain duplex RNA to adopt a folded conformation and an unfolded conformation,
   in the folded conformation, opposite ends of the targeting domain duplex RNA are in a configuration that minimizes processing of the guide strand by dicer and/or an argonaute enzyme, and
   in the unfolded conformation, the opposite ends of the targeting domain duplex RNA are in a configuration allowing processing of the guide strand by dicer and/or an argonaute enzyme,
 a locking sensor, the locking sensor domain comprising
  an activation segment;
  a displacement segment complementary to the activation segment, the displacement segment complementarily binding the activation segment; and
  a toehold segment complementary to a signal polynucleotide
   wherein the targeting domain is bound to the locking sensor in the folded conformation through covalent attachment of the opposite ends of the targeting domain to a first strand presented on the displacement segment and a second strand presented on the activation segment,
   wherein the displacement segment, and the activation segment are configured so that the molecular complex is configured to release the targeting domain in an unfolded conformation upon binding of a signal molecule to the toehold segment and consequent displacement of the displacement segment from the activation segment.

2. The molecular complex of claim 1, wherein the targeting domain is configured to interfere with a target intracellular process of a cell through RNAi in the presence of the signal molecule.

3. The molecular complex of claim 2, wherein the targeting domain is siRNA, microRNA or an additional duplex structure suitable to be used in connection with RNA interfering.

4. A method to provide the molecular complex for enzyme-assisted molecular delivery of claim 1, the method comprising
 providing a polynucleotide guide strand, a polynucleotide A strand and a polynucleotide B strand,
  wherein
   the polynucleotide A strand comprises from 5' to 3': the toehold segment, the displacement segment and a first passenger strand segment of the two passenger strand segments of the targeting domain in a 5' to 3' configuration; and
   the polynucleotide B strand comprises from 5' to 3' a second passenger strand segment of the two passenger strand segments of the targeting domain and the activation segment; and
 contacting the guide strand, the A strand and the B strand for a time and under condition to allow annealing of the strand to form a molecular complex.

5. A method for enzyme-assisted molecular delivery, the method comprising contacting the molecular complex of claim 1 with the signal molecule for a time and under condition to allow release of the targeting domain from the folded conformation to the unfolded conformation in the molecular complex.

6. A system for enzyme-assisted molecular delivery, the system comprising at least two of one or more molecular complexes of claim 1 and a signal molecule capable to bind to the toehold segment of the one or more molecular complexes of claim 1 for simultaneous, combined or sequential use to control release of the targeting domain from the one or more molecular complexes of claim 1.

7. A composition, comprising one or more of the molecular complex of claim 1 or together with a suitable vehicle.

8. A method for treating a disease in an individual through enzyme-assisted signal activated molecular delivery in cells, the method comprising:
 administering to the individual an effective amount of one or more of the molecular complexes of claim 1.

9. The molecular complex of claim 1, wherein the targeting domain duplex RNA is a small interfering RNA (siRNA), a dicer substrate small interfering RNA (DsiRNA), or a synthetic miRNA analogues (miRNA).

10. The molecular complex of claim 1, wherein the targeting domain has a length of about 19 to about 22 bp or of about 25 to about 30 bp.

11. The molecular complex of claim 1, wherein the targeting domain is locked in the folded conformation by a suitable linkage.

12. The molecular complex of claim 1, wherein the displacement segment complementary binding to the activation segment results in a duplex polynucleotide having a Tm of at least about 25° C. and the complementary binding of the signal polynucleotide to the toehold segment results in a duplex polynucleotide having a Tm of at least about 25° C.

13. The molecular complex of claim 1, wherein the signal molecule is a signal polynucleotide and the binding of the signal polynucleotide to the toehold segment results in a duplex polynucleotide having at least 3 consecutive base pairs.

14. The molecular complex of claim 1, wherein each of the displacement segment, the activation segment and the toehold segment have a 5' terminus and a 3' terminus, and the 3' terminus of the displacement segment is adjacent to the 5' terminus of the toehold segment and the activation segment complementarily binds the displacement segment.

15. The molecular complex of claim 1, wherein in presence of a signal molecule, the unfolded confirmation conformation has a free energy of at least about 5 kcal/mol lower than that the free energy of the folded conformation.

16. The molecular complex of claim 1, wherein in the folded conformation the displacement segment and the activation segment form a double stranded duplex, the duplex being up to 30 bp in length.

17. The molecular complex of claim 16, wherein the duplex comprise at least about 5% 2'-O-methyl modifications or one or two mismatches.

18. The molecular complex of claim 1, wherein the guide strand, passenger strand the activation segment the displacement segment and/or the toehold segment comprise one or more modified ribonucleotides and/or a phosphorothioate segment.

19. The molecular complex of claim 18, wherein the one or more modified ribonucleotides comprise 2'-O-methyl ribonucleotide, 2'-fluoro ribonucleotide, 2'-amino ribonucleotide and/or LNA residues.

20. The molecular complex of claim 18, wherein the one or more modified ribonucleotides are located at a 5' terminus of the passenger strand and the modified ribonucleotides are configured to minimize processing by nucleases.

21. The molecular complex of claim 18, wherein the one or more modified ribonucleotides are located at a 5' terminus of the toehold segment strand and the modified ribonucleotides are configured to minimize processing by nucleases.

22. The molecular complex of claim 1, wherein the activation segment comprises a DNA activation sequence formed by unmodified deoxyribonucleotides.

23. A method to provide the molecular complex for enzyme-assisted molecular delivery of claim 1, the method comprising
contacting a targeting domain with a locking sensor,
the targeting domain comprising
a targeting domain duplex RNA having a length of about 19 to about 30 bp, the targeting domain duplex RNA comprising a guide strand complementary bound to a passenger strand,
wherein
the passenger strand is nicked in two passenger strand segments each about 2 to about 17 bp long and allowing the targeting domain duplex RNA to adopt a folded conformation and an unfolded conformation,
in the folded conformation, opposite ends of the targeting domain duplex RNA are in a configuration that minimizes processing of the guide strand by dicer and/or an argonaute enzyme, and
in the unfolded conformation, the opposite ends of the targeting domain duplex RNA are in a configuration allowing processing of the guide strand by dicer and/or an argonaute enzyme,
the locking sensor comprising
a locking sensor RNA duplex having a toehold segment, a displacement segment and an activation segment,
the displacement segment presenting a first strand; the activation segment presenting a second strand; the displacement segment complementarily binding the activation segment; and the toehold segment being presented for binding to signal molecule;
wherein:
the locking sensor RNA duplex is configured to attach the opposite ends of the targeting domain in a folded conformation, through covalent linkage of the first strand with a first end of the opposite ends of the targeting domain and through covalent linkage of the second strand with a second end of the opposite ends of the targeting domain; and
the displacement segment, activation segment and toehold segment are configured to allow release of the targeting domain from the folded conformation upon binding of a signal molecule to the toehold segment and consequent displacement of the displacement segment from the activation segment,
the contacting performed for a time and under condition to allow covalent attachment of the opposite ends of the targeting domain to the first strand and the second strand of the target binding portion of the locking sensor in a molecular complex comprising the targeting domain in a folded conformation, the molecular complex configured to release the targeting domain in an unfolded conformation upon binding of a signal molecule to the toehold segment and consequent displacement of the displacement segment from the activation segment.

* * * * *

SEQUENCE LISTING

```
<160> NUMBER OF SEQ ID NOS: 60

<210> SEQ ID NO 1
<211> LENGTH: 29
<212> TYPE: RNA
<213> ORGANISM: Artificial sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(3)
<223> OTHER INFORMATION: um
<220> FEATURE:
<221> NAME/KEY: modified_base
<222> LOCATION: (4)..(4)
<223> OTHER INFORMATION: gm

<400> SEQUENCE: 1
cuugcgucug agggaucucu aguuaccuu                                          29

<210> SEQ ID NO 2
<211> LENGTH: 14
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(13)
<223> OTHER INFORMATION: ribonucleotides
<220> FEATURE:
<221> NAME/KEY: misc_feature
<222> LOCATION: (14)..(14)
<223> OTHER INFORMATION: inverted deoxyribonucleotide

<400> SEQUENCE: 2
ccucagacgc aagt                                                          14

<210> SEQ ID NO 3
<211> LENGTH: 14
<212> TYPE: RNA
<213> ORGANISM: Artificial sequence
<220> FEATURE:
<223> OTHER INFORMATION: Synthetic polynucleotide

<400> SEQUENCE: 3
gguaacuaga gauc                                                          14

<210> SEQ ID NO 4
<211> LENGTH: 27
<212> TYPE: RNA
<213> ORGANISM: Artificial sequence
<220> FEATURE:
<223> OTHER INFORMATION: Synthetic polynucleotide
<220> FEATURE:
<221> NAME/KEY: modified_base
<222> LOCATION: (20)..(20)
```

-continued

```
<223> OTHER INFORMATION: um
<220> FEATURE:
<221> NAME/KEY: modified_base
<222> LOCATION: (22)..(22)
<223> OTHER INFORMATION: gm
<220> FEATURE:
<221> NAME/KEY: modified_base
<222> LOCATION: (24)..(24)
<223> OTHER INFORMATION: gm
<220> FEATURE:
<221> NAME/KEY: modified_base
<222> LOCATION: (27)..(27)
<223> OTHER INFORMATION: cm

<400> SEQUENCE: 4
ccucagacgc aaggguaacu agagauc                                            27

<210> SEQ ID NO 5
<211> LENGTH: 37
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(36)
<223> OTHER INFORMATION: ribonucleotides
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: gm
<220> FEATURE:
<221> NAME/KEY: misc_feature
<222> LOCATION: (17)..(17)
<223> OTHER INFORMATION: 2'-O-methyl adenosine
<220> FEATURE:
<221> NAME/KEY: modified_base
<222> LOCATION: (18)..(18)
<223> OTHER INFORMATION: um
<220> FEATURE:
<221> NAME/KEY: modified_base
<222> LOCATION: (19)..(19)
<223> OTHER INFORMATION: gm
<220> FEATURE:
<221> NAME/KEY: misc_feature
<222> LOCATION: (20)..(20)
<223> OTHER INFORMATION: 2'-O-methyl adenosine
<220> FEATURE:
<221> NAME/KEY: modified_base
<222> LOCATION: (21)..(21)
<223> OTHER INFORMATION: gm
<220> FEATURE:
<221> NAME/KEY: modified_base
<222> LOCATION: (22)..(22)
<223> OTHER INFORMATION: cm
<220> FEATURE:
<221> NAME/KEY: modified_base
<222> LOCATION: (23)..(23)
<223> OTHER INFORMATION: um
<220> FEATURE:
<221> NAME/KEY: modified_base
<222> LOCATION: (24)..(24)
<223> OTHER INFORMATION: cm
<220> FEATURE:
<221> NAME/KEY: modified_base
<222> LOCATION: (25)..(26)
<223> OTHER INFORMATION: um
<220> FEATURE:
<221> NAME/KEY: modified_base
```

```
<222> LOCATION: (27)..(27)
<223> OTHER INFORMATION: cm
<220> FEATURE:
<221> NAME/KEY: modified_base
<222> LOCATION: (28)..(28)
<223> OTHER INFORMATION: gm
<220> FEATURE:
<221> NAME/KEY: modified_base
<222> LOCATION: (29)..(29)
<223> OTHER INFORMATION: um
<220> FEATURE:
<221> NAME/KEY: modified_base
<222> LOCATION: (30)..(30)
<223> OTHER INFORMATION: cm
<220> FEATURE:
<221> NAME/KEY: modified_base
<222> LOCATION: (31)..(31)
<223> OTHER INFORMATION: gm
<220> FEATURE:
<221> NAME/KEY: modified_base
<222> LOCATION: (32)..(32)
<223> OTHER INFORMATION: cm
<220> FEATURE:
<221> NAME/KEY: modified_base
<222> LOCATION: (33)..(33)
<223> OTHER INFORMATION: um
<220> FEATURE:
<221> NAME/KEY: modified_base
<222> LOCATION: (34)..(34)
<223> OTHER INFORMATION: gm
<220> FEATURE:
<221> NAME/KEY: modified_base
<222> LOCATION: (35)..(36)
<223> OTHER INFORMATION: um
<220> FEATURE:
<221> NAME/KEY: misc_feature
<222> LOCATION: (37)..(37)
<223> OTHER INFORMATION: inverted deoxyribonucleotide

<400> SEQUENCE: 5
ccucagacgc aagcugauga gcucuucguc gcuguut                    37

<210> SEQ ID NO 6
<211> LENGTH: 44
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: 2'-O-methyl adenosine
<220> FEATURE:
<221> NAME/KEY: misc_feature
<222> LOCATION: (1)..(5)
<223> OTHER INFORMATION: ribonucleotides
<220> FEATURE:
<221> NAME/KEY: modified_base
<222> LOCATION: (3)..(4)
<223> OTHER INFORMATION: gm
<220> FEATURE:
<221> NAME/KEY: modified_base
<222> LOCATION: (5)..(5)
<223> OTHER INFORMATION: um
<220> FEATURE:
<221> NAME/KEY: misc_feature
<222> LOCATION: (6)..(12)
<223> OTHER INFORMATION: deoxyribonucleotides
<220> FEATURE:
<221> NAME/KEY: misc_feature
<222> LOCATION: (7)..(44)
<223> OTHER INFORMATION: ribonucleotides

<400> SEQUENCE: 6
aagguccctg atcgacgaag agcucaucag gguaacuaga gauc            44
```

```
<210> SEQ ID NO 7
<211> LENGTH: 44
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: 2'-O-methyl adenosine
<220> FEATURE:
<221> NAME/KEY: misc_feature
<222> LOCATION: (1)..(5)
<223> OTHER INFORMATION: ribonucleotides
<220> FEATURE:
<221> NAME/KEY: modified_base
<222> LOCATION: (3)..(4)
<223> OTHER INFORMATION: gm
<220> FEATURE:
<221> NAME/KEY: modified_base
<222> LOCATION: (5)..(5)
<223> OTHER INFORMATION: um
<220> FEATURE:
<221> NAME/KEY: misc_feature
<222> LOCATION: (6)..(12)
<223> OTHER INFORMATION: deoxyribonucleotides
<220> FEATURE:
<221> NAME/KEY: misc_feature
<222> LOCATION: (13)..(44)
<223> OTHER INFORMATION: ribonucleotides
<220> FEATURE:
<221> NAME/KEY: modified_base
<222> LOCATION: (37)..(37)
<223> OTHER INFORMATION: um
<220> FEATURE:
<221> NAME/KEY: modified_base
<222> LOCATION: (39)..(39)
<223> OTHER INFORMATION: gm
<220> FEATURE:
<221> NAME/KEY: modified_base
<222> LOCATION: (41)..(41)
<223> OTHER INFORMATION: gm
<220> FEATURE:
<221> NAME/KEY: modified_base
<222> LOCATION: (44)..(44)
<223> OTHER INFORMATION: cm

<400> SEQUENCE: 7
aagguccctg atcgacgaag agcucaucag gguaacuaga gauc                    44

<210> SEQ ID NO 8
<211> LENGTH: 16
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (16)..(16)
<223> OTHER INFORMATION: C3 linker to 5' end of SEQ ID NO: 9

<400> SEQUENCE: 8
cgacgaagag cucauc                                                   16

<210> SEQ ID NO 9
<211> LENGTH: 14
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: C3 linker to 3' end of SEQ ID NO: 8
```

```
<220> FEATURE:
<221> NAME/KEY: misc_feature
<222> LOCATION: (1)..(2)
<223> OTHER INFORMATION: phosphorothioate backbone
<220> FEATURE:
<221> NAME/KEY: modified_base
<222> LOCATION: (1)..(2)
<223> OTHER INFORMATION: gm
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (14)..(14)
<223> OTHER INFORMATION: cm

<400> SEQUENCE: 9
gguaacuaga gauc                                                      14

<210> SEQ ID NO 10
<211> LENGTH: 27
<212> TYPE: RNA
<213> ORGANISM: Artificial sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(2)
<223> OTHER INFORMATION: gm

<400> SEQUENCE: 10
cgcgucugag ggaucucuag uuaccuu                                        27

<210> SEQ ID NO 11
<211> LENGTH: 12
<212> TYPE: RNA
<213> ORGANISM: Artificial sequence
<220> FEATURE:
<223> OTHER INFORMATION: Synthetic polynucleotide
<220> FEATURE:
<221> NAME/KEY: modified_base
<222> LOCATION: (11)..(11)
<223> OTHER INFORMATION: cm
<220> FEATURE:
<221> NAME/KEY: misc_feature
<222> LOCATION: (11)..(12)
<223> OTHER INFORMATION: phosphorothioate backbone
<220> FEATURE:
<221> NAME/KEY: misc_feature
<222> LOCATION: (12)..(12)
<223> OTHER INFORMATION: 18S linker to 5' end of SEQ ID NO: 12
<220> FEATURE:
<221> NAME/KEY: modified_base
<222> LOCATION: (12)..(12)
```

<223> OTHER INFORMATION: gm

<400> SEQUENCE: 11
cccucagacg cg                                                          12

<210> SEQ ID NO 12
<211> LENGTH: 16
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 18S linker to 3' end of SEQ ID NO: 11
<220> FEATURE:
<221> NAME/KEY: modified_base
<222> LOCATION: (3)..(3)
<223> OTHER INFORMATION: um
<220> FEATURE:
<221> NAME/KEY: misc_feature
<222> LOCATION: (5)..(5)
<223> OTHER INFORMATION: 2'-O-methyl adenosine
<220> FEATURE:
<221> NAME/KEY: misc_feature
<222> LOCATION: (7)..(8)
<223> OTHER INFORMATION: n = any nucleotide
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: um
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: misc_feature
<222> LOCATION: (15)..(15)
<223> OTHER INFORMATION: 9S linker to the 5' end of SEQ ID NO: 13

<400> SEQUENCE: 12
gaugagnncu ucgucg                                                      16

<210> SEQ ID NO 13
<211> LENGTH: 8
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 9S linker to the 3'end of SEQ ID NO: 12
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (5)..(6)
<223> OTHER INFORMATION: cm
<220> FEATURE:
<221> NAME/KEY: misc_feature
<222> LOCATION: (8)..(8)
<223> OTHER INFORMATION: 9S linker attached to an inverted deoxyribose T
<220> FEATURE:
<221> NAME/KEY: modified_base

```
<222> LOCATION: (8)..(8)
<223> OTHER INFORMATION: cm

<400> SEQUENCE: 13 gucuccgc                                                                8

<210> SEQ ID NO 14
<211> LENGTH: 15
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: C3 linker to the 3'end of SEQ ID NO: 13
<220> FEATURE:
<221> NAME/KEY: misc_feature
<222> LOCATION: (15)..(15)
<223> OTHER INFORMATION: C3 linker to the 3'end of SEQ ID NO: 15

<400> SEQUENCE: 14
cgacgaagcu cauca                                                       15

<210> SEQ ID NO 15
<211> LENGTH: 13
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: C3 linker to the 3' end of SEQ ID NO: 14
<220> FEATURE:
<221> NAME/KEY: misc_feature
<222> LOCATION: (1)..(2)
<223> OTHER INFORMATION: phosphorothiate backbone
<220> FEATURE:
<221> NAME/KEY: modified_base
<222> LOCATION: (1)..(2)
<223> OTHER INFORMATION: gm
<220> FEATURE:
<221> NAME/KEY: modified_base
<222> LOCATION: (3)..(3)
<223> OTHER INFORMATION: um
<220> FEATURE:
<221> NAME/KEY: misc_feature
<222> LOCATION: (8)..(8)
<223> OTHER INFORMATION: 2'-O-methyl adenosine
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (13)..(13)
<223> OTHER INFORMATION: um

<400> SEQUENCE: 15
gguaacuaga gau                                                         13

<210> SEQ ID NO 16
<211> LENGTH: 39
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(5)
<223> OTHER INFORMATION: 2'-O-methyl adenosine
<220> FEATURE:
```

```
<221> NAME/KEY: misc_feature
<222> LOCATION: (1)..(38)
<223> OTHER INFORMATION: ribonucleotides
<220> FEATURE:
<221> NAME/KEY: misc_feature
<222> LOCATION: (34)..(38)
<223> OTHER INFORMATION: 2'-O-methyl adenosine
<220> FEATURE:
<221> NAME/KEY: misc_feature
<222> LOCATION: (39)..(39)
<223> OTHER INFORMATION: inverted dexoyribonucleotide

<400> SEQUENCE: 16
aaaaagcgga gacagcgacg aagagcucau cagaaaaat                         39

<210> SEQ ID NO 17
<211> LENGTH: 18
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (18)..(18)
<223> OTHER INFORMATION: C3 linker to the 5' end of SEQ ID NO: 18

<400> SEQUENCE: 17
cgacgaagag cucaucag                                                18

<210> SEQ ID NO 18
<211> LENGTH: 14
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: C3 linker to the 3' end of SEQ ID NO: 17
<220> FEATURE:
<221> NAME/KEY: misc_feature
<222> LOCATION: (1)..(2)
<223> OTHER INFORMATION: phosphorothioate backbone
<220> FEATURE:
<221> NAME/KEY: modified_base
<222> LOCATION: (1)..(2)
<223> OTHER INFORMATION: gm
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (14)..(14)
<223> OTHER INFORMATION: cm

<400> SEQUENCE: 18
gguaacuaga gauc                                                    14

<210> SEQ ID NO 19
<211> LENGTH: 14
```

```
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: C3 linker
<220> FEATURE:
<221> NAME/KEY: misc_feature
<222> LOCATION: (1)..(2)
<223> OTHER INFORMATION: phosphorothioate backbone
<220> FEATURE:
<221> NAME/KEY: modified_base
<222> LOCATION: (1)..(2)
<223> OTHER INFORMATION: gm
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (14)..(14)
<223> OTHER INFORMATION: cm

<400> SEQUENCE: 19
gguaacuaga gauc                                                         14

<210> SEQ ID NO 20
<211> LENGTH: 21
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (21)..(21)
<223> OTHER INFORMATION: C3 linker to the 5'end of SEQ ID NO: 21

<400> SEQUENCE: 20
gacagcgacg aaggcgacgg c                                                 21

<210> SEQ ID NO 21
<211> LENGTH: 14
<212> TYPE: RNA
<213> ORGANISM: Artificial sequence
<220> FEATURE:
<223> OTHER INFORMATION: Synthetic polynucleotide
<220> FEATURE:
<221> NAME/KEY: modified_base
<222> LOCATION: (1)..(2)
<223> OTHER INFORMATION: gm
<220> FEATURE:
<221> NAME/KEY: misc_feature
<222> LOCATION: (1)..(1)
<223> OTHER INFORMATION: C3 linker to the 3' end of SEQ ID NO: 20
<220> FEATURE:
<221> NAME/KEY: misc_feature
<222> LOCATION: (1)..(3)
<223> OTHER INFORMATION: phosphorothioate backbone
<220> FEATURE:
<221> NAME/KEY: misc_feature
<222> LOCATION: (14)..(14)
```

<223> OTHER INFORMATION: 18S linker to the 5' end of SEQ ID NO: 22

<400> SEQUENCE: 21
gguaacuaga gauc                                                           14

<210> SEQ ID NO 22
<211> LENGTH: 13
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 18S linker to the 3' end of SEQ ID NO: 21
<220> FEATURE:
<221> NAME/KEY: misc_feature
<222> LOCATION: (11)..(13)
<223> OTHER INFORMATION: phosphorothioate backbone
<220> FEATURE:
<221> NAME/KEY: misc_feature
<222> LOCATION: (12)..(12)
<223> OTHER INFORMATION: 2'-O-methyl adenosine
<220> FEATURE:
<221> NAME/KEY: modified_base
<222> LOCATION: (13)..(13)
<223> OTHER INFORMATION: gm
<220> FEATURE:
<221> NAME/KEY: misc_feature
<222> LOCATION: (13)..(13)
<223> OTHER INFORMATION: 18S linker to the 5' end of SEQ ID NO: 23

<400> SEQUENCE: 22
ccucagacgc aag                                                            13

<210> SEQ ID NO 23
<211> LENGTH: 19
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 18S linker to the 3'end of SEQ ID NO: 22
<220> FEATURE:
<221> NAME/KEY: misc_feature
<222> LOCATION: (19)..(19)
<223> OTHER INFORMATION: inverted deoxyribonucleotide

<400> SEQUENCE: 23
gccgucgcag cucaucagt                                                      19

<210> SEQ ID NO 24
<211> LENGTH: 13
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (11)..(13)
<223> OTHER INFORMATION: phosphorothioate backbone
<220> FEATURE:
<221> NAME/KEY: misc_feature
<222> LOCATION: (12)..(12)
<223> OTHER INFORMATION: 2'-O-methyl adenosine
<220> FEATURE:
<221> NAME/KEY: misc_feature
<222> LOCATION: (13)..(13)
<223> OTHER INFORMATION: 18S linker to 5' end of SEQ ID NO: 25
<220> FEATURE:
<221> NAME/KEY: modified_base -continued

```
<222> LOCATION: (13)..(13)
<223> OTHER INFORMATION: gm

<400> SEQUENCE: 24
ccucagacgc aag                                                        13

<210> SEQ ID NO 25
<211> LENGTH: 23
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 18S linker to 3'end of SEQ ID NO: 24

<400> SEQUENCE: 25
gaugagcucu ucgucgcugu cuc                                             23

<210> SEQ ID NO 26
<211> LENGTH: 7
<212> TYPE: RNA
<213> ORGANISM: Artificial sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: cm
<220> FEATURE:
<221> NAME/KEY: misc_feature
<222> LOCATION: (1)..(1)
<223> OTHER INFORMATION: 9S linker
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: 9S linker to the 5'end of SEQ ID NO: 27

<400> SEQUENCE: 26 cugauga                                                                7

<210> SEQ ID NO 27
<211> LENGTH: 9
<212> TYPE: RNA
<213> ORGANISM: Artificial sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: gm
<220> FEATURE:
<221> NAME/KEY: misc_feature
<222> LOCATION: (1)..(1)
<223> OTHER INFORMATION: 9S linker to the 3' end of SEQ ID NO: 26
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (4)..(4)
<223> OTHER INFORMATION: cm
<220> FEATURE:
```

```
<221> NAME/KEY: modified_base
<222> LOCATION: (6)..(6)
<223> OTHER INFORMATION: um
<220> FEATURE:
<221> NAME/KEY: modified_base
<222> LOCATION: (8)..(8)
<223> OTHER INFORMATION: gm
<220> FEATURE:
<221> NAME/KEY: misc_feature
<222> LOCATION: (9)..(9)
<223> OTHER INFORMATION: 18S linker to the 5' end of SEQ ID NO: 28

<400> SEQUENCE: 27 gcucuucgu                                                                  9

<210> SEQ ID NO 28
<211> LENGTH: 10
<212> TYPE: RNA
<213> ORGANISM: Artificial sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: cm
<220> FEATURE:
<221> NAME/KEY: misc_feature
<222> LOCATION: (1)..(1)
<223> OTHER INFORMATION: 18S linker to the 3'end of SEQ ID NO: 27
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (9)..(10)
<223> OTHER INFORMATION: cm
<220> FEATURE:
<221> NAME/KEY: misc_feature
<222> LOCATION: (10)..(10)
<223> OTHER INFORMATION: 18S linker attached to inverted deoxynucleotide
      T

<400> SEQUENCE: 28
cgcugucucc                                                                10

<210> SEQ ID NO 29
<211> LENGTH: 53
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (29)..(29)
<223> OTHER INFORMATION: n = any nucleotide
<220> FEATURE:
<221> NAME/KEY: misc_feature
<222> LOCATION: (36)..(36)
<223> OTHER INFORMATION: n = any nucleotide
<220> FEATURE:
<221> NAME/KEY: misc_feature
<222> LOCATION: (45)..(45)
<223> OTHER INFORMATION: n = any nucleotide

<400> SEQUENCE: 29
```
cugaugagcu cuucgucgcu gucuccgcng augagncuuc gucgngucuc cgc        53

<210> SEQ ID NO 30
<211> LENGTH: 15
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(15)
<223> OTHER INFORMATION: locked nucleic acid (LNA)
<220> FEATURE:
<221> NAME/KEY: misc_feature
<222> LOCATION: (4)..(4)
<223> OTHER INFORMATION: n = any nucleotide
<220> FEATURE:
<221> NAME/KEY: misc_feature
<222> LOCATION: (7)..(7)
<223> OTHER INFORMATION: n = any nucleotide

<400> SEQUENCE: 30
cttngcngtc tgagg        15

<210> SEQ ID NO 31
<211> LENGTH: 13
<212> TYPE: RNA
<213> ORGANISM: Artificial sequence
<220> FEATURE:
<223> OTHER INFORMATION: Synthetic polynucleotide

<400> SEQUENCE: 31
ccucagacgc aag        13

<210> SEQ ID NO 32
<211> LENGTH: 17
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(17)
<223> OTHER INFORMATION: locked nucleic acid (LNA)
<220> FEATURE:
<221> NAME/KEY: misc_feature
<222> LOCATION: (2)..(2)
<223> OTHER INFORMATION: n = any nucleotide
<220> FEATURE:
<221> NAME/KEY: misc_feature
<222> LOCATION: (6)..(6)
<223> OTHER INFORMATION: n = any nucleotide
<220> FEATURE:
<221> NAME/KEY: misc_feature
<222> LOCATION: (13)..(13)
<223> OTHER INFORMATION: n = any nucleotide

<400> SEQUENCE: 32
gantcntcta gtntacc        17

<210> SEQ ID NO 33
<211> LENGTH: 14
<212> TYPE: RNA
<213> ORGANISM: Artificial sequence
<220> FEATURE:
<223> OTHER INFORMATION: Synthetic polynucleotide

<400> SEQUENCE: 33
gguaacuaga gauc        14

```
<210> SEQ ID NO 34
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 34
cagactttgt tggatttgaa a                                              21

<210> SEQ ID NO 35
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 35
uuucaaaucc aacaaagucu g                                              21

<210> SEQ ID NO 36
<211> LENGTH: 26
<212> TYPE: DNA
<213> ORGANISM: Artificial sequence
<220> FEATURE:
<223> OTHER INFORMATION: Synthetic polynucleotide

<400> SEQUENCE: 36
cttcaagcca gactttgttg gatttg                                         26

<210> SEQ ID NO 37
<211> LENGTH: 25
<212> TYPE: RNA
<213> ORGANISM: Artificial sequence
<220> FEATURE:
<223> OTHER INFORMATION: Synthetic polynucleotide

<400> SEQUENCE: 37
caaauccaac aaaucuggcu ugaag                                          25

<210> SEQ ID NO 38
<211> LENGTH: 22
<212> TYPE: DNA
<213> ORGANISM: Artificial sequence
<220> FEATURE:
<223> OTHER INFORMATION: Synthetic polynucleotide

<400> SEQUENCE: 38
acagcgacga agagctcatc ag                                             22

<210> SEQ ID NO 39
<211> LENGTH: 22
<212> TYPE: RNA
<213> ORGANISM: Artificial sequence
<220> FEATURE:
<223> OTHER INFORMATION: Synthetic polynucleotide

<400> SEQUENCE: 39
cugaugugcu cuucgucgcu gu                                             22

<210> SEQ ID NO 40
<211> LENGTH: 21
<212> TYPE: DNA
<213> ORGANISM: Artificial sequence
<220> FEATURE:
<223> OTHER INFORMATION: Synthetic polynucleotide
```

```
<400> SEQUENCE: 40
ggtaactaga gatccctcag a                                              21

<210> SEQ ID NO 41
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(3)
<223> OTHER INFORMATION: deoxyribonucleotides
<220> FEATURE:
<221> NAME/KEY: misc_feature
<222> LOCATION: (4)..(21)
<223> OTHER INFORMATION: ribonucleotides

<400> SEQUENCE: 41
tctgagggau cucuaguuac c                                              21

<210> SEQ ID NO 42
<211> LENGTH: 22
<212> TYPE: DNA
<213> ORGANISM: Artificial sequence
<220> FEATURE:
<223> OTHER INFORMATION: Synthetic polynucleotide

<400> SEQUENCE: 42
acagcgacga agagctcatc ag                                             22

<210> SEQ ID NO 43
<211> LENGTH: 22
<212> TYPE: RNA
<213> ORGANISM: Artificial sequence
<220> FEATURE:
<223> OTHER INFORMATION: Synthetic polynucleotide

<400> SEQUENCE: 43
cugaugagcu cuucgucgcu gu                                             22

<210> SEQ ID NO 44
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 44
ccctgatgag ctcttcgtcg                                                20

<210> SEQ ID NO 45
<211> LENGTH: 20
<212> TYPE: RNA
<213> ORGANISM: Artificial sequence
<220> FEATURE:
<223> OTHER INFORMATION: Synthetic polynucleotide

<400> SEQUENCE: 45
cgacgaagag cucaucaggg                                                20

<210> SEQ ID NO 46
<211> LENGTH: 20
<212> TYPE: DNA
<213> ORGANISM: Artificial sequence
<220> FEATURE:
<223> OTHER INFORMATION: Synthetic polynucleotide
```

```
<400> SEQUENCE: 46
cttcgtcgat cagggtcctt                                               20

<210> SEQ ID NO 47
<211> LENGTH: 20
<212> TYPE: RNA
<213> ORGANISM: Artificial sequence
<220> FEATURE:
<223> OTHER INFORMATION: Synthetic polynucleotide

<400> SEQUENCE: 47
aaggacccug aucgacgaag                                               20

<210> SEQ ID NO 48
<211> LENGTH: 13
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (11)..(13)
<223> OTHER INFORMATION: phosphorothioate backbone
<220> FEATURE:
<221> NAME/KEY: misc_feature
<222> LOCATION: (12)..(12)
<223> OTHER INFORMATION: 2'-O-methyl adenosine
<220> FEATURE:
<221> NAME/KEY: misc_feature
<222> LOCATION: (13)..(13)
<223> OTHER INFORMATION: ethylene glycol linker to the 5' end of SEQ ID
      NO: 49
<220> FEATURE:
<221> NAME/KEY: modified_base
<222> LOCATION: (13)..(13)
<223> OTHER INFORMATION: gm

<400> SEQUENCE: 48
ccucagacgc aag                                                      13

<210> SEQ ID NO 49
<211> LENGTH: 23
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: ethylene glycol linker to the 3'end of SEQ ID
      NO: 48

<400> SEQUENCE: 49
gaugagcucu ucgucgcugu cuc                                           23

<210> SEQ ID NO 50
<211> LENGTH: 38
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(5)
<223> OTHER INFORMATION: 2'-O-methyl adenosine
<220> FEATURE:
<221> NAME/KEY: misc_feature
<222> LOCATION: (34)..(37)
<223> OTHER INFORMATION: 2'-O-methyl adenosine
<220> FEATURE:
<221> NAME/KEY: misc_feature
```

```
<222> LOCATION: (38)..(38)
<223> OTHER INFORMATION: inverted dexoyribonucleotide

<400> SEQUENCE: 50
aaaaagcgga gacagcgacg aagagcucau cgaaaaat                           38

<210> SEQ ID NO 51
<211> LENGTH: 81
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: 2'-O-methyl adenosine
<220> FEATURE:
<221> NAME/KEY: misc_feature
<222> LOCATION: (1)..(5)
<223> OTHER INFORMATION: ribonucleotides
<220> FEATURE:
<221> NAME/KEY: modified_base
<222> LOCATION: (3)..(4)
<223> OTHER INFORMATION: gm
<220> FEATURE:
<221> NAME/KEY: modified_base
<222> LOCATION: (5)..(5)
<223> OTHER INFORMATION: um
<220> FEATURE:
<221> NAME/KEY: misc_feature
<222> LOCATION: (6)..(12)
<223> OTHER INFORMATION: deoxyribonucleotides
<220> FEATURE:
<221> NAME/KEY: misc_feature
<222> LOCATION: (13)..(80)
<223> OTHER INFORMATION: ribonucleotides
<220> FEATURE:
<221> NAME/KEY: modified_base
<222> LOCATION: (37)..(37)
<223> OTHER INFORMATION: um
<220> FEATURE:
<221> NAME/KEY: modified_base
<222> LOCATION: (39)..(39)
<223> OTHER INFORMATION: gm
<220> FEATURE:
<221> NAME/KEY: modified_base
<222> LOCATION: (41)..(41)
<223> OTHER INFORMATION: gm
<220> FEATURE:
<221> NAME/KEY: modified_base
<222> LOCATION: (44)..(44)
<223> OTHER INFORMATION: cm
<220> FEATURE:
<221> NAME/KEY: modified_base
<222> LOCATION: (58)..(58)
<223> OTHER INFORMATION: cm
<220> FEATURE:
<221> NAME/KEY: modified_base
<222> LOCATION: (59)..(59)
<223> OTHER INFORMATION: um
<220> FEATURE:
<221> NAME/KEY: modified_base
<222> LOCATION: (60)..(60)
<223> OTHER INFORMATION: gm
<220> FEATURE:
<221> NAME/KEY: misc_feature
<222> LOCATION: (61)..(61)
<223> OTHER INFORMATION: 2'-O-methyl adenosine
<220> FEATURE:
<221> NAME/KEY: modified_base
<222> LOCATION: (62)..(62)
<223> OTHER INFORMATION: um
<220> FEATURE:
<221> NAME/KEY: modified_base
<222> LOCATION: (63)..(63)
<223> OTHER INFORMATION: gm
<220> FEATURE:
```

```
<221> NAME/KEY: misc_feature
<222> LOCATION: (64)..(64)
<223> OTHER INFORMATION: 2'-O-methyl adenosine
<220> FEATURE:
<221> NAME/KEY: modified_base
<222> LOCATION: (65)..(65)
<223> OTHER INFORMATION: gm
<220> FEATURE:
<221> NAME/KEY: modified_base
<222> LOCATION: (66)..(66)
<223> OTHER INFORMATION: cm
<220> FEATURE:
<221> NAME/KEY: modified_base
<222> LOCATION: (67)..(67)
<223> OTHER INFORMATION: um
<220> FEATURE:
<221> NAME/KEY: modified_base
<222> LOCATION: (68)..(68)
<223> OTHER INFORMATION: cm
<220> FEATURE:
<221> NAME/KEY: modified_base
<222> LOCATION: (69)..(70)
<223> OTHER INFORMATION: um
<220> FEATURE:
<221> NAME/KEY: modified_base
<222> LOCATION: (71)..(71)
<223> OTHER INFORMATION: cm
<220> FEATURE:
<221> NAME/KEY: modified_base
<222> LOCATION: (72)..(72)
<223> OTHER INFORMATION: gm
<220> FEATURE:
<221> NAME/KEY: modified_base
<222> LOCATION: (73)..(73)
<223> OTHER INFORMATION: um
<220> FEATURE:
<221> NAME/KEY: modified_base
<222> LOCATION: (74)..(74)
<223> OTHER INFORMATION: cm
<220> FEATURE:
<221> NAME/KEY: modified_base
<222> LOCATION: (75)..(75)
<223> OTHER INFORMATION: gm
<220> FEATURE:
<221> NAME/KEY: modified_base
<222> LOCATION: (76)..(76)
<223> OTHER INFORMATION: cm
<220> FEATURE:
<221> NAME/KEY: modified_base
<222> LOCATION: (77)..(77)
<223> OTHER INFORMATION: um
<220> FEATURE:
<221> NAME/KEY: modified_base
<222> LOCATION: (78)..(78)
<223> OTHER INFORMATION: gm
<220> FEATURE:
<221> NAME/KEY: modified_base
<222> LOCATION: (79)..(80)
<223> OTHER INFORMATION: um
<220> FEATURE:
<221> NAME/KEY: misc_feature
<222> LOCATION: (81)..(81)
<223> OTHER INFORMATION: inverted deoxyribonucleotide

<400> SEQUENCE: 51
aagguccctg atcgacgaag agcucaucag gguaacuaga gaucccucag acgcaagcug    60
augagcucuu cgucgcuguu t                                              81

<210> SEQ ID NO 52
<211> LENGTH: 81
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
```

```
<222> LOCATION: (1)..(2)
<223> OTHER INFORMATION: 2'-O-methyl adenosine
<220> FEATURE:
<221> NAME/KEY: misc_feature
<222> LOCATION: (1)..(5)
<223> OTHER INFORMATION: ribonucleotides
<220> FEATURE:
<221> NAME/KEY: modified_base
<222> LOCATION: (3)..(4)
<223> OTHER INFORMATION: gm
<220> FEATURE:
<221> NAME/KEY: modified_base
<222> LOCATION: (5)..(5)
<223> OTHER INFORMATION: um
<220> FEATURE:
<221> NAME/KEY: misc_feature
<222> LOCATION: (6)..(12)
<223> OTHER INFORMATION: deoxyribonucleotides
<220> FEATURE:
<221> NAME/KEY: misc_feature
<222> LOCATION: (13)..(80)
<223> OTHER INFORMATION: ribonucleotides
<220> FEATURE:
<221> NAME/KEY: modified_base
<222> LOCATION: (58)..(58)
<223> OTHER INFORMATION: cm
<220> FEATURE:
<221> NAME/KEY: modified_base
<222> LOCATION: (59)..(59)
<223> OTHER INFORMATION: um
<220> FEATURE:
<221> NAME/KEY: modified_base
<222> LOCATION: (60)..(60)
<223> OTHER INFORMATION: gm
<220> FEATURE:
<221> NAME/KEY: misc_feature
<222> LOCATION: (61)..(61)
<223> OTHER INFORMATION: 2'-O-methyl adenosine
<220> FEATURE:
<221> NAME/KEY: modified_base
<222> LOCATION: (62)..(62)
<223> OTHER INFORMATION: um
<220> FEATURE:
<221> NAME/KEY: modified_base
<222> LOCATION: (63)..(63)
<223> OTHER INFORMATION: gm
<220> FEATURE:
<221> NAME/KEY: misc_feature
<222> LOCATION: (64)..(64)
<223> OTHER INFORMATION: 2'-O-methyl adenosine
<220> FEATURE:
<221> NAME/KEY: modified_base
<222> LOCATION: (65)..(65)
<223> OTHER INFORMATION: gm
<220> FEATURE:
<221> NAME/KEY: modified_base
<222> LOCATION: (66)..(66)
<223> OTHER INFORMATION: cm
<220> FEATURE:
<221> NAME/KEY: modified_base
<222> LOCATION: (67)..(67)
<223> OTHER INFORMATION: um
<220> FEATURE:
<221> NAME/KEY: modified_base
<222> LOCATION: (68)..(68)
<223> OTHER INFORMATION: cm
<220> FEATURE:
<221> NAME/KEY: modified_base
<222> LOCATION: (69)..(70)
<223> OTHER INFORMATION: um
<220> FEATURE:
<221> NAME/KEY: modified_base
<222> LOCATION: (71)..(71)
<223> OTHER INFORMATION: cm
<220> FEATURE:
<221> NAME/KEY: modified_base
<222> LOCATION: (72)..(72)
<223> OTHER INFORMATION: gm
<220> FEATURE:
```

```
<221> NAME/KEY: modified_base
<222> LOCATION: (73)..(73)
<223> OTHER INFORMATION: um
<220> FEATURE:
<221> NAME/KEY: modified_base
<222> LOCATION: (74)..(74)
<223> OTHER INFORMATION: cm
<220> FEATURE:
<221> NAME/KEY: modified_base
<222> LOCATION: (75)..(75)
<223> OTHER INFORMATION: gm
<220> FEATURE:
<221> NAME/KEY: modified_base
<222> LOCATION: (76)..(76)
<223> OTHER INFORMATION: cm
<220> FEATURE:
<221> NAME/KEY: modified_base
<222> LOCATION: (77)..(77)
<223> OTHER INFORMATION: um
<220> FEATURE:
<221> NAME/KEY: modified_base
<222> LOCATION: (78)..(78)
<223> OTHER INFORMATION: cm
<220> FEATURE:
<221> NAME/KEY: modified_base
<222> LOCATION: (79)..(80)
<223> OTHER INFORMATION: um
<220> FEATURE:
<221> NAME/KEY: misc_feature
<222> LOCATION: (81)..(81)
<223> OTHER INFORMATION: inverted deoxyribonucleotide

<400> SEQUENCE: 52
aaggucccug aucgacgaag agcucaucag gguaacuaga gaucccucag acgcaagcug    60
augagcucuu cgucgcuguu t                                              81

<210> SEQ ID NO 53
<211> LENGTH: 28
<212> TYPE: RNA
<213> ORGANISM: Artificial sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (5)..(5)
<223> OTHER INFORMATION: um
<220> FEATURE:
<221> NAME/KEY: misc_feature
<222> LOCATION: (7)..(7)
<223> OTHER INFORMATION: 2'-O-methyl adenosine
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (15)..(15)
<223> OTHER INFORMATION: gm
<220> FEATURE:
<221> NAME/KEY: modified_base
```

```
<222> LOCATION: (17)..(17)
<223> OTHER INFORMATION: cm
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (21)..(21)
<223> OTHER INFORMATION: gm
<220> FEATURE:
<221> NAME/KEY: modified_base
<222> LOCATION: (22)..(22)
<223> OTHER INFORMATION: um
<220> FEATURE:
<221> NAME/KEY: modified_base
<222> LOCATION: (23)..(23)
<223> OTHER INFORMATION: cm
<220> FEATURE:
<221> NAME/KEY: modified_base
<222> LOCATION: (24)..(24)
<223> OTHER INFORMATION: um
<220> FEATURE:
<221> NAME/KEY: modified_base
<222> LOCATION: (25)..(26)
<223> OTHER INFORMATION: cm
<220> FEATURE:
<221> NAME/KEY: modified_base
<222> LOCATION: (27)..(27)
<223> OTHER INFORMATION: gm
<220> FEATURE:
<221> NAME/KEY: modified_base
<222> LOCATION: (28)..(28)
<223> OTHER INFORMATION: cm

<400> SEQUENCE: 53
cugaugagcu cuucgucgcu gucuccgc                                              28

<210> SEQ ID NO 54
<211> LENGTH: 12
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (10)..(12)
<223> OTHER INFORMATION: phosphorothioate backbone
<220> FEATURE:
<221> NAME/KEY: modified_base
<222> LOCATION: (11)..(11)
<223> OTHER INFORMATION: cm
<220> FEATURE:
<221> NAME/KEY: misc_feature
<222> LOCATION: (12)..(12)
<223> OTHER INFORMATION: ethylene glycol linker to SEQ ID NO: 55
<220> FEATURE:
<221> NAME/KEY: modified_base
<222> LOCATION: (12)..(12)
<223> OTHER INFORMATION: gm

<400> SEQUENCE: 54
cccucagacg cg                                                               12

<210> SEQ ID NO 55
<211> LENGTH: 17
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: ethylene glycol linker to the 3' end of SEQ ID
      NO: 54
```

```
<220> FEATURE:
<221> NAME/KEY: misc_feature
<222> LOCATION: (17)..(17)
<223> OTHER INFORMATION: ethylene glycol linker attached to inverted
      deoxyribose nucleotide T

<400> SEQUENCE: 55
gcagagcgac gaagagc                                                        17

<210> SEQ ID NO 56
<211> LENGTH: 19
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (19)..(19)
<223> OTHER INFORMATION: C3 linker attached to 5'end of SEQ ID NO: 57

<400> SEQUENCE: 56
ggagacagcg cgcucugca                                                      19

<210> SEQ ID NO 57
<211> LENGTH: 13
<212> TYPE: RNA
<213> ORGANISM: Artificial sequence
<220> FEATURE:
<223> OTHER INFORMATION: Synthetic polynucleotide
<220> FEATURE:
<221> NAME/KEY: modified_base
<222> LOCATION: (1)..(2)
<223> OTHER INFORMATION: gm
<220> FEATURE:
<221> NAME/KEY: misc_feature
<222> LOCATION: (1)..(1)
<223> OTHER INFORMATION: C3 linker attached to 3' end of SEQ ID NO: 56
<220> FEATURE:
<221> NAME/KEY: misc_feature
<222> LOCATION: (1)..(3)
<223> OTHER INFORMATION: Phosphorothioate backbone
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (13)..(13)
<223> OTHER INFORMATION: um

<400> SEQUENCE: 57
gguaacuaga gau                                                            13

<210> SEQ ID NO 58
<211> LENGTH: 58
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
```

```
<222> LOCATION: (1)..(2)
<223> OTHER INFORMATION: 2'-O-methyl adenosine
<220> FEATURE:
<221> NAME/KEY: misc_feature
<222> LOCATION: (1)..(5)
<223> OTHER INFORMATION: ribonucleotides
<220> FEATURE:
<221> NAME/KEY: modified_base
<222> LOCATION: (3)..(4)
<223> OTHER INFORMATION: gm
<220> FEATURE:
<221> NAME/KEY: modified_base
<222> LOCATION: (5)..(5)
<223> OTHER INFORMATION: um
<220> FEATURE:
<221> NAME/KEY: misc_feature
<222> LOCATION: (6)..(12)
<223> OTHER INFORMATION: deoxyribonucleotides
<220> FEATURE:
<221> NAME/KEY: misc_feature
<222> LOCATION: (13)..(57)
<223> OTHER INFORMATION: ribonucleotides
<220> FEATURE:
<221> NAME/KEY: modified_base
<222> LOCATION: (37)..(37)
<223> OTHER INFORMATION: um
<220> FEATURE:
<221> NAME/KEY: modified_base
<222> LOCATION: (39)..(39)
<223> OTHER INFORMATION: gm
<220> FEATURE:
<221> NAME/KEY: modified_base
<222> LOCATION: (41)..(41)
<223> OTHER INFORMATION: gm
<220> FEATURE:
<221> NAME/KEY: modified_base
<222> LOCATION: (44)..(44)
<223> OTHER INFORMATION: cm
<220> FEATURE:
<221> NAME/KEY: misc_feature
<222> LOCATION: (58)..(58)
<223> OTHER INFORMATION: inverted deoxyribonucleotide

<400> SEQUENCE: 58
aaggucccug aucgacgaag agcucaucag gguaacuaga gaucccucag acgcaagt      58

<210> SEQ ID NO 59
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(27)
<223> OTHER INFORMATION: ribonucleotides
<220> FEATURE:
<221> NAME/KEY: misc_feature
<222> LOCATION: (28)..(28)
<223> OTHER INFORMATION: inverted deoxyribonucleotide

<400> SEQUENCE: 59
gguaacuaga gaucccucag acgcaagt                                       28

<210> SEQ ID NO 60
<211> LENGTH: 29
<212> TYPE: RNA
<213> ORGANISM: Artificial sequence
<220> FEATURE:
<223> OTHER INFORMATION: Synthetic polynucleotide

<400> SEQUENCE: 60
cuugcgucug agggaucucu aguuaccuu                                      29
```